United States Patent
Whitfield et al.

(10) Patent No.: US 10,647,737 B2
(45) Date of Patent: May 12, 2020

(54) SULFATED-GLYCOLIPIDS AS ADJUVANTS FOR VACCINES

(71) Applicant: National Research Council of Canada, Ottawa (CA)

(72) Inventors: Dennis M. Whitfield, Ottawa (CA); G. Dennis Sprott, Ottawa (CA); Lakshmi Krishnan, Ottawa (CA)

(73) Assignee: National Research Council of Canada, Ottawa, Ontario (CA)

( * ) Notice: Subject to any disclaimer, the term of this patent is extended or adjusted under 35 U.S.C. 154(b) by 262 days.

(21) Appl. No.: 15/325,640

(22) PCT Filed: Jul. 10, 2015

(86) PCT No.: PCT/CA2015/000430
§ 371 (c)(1),
(2) Date: Jan. 11, 2017

(87) PCT Pub. No.: WO2016/004512
PCT Pub. Date: Jan. 14, 2016

(65) Prior Publication Data
US 2017/0158728 A1 Jun. 8, 2017

Related U.S. Application Data

(60) Provisional application No. 62/023,611, filed on Jul. 11, 2014.

(51) Int. Cl.
C07H 15/04 (2006.01)
A61K 39/00 (2006.01)
A61K 39/39 (2006.01)

(52) U.S. Cl.
CPC .......... *C07H 15/04* (2013.01); *A61K 39/0011* (2013.01); *A61K 39/39* (2013.01); *A61K 2039/54* (2013.01); *A61K 2039/55555* (2013.01); *A61K 2039/55572* (2013.01); *A61K 2039/57* (2013.01)

(58) Field of Classification Search
CPC .... C07H 15/04; A61K 39/39; A61K 39/0011; A61K 2039/55572; A61K 2039/55555; A61K 2039/57; A61K 2039/54
USPC ........................................................ 514/23
See application file for complete search history.

(56) References Cited

U.S. PATENT DOCUMENTS

| | | |
|---|---|---|
| 5,098,588 A | 3/1992 | Chang |
| 5,989,587 A | 11/1999 | Sprott et al. |
| 6,132,789 A | 10/2000 | Sprott et al. |
| 6,403,117 B1 | 6/2002 | Sprott et al. |
| 2003/0220270 A1 | 11/2003 | Hilgers et al. |
| 2005/0256060 A1 | 11/2005 | Hilgers et al. |

(Continued)

FOREIGN PATENT DOCUMENTS

| | | |
|---|---|---|
| CA | 2824398 A1 | 8/2011 |
| FR | 2672495 | 8/1992 |

(Continued)

OTHER PUBLICATIONS

Kloeppel et al. (Journal of Chromatography, Biomedical Applications (1991), 562(1-2), 369-76) (abstract sent).*

(Continued)

*Primary Examiner* — Eric Olson
*Assistant Examiner* — Michael C. Henry

(57) ABSTRACT

A synthetic charged glycolipid is described comprising a sulfated saccharide group covalently linked to the tree sn-1 hydroxyl group of the glycerol backbone of an archaeal core lipid via a beta linkage. The synthetic charged glycolipids include compounds of formula I wherein n is 0 or 1; R is hydrogen or hydroxyl; and Y is hydrogen or a sulfate group, at least one Y being a sulfate group; and including pharmaceutically acceptable salts thereof. The sulfated glycolipid produces stable archaeosomes at a mol % ratio of from 100:0 to 30:70 (sulfated glycolipid:uncharged glycolipid) and which induce a protective immune response, including $CD8^+$ and $CD4^+$ T cell responses. Archaeosomes comprising the sulfated glycolipids described have desirable adjuvant properties, particularly when mixed with uncharged glycolipid at a mol % ratio of about 50:50.

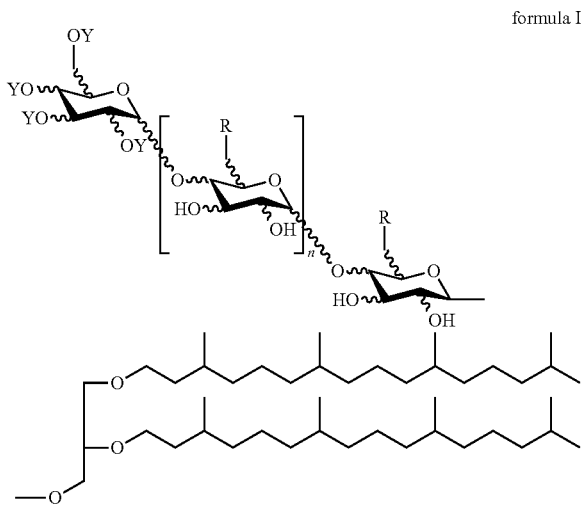

formula I

33 Claims, 17 Drawing Sheets

(56) References Cited

U.S. PATENT DOCUMENTS

| | | | |
|---|---|---|---|
| 2008/0220028 | A1 | 9/2008 | Patel et al. |
| 2009/0232880 | A1 | 9/2009 | Benvegnu et al. |
| 2009/0304723 | A1 | 12/2009 | Hilgers et al. |
| 2010/0297217 | A1 | 11/2010 | Rowland |
| 2010/0316657 | A1 | 12/2010 | Sprott et al. |

FOREIGN PATENT DOCUMENTS

| | | | |
|---|---|---|---|
| JP | 4279521 | | 5/1992 |
| JP | 4257596 | | 11/1992 |
| JP | 5023576 | | 2/1993 |
| WO | 9722333 | A1 | 6/1997 |
| WO | 0126683 | | 4/2001 |
| WO | 2007112567 | A1 | 10/2007 |
| WO | 20090040343 | A1 | 4/2009 |
| WO | 2011100955 | | 8/2011 |
| WO | 2014199297 | A1 | 12/2014 |

OTHER PUBLICATIONS

Kloeppel et al. (Journal of Chromatography, Biomedical Applications (1991), 562(1-2), 369-76).*

Sprott, G.D. et al., Adjuvant potential of archaeal synthetic glycolipid mimetics critically depends on the glyco head group structure; Glycobiology 2008; vol. 18 No. 77 pp. 559-565.

Kates, M., Structural analysis of phospholipids and glycolipids in extremely halophilic archaebacteria; Journal of Microbiological Methods; 1996, 25: 113-128.

Sprott, G.D. et al., Archaeosomes varying in lipid composition differ in receptor-mediated endocytosis and differentially adjuvant immune responses to entrapped antigen; Archaea 2003, 1:151-164.

Mathai, J.C. et al., Molecular mechanisms of water and solute transport across archaebacterial lipid membranes; The Journal of Biological Chemistry 2001276-27266-27271.

Geerdink, D. et al., Total synthesis of sulfolipid-1 2014; Chem. Commun 2014, 50, 2286-2288.

Sprott et al., Novel polar lipids of halophilic eubacterium planococcus H8 and archaeon haloferax volcanii, biochim biophys acta Sep. 22, 2003; 1633(3):179-88.

Eguchi T., et al., Total synthesis of archaeal 36-membered macrocyclic diether lipid, J. Org. Chem. 1997, 62(7), 1924-1933.

Eguchi T. et al., Total synthesis of archaeal 72-membered macrocyclic tetraether lipids, J. Org. Chem. 1998, 63(8), 2689-2698.

Dannenmuller O., et al., Membrane properties of archaeal diether phospholipids, Chemistry—A, European Journal 2000, 6(4), 645-654.

Hancock A.J. et al., Synthesis of sulfate esters of phosphatidylglycerol(diphytanyl ether analog), J. Lipid Res. 1973, 14, 430-437.

Van Boekel C.A.A. et al., Synthesis of two purple-membrane glycolipids and the glycolipid sulfate O-(b-D-gluocopyanosyl-3-sulfate)-(1,6)-O-a-D -mannopyranosyl-(1,2)-O-a-D-flucopyanosyl-(1-1)-2,3-di-O-phytanyl-sn-glycerol, Carbohydr Res. 1984, 133, 219-234.

Kamikawa T. et al., Synthesis of 2,3 di-O-phytanyl 1-O-(a-D-glucopyranosyl) sn glycerol derivatives, analogues of polar lipids isolated from a halophilic bacterial strain, Glycoconj. J. 1993, 10(3), 235-239.

Velty R. et al., n-Pentenyl furanosides and related glycosyl donors for the synthesis of archaeol glycolipid analogues, Synlett 1996, 817-819.

Koga Y. et al., Recent advances in structural research on ether lipids from archaea including comparative and physiological aspects, Biosci. Biotechnol. Biochem. 2005, 69(11), 2019-2034.

Sprott D. et al., A structural comparison of the total polar lipids from the human archaea methanobrevibacter smithii and methanoshaera stadtmanae and its relevance to the adjuvant activities of their liposomes, Biochim, Biophys. Acta 1999, 1440(23), 275-88.

Krishnan et al., Archaeosome vaccine adjuvants induce strong humoral, cell mediated and memory responses: comparison to conventional liposomes and alum, Infect. Immun. 2000, 68(1), 54 63. p. 57, col. 1, para. 3.

Patel G.B. et al., Archaeosome immunostimulatory vaccine delivery system, Curr. Drug Del. 2005, 2, 407-421.

International Search Report and Written Opinion for Application No. PCT/CA2015/000430.

International Preliminary Report on Patentability for Application No. PCT/CA2015/000430 dated Jan. 17, 2017.

Auzanneau et al., Incidence and avoidance of stereospecific 1,2-ethylthio group migration during the snythesis of ethyl 1-thio-alpha-L-rhamnopyranoside 2,3-orthoester, Carbohydrate Research, 212 (1991) 13-24.

Barrett et al., (Phenylthio) nitromethane, Organic Syntheses, Coll. vol. 8, p. 550 (1993); vol. 68, p. 8 (1990).

Dicaire et al., Isopranoid- and dipalmitoyl-aminophopholipid adjuvants impact differently on longevity of CTL immune responses, Journal of Liposome Research, 2010, 20:4, 304-314.

Douglas et al., Tuning glycoside reactivity: new tool for efficient oligosaccharide synthesis, J. Chem. Soc., Perkin Trans. 1, 1998.

Gold et al., A concise synthesis of Globotriaosylsphingosine, Eur. J. Org. Chem. 2011, 1652-1663.

Huang, et al., Iterative one-pot synthesis of oligosaccharides, Angew. Chem. 2004, 116, 5333-5336.

Krishnan et al., Archaeosomes as self-adjuvanting delivery systems for cancer vaccines, Journal of Drug Targeting, 2003 vol. 11 (8-10), po. 515-524.

Mandal et al., Mild and efficient hydrolysis of thioglycosides to glycosyl hemiacetals using N-iodosaccharin, Synlett 2007, No. 8, pp. 1207-1210.

Patel et al., Recognition of CD1d-sulfatide mediated by a type II natural killer T cell antigen receptor, Nature Immunology, vol. 13, No. 9, Sep. 2012.

Purves, relations between rotatory power and structure inthe sugar group. XXI. Beta-thiophenol glycosides of glucose, xylose, lactose and cellobiose, Beta-thiophenol glycosides of sugars, 3619-3629 Dec. 1929.

Ray et al., Synthesis of di- and tri-saccharides related to the poly-saccharide from *Streptococcus pneumoniae* type 23 and a study of their inhibition in the precipitin reaction, Carbohydrate Research, 197 (1990) 93-100.

Sprott et al., Stability of liposomes prepared from archaeobacterical lipids and physphatidylcholine mixtures, cells and materials: vol. 6: No. 1, Article 16 1996.

Sprott et al., Archaeobacterial ether lipid liposomes as vaccine adjuvants, Methods in Enzymology, 2003 vol. 373, 155-172.

Tomoo et al., An efficient short-step total synthesis of ganglioside GM: effective usage of the neighbouring group participation strategy, Carbohydrate Research 284 (1996) 207-222.

Whitfield et al., Synthesis of archaeal glycolipid adjuvants—what is the optimum number of sugars? Carbohydrate Research 343 (2008) 2349-2360.

Whitfield et al., Development of new glycosylation methodologies for the synthesis of archaeal-derived glycolipid adjuvants, Carbohydrate Research 345 (2010) 214-229.

Wolfrom, Methods in carbohydrate chemistry, vol. 1, Analysis and preparation of sugars, 1963.

Ziegler et al., Chemoenzymatic synthesis of enantiomericaly pure alkene 1,2-diols and glycosides thereof, Tetrahedron: Asymmetry 9 (1998) 765-780.

Mehta et al., Ready access to sialylated oligosaccharide donors, Org. Lett, vol. 2, No. 6 2000.

Krishnan et al., Archaeosome adjuvants: immunological capabilities and mechanism(s) of action, Vaccine, vol. 26, No. 17, Apr. 16, 2008, pp. 2043-2055.

Extended European Search Report dated Jan. 31, 2018.

* cited by examiner a)

b)

SULFATED-GLYCOLIPIDS AS ADJUVANTS FOR VACCINES

FIELD OF INVENTION

The present invention relates to charged glycolipids, and particularly, to charged glycolipids and formulations thereof that can be used to prepare archaeosomes and other lipid compositions which are useful as adjuvants.

BACKGROUND OF THE INVENTION

Vaccines are biological preparations that improve immunity to a particular disease. They are frequently used in the prophylaxis of humans and animals to protect against infectious diseases caused by bacteria, viruses and parasitic organisms. Therapeutic vaccines are also under investigation, such as for the treatment of cancer.

The antigens used in vaccines may include a variety of agents, such as killed pathogenic organisms, pathogenic organisms which are alive but modified or attenuated, proteins, recombinant proteins or fragments thereof. It is also often necessary to add an adjuvant to enhance the host immune response to the antigen, and in some cases slow the release of the antigens from the injection site.

A wide range of adjuvants have been studied for use in vaccines, including lipids and liposomes, in which an antigen of interest can be encapsulated within a lipid vesicle.

Glycolipids

Glycolipids are of interest as adjuvant ingredients as they can target specific receptors on antigen presenting cells (APC's). However, since most glycolipids are uncharged, a stable bilayer does not form when attempts are made to prepare glycolipid-liposome based vaccine carriers. According to present knowledge, a liposome or archaeosome composed solely of glycolipid(s) would not form a stable structure. This can be solved by adding phospholipids with associated charge to the glycolipid formulation.

For instance, archaeol has been isolated from hydrolysed polar lipid extracts of *Halobacterium salinarum* to use as the lipid precursor to chemically synthesize various polar lipids, including glycolipids (Sprott, G. D., Dicaire, C. J., Cote, J. P., and Whitfield, D. M. 2008. *Glycobiology* 18:559-565; Whitfield, D. M., Yu, S. H., Dicaire, C. J., and Sprott, G. D. 2010. *Carbohydr. Res.* 345:214-229). The lipids so generated are described as synthetic, or more precisely as semisynthetic, because the lipid moiety with specific archaeal stereochemistry is of biological origin, whereas the polar head group is synthesized or conjugated to the free sn-1 hydroxyl of the glycerol backbone of the archaeol to give a new lipid structure. These glycolipids were mixed with phospholipids to make archaeosomes having a negative-charge, and with adjuvant activities that varied with the structure of the polar head group of the lipid (Sprott, G. D., Dicaire, C. J., Cote, J. P., and Whitfield, D. M. 2008. *Glycobiology* 18:559-565).

There are, however, several potential limitations with adding additional phospholipid as part of a glycolipid-liposome/archaeosome adjuvant. For instance, more lipids are required in the formulation, adding to complexity. In addition, the active glycolipid is diluted to much less than 100%, which can lead to reduced efficacy. Costs associated with synthesis also escalate as more lipids are required in the formulation. The stability of phosphodiester linkages to enzymatic and chemical attack is also not satisfactory, especially for harsh routes of delivery (e.g. oral), and any instability of the lipid vesicles resulting from these phosphodiester linkages can result in loss of cargo and therefore reduced efficacy.

Sulfated Glycolipids

Sulfated glycolipids (S-glycolipids) are found in some *Halobacteria* (Kates, M. 1996. *J. Microbiol. Methods* 25:113-128) and have been part of the total polar lipids (TPL) from several archaeal lipid extracts used to make archaeosomes. These archaeosomes had no improved adjuvant activity (Sprott, G. D., Sad, S., Fleming, L. P., Dicaire, C. J., Patel, G. B., and Krishnan, L. 2003. *Archaea* 1:151-164) or stability (Mathai, J. C., Sprott, G. D., and Zeidel, M. L. 2001. *J. Biol. Chem.* 276:27266-27271) compared to total polar lipid archaeosomes lacking S-glycolipids. Indeed the opposite was true, indicating that 5-glycolipid would not be the active ingredient. CD8$^+$ T cell activity with total polar lipids (TPL) from extreme halophiles with S-glycolipid was relatively short-lasting compared to TPL of *M. smithii* or *Thermoplasma acidophilum* (Krishnan, L. and Sprott, G. D. 2003. *Journal of Drug Targeting* 11:515-524) that have no S-glycolipids. An improved antibody response with certain TPL of extreme halophiles was shown to be the result of the presence of a major lipid PGP—O—CH$_3$, specifically archaetidylglycerolmethylphosphate (Whitfield, D. M., Yu, S. H., Dicaire, C. J., and Sprott, G. D. 2010. *Carbohydr. Res.* 345:214-229), rather than S-glycolipids. Other non-isoprenoid S-glycolipids such as sulfatides (predominantly 3-sulfate-β-D-Gal$_p$(1,1)Ceramide) (Patel, O., Pellicci, D. G., Gras, S., Sandoval-Romero, M. L., Uldrich, A. P., Mallevaey, T., Clarke, A. J., Le Nours, J., Theodossis, A., Carden, S. L., Gapin, L., Godfrey, D. I., Rossjohn, J. 2012. *Nat. Immunol.* 857-63) and the sulfolipid-1 (Geerdink, D.; Minnaard, A. J. 2014. *Chem. Commun.* 50:2286-2288) from mycobacteria (6-sulfate-α-D-Glc$_p$(1,1)-α-D-Glc$_p$ substituted with 1 or more mycolic acids, typically 4) have been described to have immunological activity but with immunological activities distinct from archaeosomes.

SUMMARY OF THE INVENTION

A need therefore exists for an improved glycolipid-liposome/archaeosome adjuvant having both enhanced stability and suitable efficacy.

An object of the invention is thus to provide a glycolipid that can be used to prepare archaeosomes and other lipid compositions which are useful as adjuvants.

Described herein are sulfated isoprenoid glycolipids that can be synthetically produced, which generate stable archaeosomes, and that have desirable adjuvant properties. Liposomes prepared using these sulfated glycolipids are useful as an antigen carrier to target antigen-presenting cells for vaccine adjuvant applications.

There is accordingly provided a synthetic charged glycolipid comprising a sulfated saccharide group which is covalently linked to the free sn-1 hydroxyl group of the glycerol backbone of an archaeal core lipid.

In an embodiment, the sulfated saccharide group is covalently linked to the free sn-1 hydroxyl group of the glycerol backbone of the archaeal core lipid via a beta linkage.

The archaeal core lipid may, in certain embodiments, be an archaeal isoprenoid glycerolipid in which the polar head group is removed, including archaeol but not limited thereto.

Accordingly, in particular non-limiting embodiments, the sulfated saccharide group may be linked to an archaeol (sn-2,3-di-O-phytanylglycerol) moiety of the following structure:

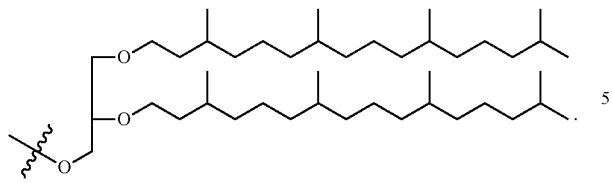

The archaeol moiety may be derived from archaeol which is obtained by chemical synthesis, or from the polar lipids of an archaebacterium, such as but not limited to *Halobacterium salinarum*.

In further embodiments, the synthetic charged glycolipid may be a compound as defined by formula I:

formula I

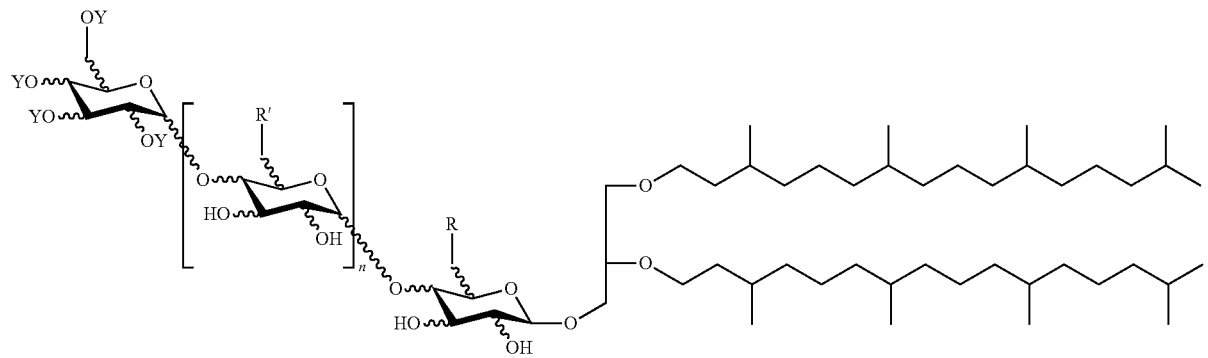

wherein n is 0 or 1; R and R' are independently hydrogen or hydroxyl; and Y is hydrogen or a sulfate group, at least one Y being a sulfate group; and including pharmaceutically acceptable salts thereof. Curly bonds as shown in the formula indicate either R or S stereochemistry at the sugar atoms, and include all possible combinations.

In the above embodiments, the sulfated saccharide group may comprise monosaccharide moieties including mannose (Man), glucose (Glc), rhamnose (Rha) or galactose (Gal) moieties, or combinations thereof.

The sulfated saccharide group will comprise at least one sulfate moiety. In certain non-limiting embodiments, the at least one sulfate moiety may be positioned at the 6' position of the terminal monosaccharide moiety. In certain preferred embodiments, the sulfated saccharide group comprises one sulfate moiety.

In further non-limiting embodiments of the synthetic charged glycolipid, which are as defined by the compound of formula I, n may be 0 and R may be OH. In such embodiments, the sulfated saccharide group may comprise mannose (Man), glucose (Glc) or galactose (Gal) monosaccharide moieties, including combinations thereof.

In yet further embodiments, the synthetic charged glycolipid may be one of the following compounds: 6″-sulfate-α-D-Man$_p$-(1,6)-β-D-Gal$_p$-(1,4)-β-D-Glc$_p$-(1,1)-archaeol, or 6″-sulfate-β-D-Glc$_p$-(1,6)-β-D-Gal$_p$-(1,4)-β-D-Glc$_p$-(1,1)-archaeol, or 6″-sulfate-β-D-Gal$_p$-(1,4)-β-D-Glc$_p$-(1,6)-β-D-Glc$_p$-(1,1)-archaeol.

In further embodiments, which are also considered non-limiting yet may in certain instances be preferred, the sulfated saccharide group may be a sulfated oligosaccharide group, such as a sulfated disaccharide or trisaccharide group. In one particular non-limiting embodiment, the sulfated disaccharide group may be a sulfated lactosyl group, or more specifically, a 6'-S-lactosyl group. In other non-limiting embodiments, the sulfated lactosyl group is 6'-sulfate-β-D-Gal$_p$-(1,4)-β-D-Glc$_p$.

In one example of the synthetic charged glycolipid described herein, the synthetic charged glycolipid is: Sodium (2R)-2,3-Bis[(3R,7R,11R)-3,7,11,15-tetramethylhexadecyloxy]propan-1-yl 4-O-(6-O-sulfo-b-D-galactopyranosyl)-b-D-glucopyranoside, and has the structure:

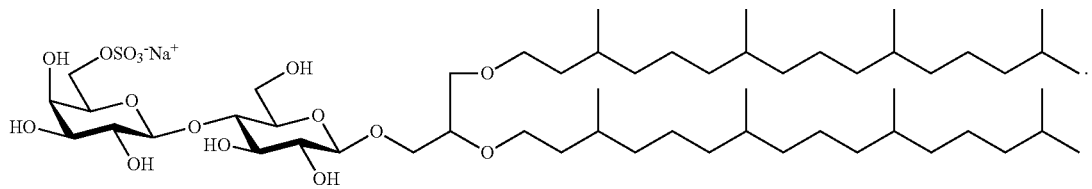

In further embodiments of the synthetic charged glycolipid described herein, the pharmaceutically acceptable salts may include sodium, calcium or magnesium salts, or any other salt known to be pharmaceutically acceptable.

Also provided herein is an archaeosome comprising at least one synthetic charged glycolipid as described above.

In non-limiting embodiments, the archaeosome may comprise synthetic charged glycolipids only, or may comprise at least one additional lipid. In the latter case, the at least one additional lipid may comprise a neutral, or uncharged glycolipid. For example, yet without wishing to be limiting in any way, the at least one additional lipid may be a lactosylarchaeol, a rhamnosyl-lactosylarchaeol, a triglucosylarchaeol, monophosphoryl Lipid A, or combinations thereof.

lipid, and processing the uncharged glycolipid to add a sulfate moiety to the saccharide group. In certain embodiments, yet without wishing to be limiting, the archaeal core lipid may be obtained by isolation from archaeal cells.

In addition, there is provided herein a method for producing an archaeosome as described above, or comprising the synthetic charged glycolipid as described above, comprising the steps of obtaining a synthetic charged glycolipid as described above, optionally adding at least one additional lipid, optionally adding at least one peptide or protein, and providing conditions for the formation of the archaeosome.

Also provided herein is a method for the synthesis of a sulfated glycolipid of formula 11:

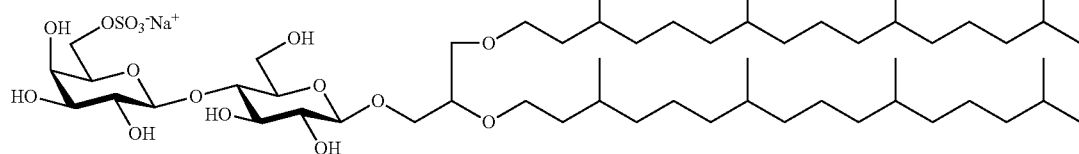

The mol % ratio of the synthetic charged glycolipid to the neutral or uncharged lipid also vary, in some embodiments ranging from about 100:0 to about 30:70, or preferably about 50:50.

In further embodiments, the archaeosomes may be formulated to have a surface charge ranging from about −20 mV to about −60 mV. As an example, the archaeosome may comprise 6'-sulfate-lactosylarchaeol and uncharged lactosylarchaeol in a mol % ratio of from 100:0 to 30:70, or about 50:50, in which case the surface charge of the archaeosome may preferably be from about −25 to about −45 mV.

The archaeosomes may in particular embodiments also have an average diameter of between about 50 nm and about 350 nm.

Also described herein is a vaccine or composition comprising an adjuvant and an antigen, the adjuvant comprising an archaeosome as described above. In non-limiting embodiments of the vaccine or composition, the antigen may comprise a peptide or protein.

The vaccine or composition can be used for the promotion of an immune response in a subject. Preferably, yet without limitation, the immune response may be a protective $CD8^+$ T cell response, a protective $CD4^+$ T cell response, or both.

In particular embodiments, the immune response May provide protection against cancer or an infectious agent.

The vaccine or composition may be administered by injection, or by other routes as known in the art.

Also provided herein is a method of promoting an immune response in a subject, the method comprising administering a vaccine or composition as described above in an amount effective to produce an immune response in said subject.

According to the above described uses and methods, the subject or patient may be a mammal, and in particular embodiments a human.

Methods are also provided herein for producing a synthetic charged glycolipid as described above, comprising the steps of: obtaining archaeal core lipid, processing the archaeal core lipid to covalently link a saccharide group to the free sn-1 hydroxyl group of the glycerol backbone of the archaeal core lipid, thereby producing an uncharged glycothe method comprising:
i) reacting lactose with acetic anhydride and sodium acetate to produce peracetyl-β-D-lactose of formula 1a:

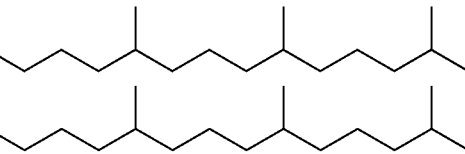

ii) converting the peracetyl-β-D-lactose of formula 1a to a thiophenol glycoside of formula 1b or a thioethyl glycoside of formula 1c:

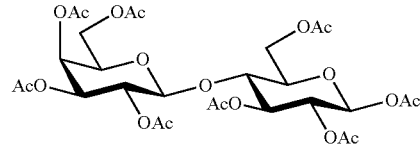

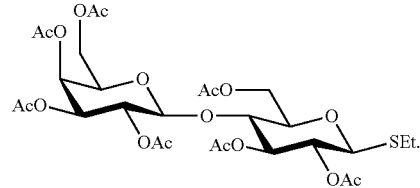

iii) deacetylating the thiophenol glycoside of formula 1b or the thioethyl glycoside of formula 1c followed by benzylidene formation and perbenzoylation to produce a protected thioglycoside of formula 2a or 2b:

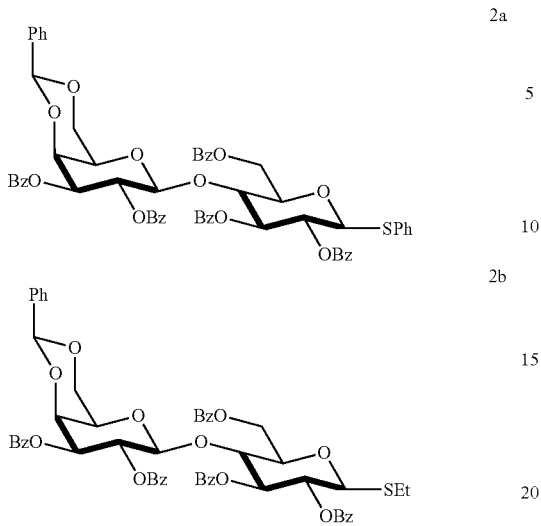

iv) reacting archaeol with the thioglycoside donors of formula 2a or 2b to produce the glycosylated archaeol of formula 4:

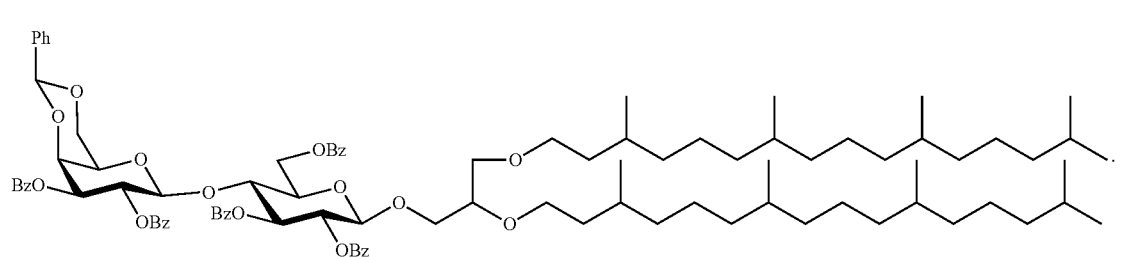

v) cleaving the benzylidene of the protected thioglycoside of formula 4 to give a diol of formula 5:

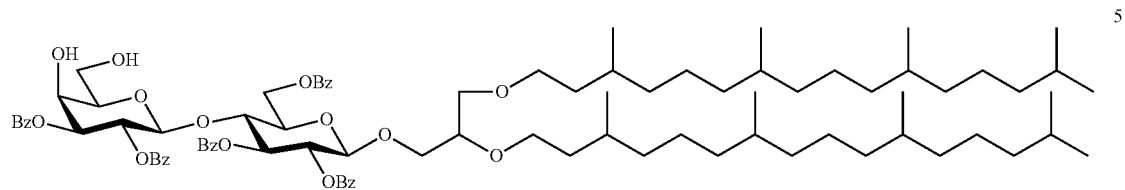

vi) regioselectively sulfating on the primary hydroxyl of the disaccharide glycolipid of formula 5 to give a protected sulfated glycolipid of formula 10:

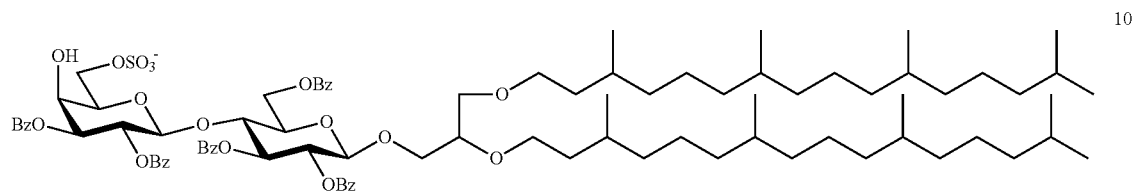

and vii) debenzoylating the protected sulfated glycolipid of formula 10 to produce the sulfated glycolipid of formula 11:

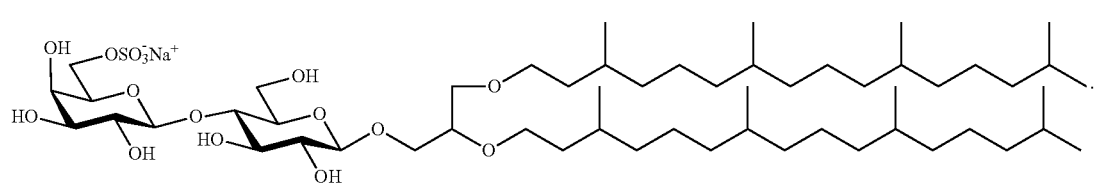

Other embodiments will also become apparent from the following detailed description and drawings.

BRIEF DESCRIPTION OF THE DRAWINGS

These and other features of the invention will become more apparent from the following description in which reference is made to the following drawings.

DETAILED DESCRIPTION

Figure 1:
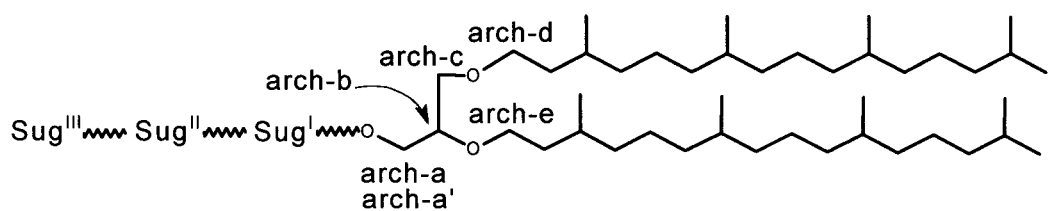
FIG. 1 shows the generalized structure for the modified glycolipids chemically synthesized, and showing labelling for NMR assignments (arch for archaeol, Sug for sugar).

Lipid vesicles (liposomes and archaeosomes) for drug delivery or antigen delivery, and other applications, have been heavily based in the past on phospholipid compositions. Many phospholipids are readily available from chemical suppliers, but these lipids are unstable to the various phospho-hydrolyzing enzymes found in vivo.

A new class of lipid-based carrier/adjuvant is described herein, in which the lipid formulation comprises a negatively charged, synthetic or semi-synthetic, sulfated-glycoarchaeol.

Thus, in embodiments of the described invention, a negative charge is introduced into the bilayer of the hydrated lipid(s) by one or more sulfate moieties added chemically to the glycogroup of a glycolipid, i.e. a glycoarchaeol. Archaeol is very stable to harsh synthesis conditions as it has stable ether linkages to saturated isopranoid chains. The result is a sulfated-glycolipid that readily hydrates to form stable structures capable of entrapping a compound, such as but not limited to proteins and peptides.

In certain non-limiting embodiments of the invention, synthesis of the sulfated-glycoarchaeols can be achieved beginning with the archaeol precursor (2,3-di-O-phytanyl-sn-glycerol) obtained from *Halobacterium salinarum* or *Halobacterium volcanii*.

In contrast to glycolipids that are neutral in charge, the sulfated glycolipids of the present invention hydrate readily to form stable carrier vesicles. In certain non-limiting embodiments, such vesicles can be prepared without the necessity of including other lipids, such as phospholipids. Dilution of the active lipid can therefore be controlled.

For example, yet without wishing to be limiting in any way, it may in certain embodiments be desirable to minimize dilution of the active lipid in the liposome formulation. This may be, for instance, to reduce costs associated with including additional lipids in the formulation.

In other non-limiting embodiments, it may be beneficial to combine the sulfated glycolipids of the present invention with a second lipid, such as a synthetic archaeal lipid, or with a co-adjuvant lipid such as monophosphoryl lipid A or other known hydrophobic compounds with complimentary adjuvant properties.

As demonstrated herein, sulfated-glycoarchaeol archaeosomes carrying antigen raise in mice a robust antigen-specific $CD8^+$ T cell response, as seen in Elispot or CTL assays of splenic cells from immunized mice, as well as a strong antibody response to the antigen. Studies using solid tumor models also are shown herein to give rise to protection using sulfated-glycoarchaeol archaeosomes of the present invention.

Archaeosomes tested as vaccine adjuvants include synthetic lipids not found in nature, such as but not limited to 6'-sulfate-β-D-Gal-(1,4)-β-D-Glc-(1,1)-archaeol. In certain embodiments, and without wishing to be limiting in any way, advantages of the sulfated-archaeosomes described herein (including by extension sulfated-liposomes) may include: ease of formulation, resistance to phospholipases, and enhanced adjuvant activity of glycolipids without the need to include other charged lipids.

Long-lasting immune responses were observed for the new class of archaeosomes described herein, yet were unexpected based on the fact that long-term $CD8^+$ T cell responses have been linked to the required presence of caldarchaeol membrane-spanning lipids (Krishnan, L. and Sprott, G. D. 2003. Journal of Drug Targeting 11: 515-524). Compared to the longevity of the $CD8^+$ T cell response to various conventional liposome-OVA vaccines (Dicaire, C. J., Yu, S. H., Whitfield, D. M., and Sprott, G. D. 2010. *J. Liposome Res.* 20:304-314), S-glycolipid archaeosomes have actually been found in certain embodiments to be superior, indicating a possible slow metering of antigen to the immune system.

Figure 2:
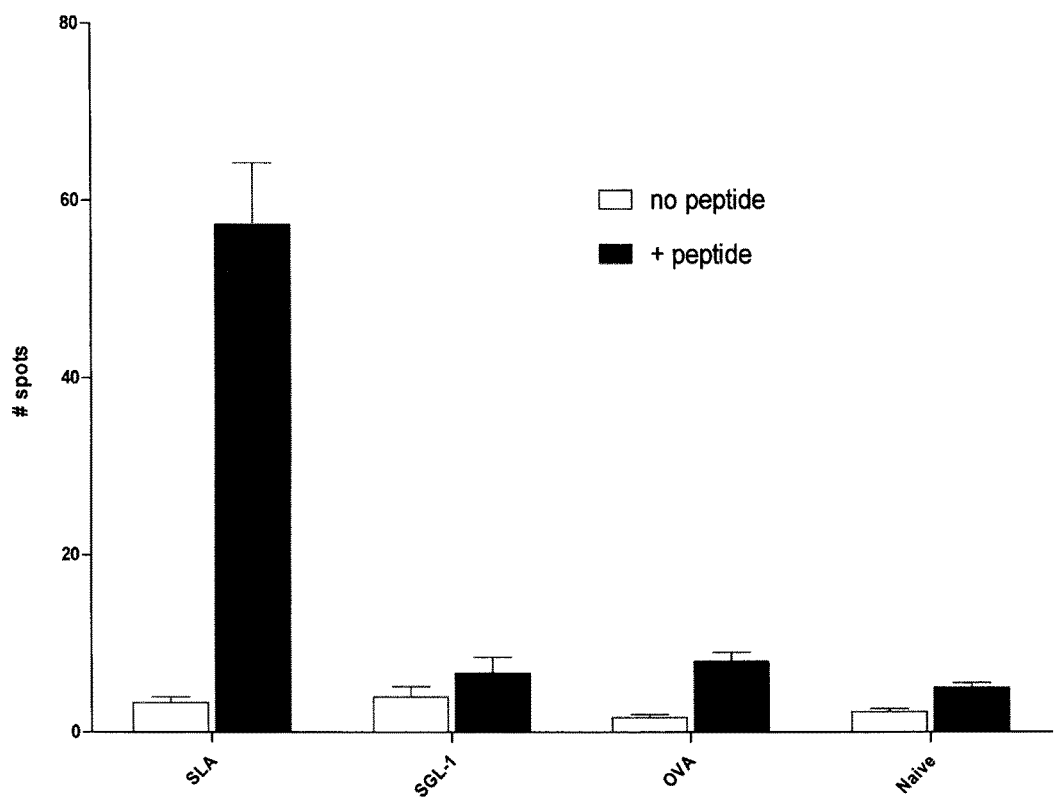
FIG. 2 shows a graph comparing antigen-specific CD8+ T cell activity in splenic cells of mice immunized with antigen entrapped in archaeosomes prepared from synthetic S-lactosylarchaeol (SLA) or biological sulfated glycolipid-1 (SGL-1; purified from Haloferax volcanii).

A sulfated glycolipid (SGL-1) occurs naturally in certain extreme halophiles (Kates, M. 1996. *J. Microbiol. Methods* 25: 113-128). However, it was unexpectedly found herein that the adjuvant capability of SGL-1 archaeosomes is much less than is found for the negatively charged, synthetic or semi-synthetic, sulfated-glycoarchaeol synthetic S-lactosylarchaeol (SLA) not found in nature (FIG. 2). This finding reveals that synthesis of the negatively charged, synthetic or semi-synthetic, sulfated-glycoarchaeols as described herein, and which have optimized structural detail (including but not limited to optimization in α versus β configurations, linkages, sugar types and number of sugar units, and sulfation position) may in certain embodiments provide a new class of superior synthetic archaeosome.

Thus, synthetic archaeosomes are provided herein with improved properties. In certain embodiments, sulfated lactosylarchaeol may be preferred, in part because lactose is an inexpensive starting material for synthesis, and because the data presented herein show S-lactosylarchaeol to have promise as an adjuvant.

In further embodiments, a terminal sulfated-sugar can be added to lactosylarchaeol as both a targeting and charged moiety. Targeting of receptors on antigen-presenting cells by sulfated-glycoarchaeols is thus combined with stability and longevity properties to provide an improved adjuvant.

Definitions

Archaeal lipid refers to a polar lipid common to the Domain Archaea typified by isoprenoid chains with R-stereochemistry and in ether linkage to the sn-2,3 carbons of the glycerol backbone.

Archaeal refers to sn-2,3-di-O-phytanylglycerol, which has the following structure:

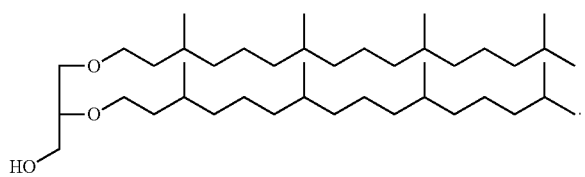 [SMILES: CC(C)CCCC(C)CCCC(C)CCCC(C)CCOCC(CO)OCCC(C)CCCC(C)CCCC(C)CCCC(C)C]

Archaeosome refers to liposomes comprised of archaeal-like isoprenoid lipids, as originally proposed in Sprott, G. D., Dicaire, C. J., Fleming, L. P., and Patel, G. B, 1996. *Cells and Materials* 6:143-155.

Conventional lipids refers to the glycero-ester linked fatty acyl lipids common to the Domains Eukarya and Bacteria.

Conventional liposome refers to those liposomes made from conventional lipids.

Sulfated-glycolipid is referred to as S-glycolipid.

SLA refers to S-lactosylarchaeol or 6'-sulfate-β-D-Gal$_p$-(1,4)-β-D-Glc$_p$-(1,1)-archaeol.

S$_2$LA refers to two sulfated moieties linked to lactosylarchaeol or 4'-6'-disulfate-β-D-Gal$_p$-(1,4)-β-D-Glc$_p$-(1,1)-archaeol.

Glc$_3$A, triglucosylarchaeol, or gentiotriosylarchaeol refers to synthetic β-Glc$_p$-(1,6)-β-Glc$_p$-(1,6)-β-D-Glc$_p$-(1,1)-archaeol.

S-Glc-Tri-A/LA refers to 6'-sulfated β-D-Glc$_p$-(1,6)-β-D-Gal$_p$-(1,4)-β-D-Glc$_p$-(1,1)-archaeol.

Man$_3$A or trimannosylarchaeol refers to synthetic α-D-Man$_p$-(1,2)-α-Man$_p$-(1,2)-α-D-Man$_p$-(1,1)-archaeol.

Rha-LA refers to Rhamnose-lactosyl archaeol, or α-L-Rhap-(1,6)-β-D-Galp-(1,4)-β-D-Glcp-(1,1)-archaeol.

TPL refers to total polar lipids extracted from biomass. Herein, TPL is prepared from biomass of *Methanobrevibacter smithii* (Sprott, G. D., Brisson, J., Dicaire, C. J., Pelletier, A. K., Deschatelets, L. A., Krishnan, L., and Patel, G. B. 1999. *Biochim. Biophys. Acta* 1440:275-288).

OVA refers to ovalbumin Type VI, Sigma.

PHAD refers to monophosphoryl lipid A from Avanti Polar Lipids, Inc.

SGL-1 refers to sulfatedglycolipid-1 purified from *Haloferax volcanii* (Sprott, G. D., Larocque, S., Cadotte, N., Dicaire, C. J., McGee, M., and Brisson, J. R. 2003. *Biochim. Biophys. Acta* 1633:179-188) with structure 6'-HSO$_3$-D-Man$_p$-α-1,2-D-Glc$_p$-α-1,1-archaeol.

CTL refers to cytotoxic T lymphocyte response.

The term "pharmaceutically acceptable salt" as used herein refers to salts which are known to be non-toxic and commonly used in the pharmaceutical literature. Particular examples of pharmaceutically acceptable salts include sodium, calcium and magnesium salts of the described synthetic charged glycolipids.

Synthetic Charged Glycolipids

As described herein, there is provided a synthetic charged glycolipid comprising a sulfated saccharide group which is covalently linked to the free sn-1 hydroxyl group of the glycerol backbone of an archaeal core lipid via a beta linkage.

The archaeal core lipid may, in certain embodiments, be an archaeal isoprenoid glycerolipid in which the polar head group is removed, including archaeol but not limited thereto. Accordingly, in particular non-limiting embodiments, the sulfated saccharide group may be linked to an archaeol (sn-2,3-di-O-phytanylglycerol) moiety of the following structure:

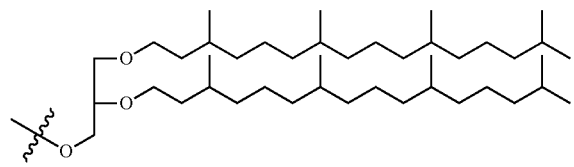 [SMILES: *OCC(COCCC(C)CCCC(C)CCCC(C)CCCC(C)C)OCCC(C)CCCC(C)CCCC(C)CCCC(C)C]

Thus, in certain embodiments, a compound is provided having the structure of formula I:

formula I

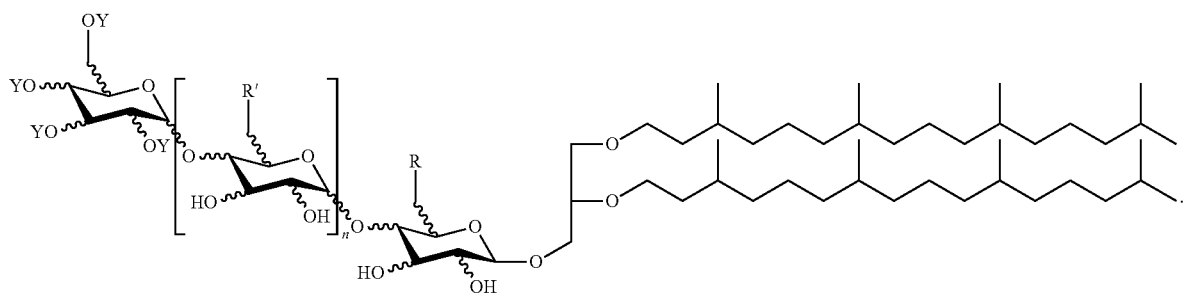

wherein n is 0 or 1;

R and R' are independently hydrogen or hydroxyl; and

Y is hydrogen or a sulfate moiety, at least one Y being a sulfate moiety;

including pharmaceutically acceptable salts thereof.

The compound of formula I may be synthetic or semi-synthetic, since the archaeol precursor can be obtained either by chemical synthesis or from the polar lipids of an archaebacterium, such as but not limited to *Halobacterium salinarum* and *Halobacterium volcanii*. Due to the complexity of the archaeol molecule, it is in many embodiments preferred to use a source of natural archaeol, e.g. generated from the polar lipids of *H. salinarum* or *H. volcanii*, by removing the natural various head groups through hydrolysis. Other sources of natural archaeol exist, and can also be used in the synthesis of the compounds described herein.

In certain embodiments, the saccharide may comprise mannose (Man), glucose (Glc), rhamnose (Rha) or galactose (Gal) moieties.

In certain embodiments, n is 0 and R is OH. In such embodiments the saccharide may comprise mannose, glucose or galactose moieties, or combinations thereof. Non-limiting examples of these embodiments include 6"-sulfate-Man$_p$-β-D-Gal$_p$(1,4)-β-D-Glc$_p$-(1,1)-archaeol, 6"-sulfate-Glc$_p$-β-D-Gal$_p$-(1,4)-β-D-Glc$_p$-(1,1)-archaeol or 6"-sulfate-β-D-Gal$_p$(1,4)-β-D-Glc$_p$-(1,6)-β-D-Glc$_p$-(1,1)-archaeol.

In further embodiments, the compound may comprise 1, 2, 3 or 4 sulfate moieties. For example, yet without wishing to be limiting, the compound may comprise one sulfate moiety at the 6' position of the terminal saccharide moiety. Additional sulfate moieties may be added without limitation.

In one particular embodiment, the compound is: (2R)-2,3-Bis[(3R,7R,11R)-3,7,11,15-tetramethylhexadecyloxy] propan-1-yl 4-O-(6-O-sulfo-β-D-galactopyranosyl)-β-D-glucopyranoside, and has the structure:

is released from the archaeosomes within the phagolysosome, giving rise to MHC class II presentation to CD4$^+$ T cells.

The biological activity observed, including the generation of immune responses in both CD8$^+$ and CD4$^+$ T-cells, suggests that archaeosomes comprising the described synthetic charged glycolipids, including the compounds of formula I, may in certain embodiments be useful as adjuvants and in vaccines for treating intracellular pathogen infections and cancers. More specifically, yet without wishing to be bound by theory in any way, an immune response is shown in the Examples to be mounted in immunized animals against the antigens carried by archaeosomes and

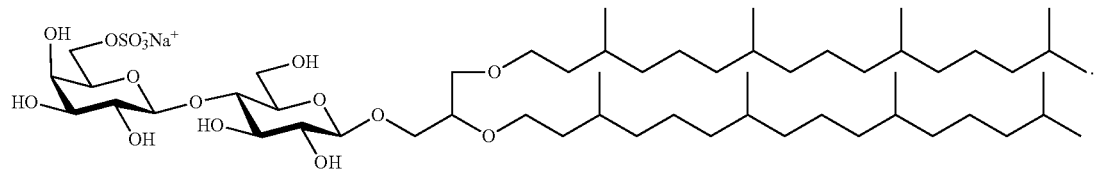

Archaeosomes:

Also provided herein is an archaeosome comprising at least one synthetic charged glycolipid, or compound of formula I, as described above.

The archaeosome may comprise synthetic charged glycolipids only, such as that depicted in formula I, or may comprise one or more additional lipids. In the latter case, the additional lipid(s) may comprise, without limitation, a neutral, or uncharged glycolipid such as a lactosylarchaeol, a rhamnosyl-lactosylarchaeol, a triglucosylarchaeol, monophosphoryl Lipid A, or combinations thereof. The mol % ratio of the synthetic charged glycolipid to the neutral or uncharged lipid may vary from about 100:0 to about 30:70, including all possible ratios within these ranges such as 95:5, 90:10, 80:20, 70:30, 60:40, 55:45, 45:55, 40:60, and 35:65, and preferably about 50:50.

The archaeosomes may also be formulated to have a defined surface charge, such as but without being limited to a range from about −28 mV to about −49 mV. As an example, the archaeosomes may comprise 6'-sulfate-lactosylarchaeol and uncharged lactosylarchaeol in a mol % ratio of about 50:50, in which case the surface charge of the archaeosome may preferably be from about −25 to about −45 mV.

It may in some instances be desirable to prepare the archaeosomes with a particular diameter, for instance in a range between about 50 nm and about 350 nm. Standard methods for preparing archaeosomes with such dimensions are known, including the use of sonication and filtering techniques, and will be apparent to those of ordinary skill in the art.

Biological Activity

Examples of the archaeosomes prepared as described herein are shown in the Examples to have biological activity, and generate CD8$^+$ and CD4$^+$ T-cell responses.

Without wishing to be bound by theory in any way, the CD8$^+$ T cell response is believed to be due to cross-presentation of antigen (movement of antigen to the cytosol from the phagolysosome of antigen-presenting cells), which is required for cytosolic processing and presentation by MHC class-I molecules to CD8$^+$ T cells. In addition, yet again not wishing to be bound by theory, in view of the observed CD4$^+$ T-cell response it is believed that the antigen chosen from the literature data to be potentially protective antigens for at least one specific type of cancer, i.e. protective peptides for melanoma such as TU.

In addition, this activity in CD8$^+$ and CD4$^+$ T-cells also suggests that archaeosomes comprising the described synthetic charged glycolipids, including the compounds of formula I, may in certain embodiments be useful as adjuvants and vaccines against infectious diseases. For instance, the data presented suggest that the aforementioned archaeosomes may be useful for generating in animals an immune response against any infectious agent or intracellular pathogen where protective peptides or protein antigens are identified, such as but not limited to viral agents, *Mycobacterium tuberculosis* or *Listeria* sp.

Vaccines and pharmaceutical compositions comprising an adjuvant and an antigen are therefore also provided herein, the adjuvant comprising an archaeosome as described above, or a synthetic charged glycolipid such as the compound of formula I. The vaccine or pharmaceutical composition can be used for the promotion of an immune response in a subject, including a protective CD8$^+$ T cell response, a protective CD4$^+$ T cell response, or both. In particular embodiments, the immune response may provide protection against cancer or an infectious agent or pathogen.

The vaccine or composition may be administered by injection, e.g. by intramuscular, intradermal or subcutaneous administration, or by other routes as known in the art.

Methods are provided herein for promoting an immune response in a subject. These methods comprise administering a vaccine or composition as described above in an amount effective to produce an immune response. These methods may include, in certain embodiments and without limitation, methods of treating or preventing cancer, or methods of treating or preventing an infection by an infectious agent or pathogen. The subject or patient involved in such treatment methods may be an animal, including but not limited to cows, pigs, horses, chickens, cats, dogs, fish, etc., and is preferably a mammal, most preferably a human.

Synthesis of Synthetic Charged Glycolipids

A synthetic charged glycolipid as described above may be obtained, generally, by obtaining an archaeal core lipid, such as archaeol, processing the archaeal core lipid to remove any polar head groups (for example, by hydrolysis but not limited thereto) and to covalently link a saccharide group to the free sn-1 hydroxyl group of the glycerol backbone of the archaeal core lipid (e.g. a disaccharide or trisaccharide moiety), thereby producing an uncharged glycolipid, and processing the uncharged glycolipid to add at least one sulfate moiety to the saccharide group. In certain embodiments, yet without wishing to be limiting, the archaeal core lipid may be obtained by isolation from archaeal cells.

In an embodiment, a method is provided for the synthesis of an exemplary yet non-limiting embodiment of a synthetic charged glycolipid or compound of formula I. In particular, a synthesis is provided for the compound (2R)-2,3-Bis[(3R,7R,11R)-3,7,11,15-tetramethylhexadecyloxy]propan-1-yl 4-O-(6-O-sulfo-β-D-galactopyranosyl)-β-D-glucopyranoside, which has the structure:

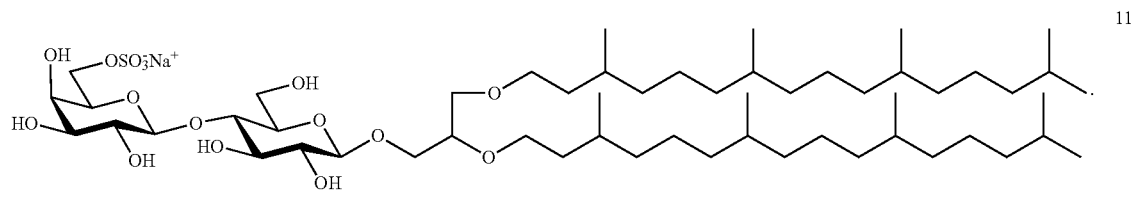

The method comprises:

i) reacting lactose with acetic anhydride and sodium acetate to produce peracetyl-β-D-lactose of formula 1a:

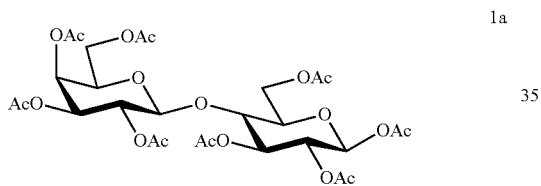

ii) converting the peracetyl-β-D-lactose of formula 1a to a thiophenol glycoside of formula 1b or a thioethyl glycoside of formula 1c:

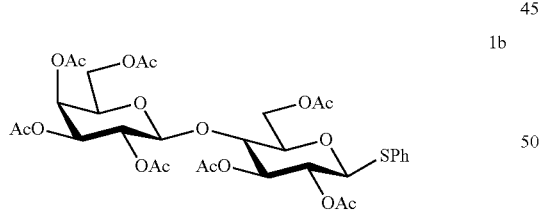

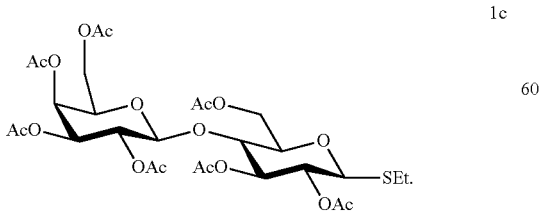

iii) deacetylating the thiophenol glycoside of formula 1b or the thioethyl glycoside of formula 1c followed by benzylidene formation and perbenzoylation to produce a protected thioglycoside of formula 2a or 2b:

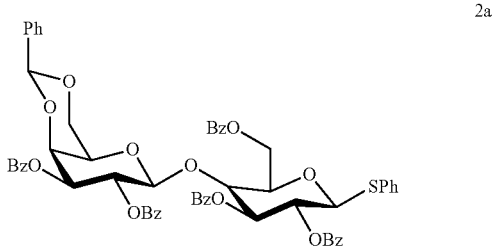

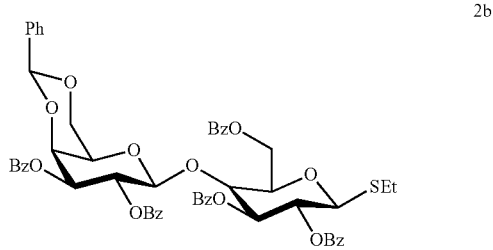

iv) reacting archaeol with the thioglycoside donor of formula 2a or 2b to produce the glycosylated archaeol of formula 4:

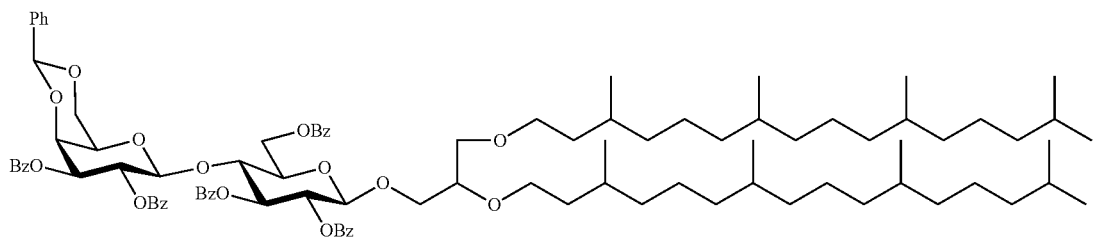

4 v) cleaving the benzylidene of the protected thioglycoside of formula 4 to give a dial of formula 5:

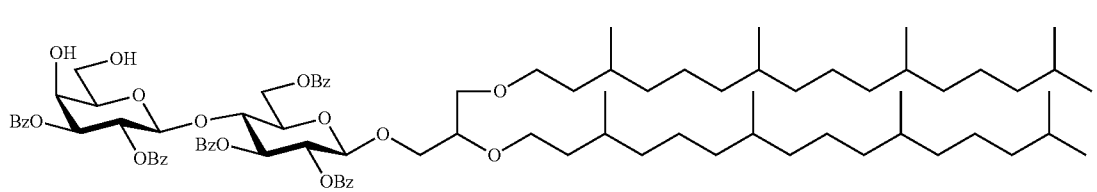

5 vi) regioselectively sulfating on the primary hydroxyl of the disaccharide glycolipid of formula 5 to give a protected sulfated glycolipid of formula 10:

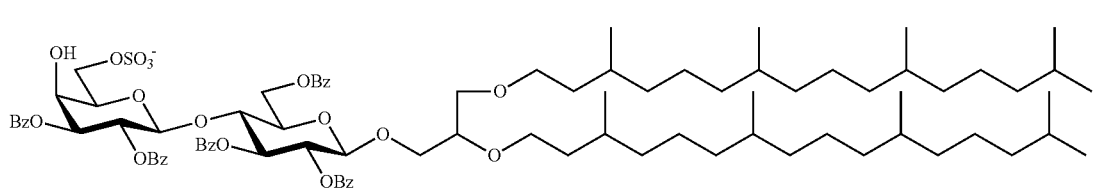

10 and vii) debenzoylating the protected sulfated glycolipid of formula 10 to produce the sulfated glycolipid of formula 11:

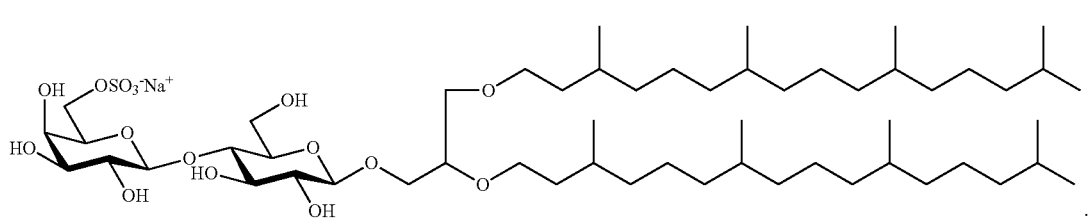

11

Specific embodiments of the above-described method are described in the following Examples.

Method for Preparing Archaeosomes

Methods are also described herein for producing archaeosomes comprising the synthetic charged glycolipid as described above. The method comprises obtaining a synthetic charged glycolipid as described above, such as a compound of formula I, optionally adding at least one additional lipid, optionally adding at least one peptide or protein, and providing conditions for the formation of the archaeosome.

The above method may include, without limitation, the selection and addition of one or more additional lipids to the formulation. These additional lipid(s) may comprise, without limitation, a neutral, or uncharged glycolipid such as a lactosylarchaeol, a rhamnosyl-lactosylarchaeol, a triglucosylarchaeol, monophosphoryl Lipid A, or combinations thereof. The mol % ratio of the synthetic charged glycolipid to the neutral or uncharged lipid may vary from about 100:0 to about 30:70, including all possible ratios within these ranges including without limitation 95:5, 90:10, 80:20, 70:30, 60:40, 55:45, 45:55, 40:60, and 35:65, and is preferably about 50:50.

The method may also include a non-limiting step of adjusting the size of the archaeosomes to a particular diameter, for instance to a size in a range between about 50 nm and about 350 nm.

Other steps and methods for preparing archaeosomes will be apparent to those of ordinary skill in the art, and can be incorporated into the above method as appropriate.

EXAMPLES

Example 1: Preparation of a Sulfated-Glycolipid

Methods:

Archaeol Precursor

The lipid precursor used for synthesis was archaeol obtained from *Halobacterium salinarum* (ATCC 33170) grown aerobically at 37° C. in an all non-animal origin medium developed herein and consisting of: 15 g/L Phytone peptone UF (product 210931 from VWR International); 220 g/L NaCl; 6.5 g/L KCl; 10 g/L $MgSO_4 \cdot 7H_2O$; 10 ml of 0.2 g/100 ml $CaCl_2$; and 10 ml of 0.2 g/100 ml $FeSO_4$. The antifoam agent used was MAZU® DF 204 (BASF Canada). Biomass was harvested from a 20 L to 200 L capacity fermenter after 72 h growth, and frozen. Thawed cell pastes were extracted with chloroform/methanol/water to obtain total lipids according to the protocol of Sprott et al. (Sprott, G. D., Patel, G. B., and Krishnan, L. 2003. *Methods Enzymol.* 373:155-172). The TPL were precipitated from the lipid extract with cold acetone to yield in one example 2.9% of the starting dry wt cells. Typically, 3.5 g TPL was dissolved in 45 ml of chloroform/methanol (2:1, v/v) and 190 ml methanol added. This mixture was cooled to 0° C. in an ice bath, and 10 ml acetyl chloride added drop-wise while being stirred magnetically. Hydrolysis was accomplished by refluxing at 62° C. for 3 h. The mixture was cooled and the volume reduced by rotary evaporation to 100 ml. Upon transfer to a separatory funnel, 12 ml water and 100 ml petroleum ether was added. The mixture was mixed and allowed to separate. The top ether phase containing lipid was pooled with a second ether extraction, and evaporated to dryness.

The archaeol oil obtained above was further purified by silica gel column chromatography. The oil dissolved in a minimum amount of dichloromethane was loaded onto an equilibrated silica gel 60 (ZEOprep 60 HYD 40-63 μm purchased from Canadian Life Science) column (4 cm×38 cm) and archaeol eluted with pressure using hexanes/t-butylmethylether/acetic acid (80/20/0.5, v/v/v). Collected fractions were tested for archaeol by mini thin-layer chromatography using the eluting solvent, and fractions containing pure archaeol pooled and dried. The yield of archaeol from TPL ranged from 43 to 53%. Structural identity and purity of archaeol was confirmed by both NMR spectroscopy and negative-ion fast atom bombardment mass spectrometry.

Analytical Methods

The $^1H$ NMR spectra were obtained on a Varian-400 (400 MHz) or a Bruker AV-III 400 (400 MHz) spectrometer with tetramethylsilane or the residual signal of the solvent as the internal standard. The $^{13}C$ NMR spectra were recorded using a Varian-400 (100 MHz) or a Bruker AV-III 400 (100 MHz) spectrometer using the central line of the solvent signal as reference. In the NMR assignments arch-a to arch-e refer to the carbons or hydrogens indicated in FIG. 1. Assignments for the side chain methylenes arch-d and arch-e can always be interchanged. Sugar rings are numbered with Roman numerals with the reducing end starting at I. $^1H$ and $^{13}C$ NMR were obtained in $CDCl_3$ solution (referenced to residual $CHCl_3$ at 7.26 ppm $^1H$ and 77.0 ppm central resonance $^{13}C$) or were obtained in 1:1 (v:v) solutions of $CD_3OD:CDCl_3$ or $CD_3OD:CD_2Cl_2$ (referenced to residual $CHD_2OD$ at 3.31 ppm $^1H$ and 49.15 ppm central resonance $^{13}C$). Chemical shifts are in ppm and coupling constants in Hz. $^{13}C$ resonances are reported to 1 decimal place except to indicate the separation of closely separated resonances where 2 decimal points are given. Optical rotations were measured at 20° C. in a 1 dm cell on a Perkin-Elmer 343 polarimeter with a Na/Hal lamp at 589 nm. Thin-layer chromatography was performed on precoated plates of silica gel (60-$F_{254}$, E. Merck, Darmstadt) and visualized with $H_2SO_4$—$H_2O$ (1:20 v/v) followed by heating. Unless otherwise stated, flash column chromatography was performed on silica gel 60 (230-400 mesh, Merck). Medium pressure liquid chromatography (MPLC) was performed in self packed glass silica columns with a flow rate of 8-10 mL/min delivered using high performance liquid chromatography pumps. All solvents and reagents were purified and dried according to standard procedures. For example methanol and acetonitrile were dried over activated 3 Å molecular sieve pellets.

Chemical Synthesis

Lactosylarchaeol, archaetidylserine, trimannosylarchaeol, and triglucosylarchaeol were synthesized as reported previously (Whitfield, D. M., Eichler, E. E., and Sprott G. D. 2008. *Carbohydr. Res.* 343:2349-2360; Whitfield, D. M., Yu, S. H., Dicaire, C. J., and Sprott, G. D. 2010. *Carbohydr. Res.* 345:214-229). SLA and RhaLA were synthesized for the first time as described herein.

Known peracetyl-β-D-lactose 1a was synthesized by the well established method of adding lactose in portions to a refluxing mixture of acetic anhydride and sodium acetate (Wolfrom, M. L. and Thompson, A. 1963, in *Methods in Carbohydrate Chemistry*. 2 ed. Academic Press, NY. pp. 211). After purification by precipitation, the solid was converted to the known thiophenol glycoside 1b by the standard thiophenol/$BF_3 \cdot Et_2O$ method (Mehta, S., Gilbert, M., Wakarchuk, W. W., and Whitfield, D. M. 2000. *Org. Lett.* 2:751-753; Purves, C. B. 1929. *J. Am. Chem. Soc.* 51:3619-3627), see Scheme 1. Alternatively the known thioethanol glycoside 1c was made by a similar process (Tomoo, T., Kondo, T., Abe, H., Tsukamoto, S., Isobe, M., Goto, T., 1996. *Carbohydr. Res.* 284: 207-222). Disaccharide donor 1b could be purified by crystallization from ethanol whereas silica gel chromatography was used to purify donor 1c. Conventional Zemplen deacetylation followed by benzylidene formation and perbenzoylation afforded protected thioglycoside 2a in 56% yield for 3 steps. The benzylidene could be cleaved using a two-phase system to give diol acceptor 3 in 57% yield. Alternatively 1c could be converted to 2b by the same sequence of reactions in 69% yield. Disaccharide 2b was easily purified by crystallization (dichloromethane/hexanes) whereas 2a required silica gel purification.

Scheme 1. Synthesis of thio-glycoside building blocks 2a, 2b, and 3.

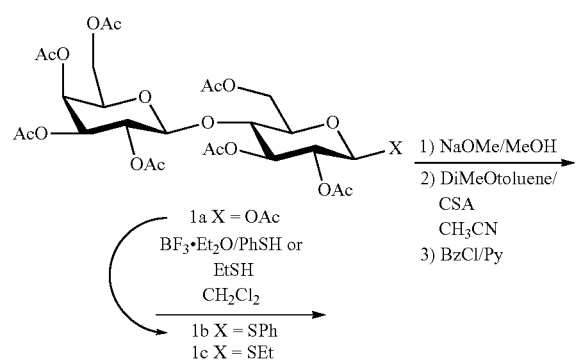

-continued

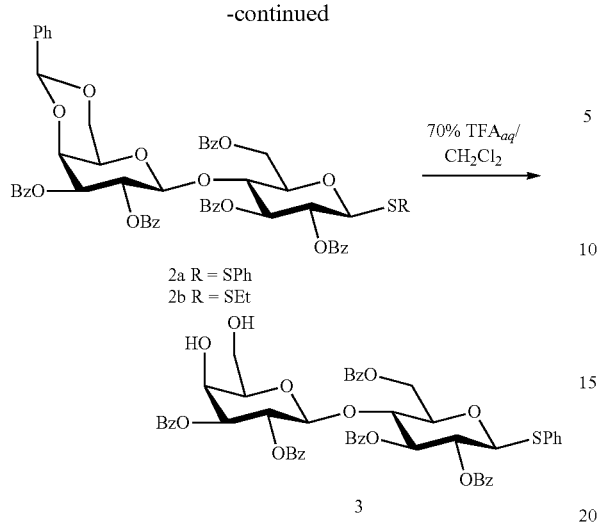

2a R = SPh
2b R = SEt

3

Scheme 2. Synthesis of lactose glycolipid acceptor 5.

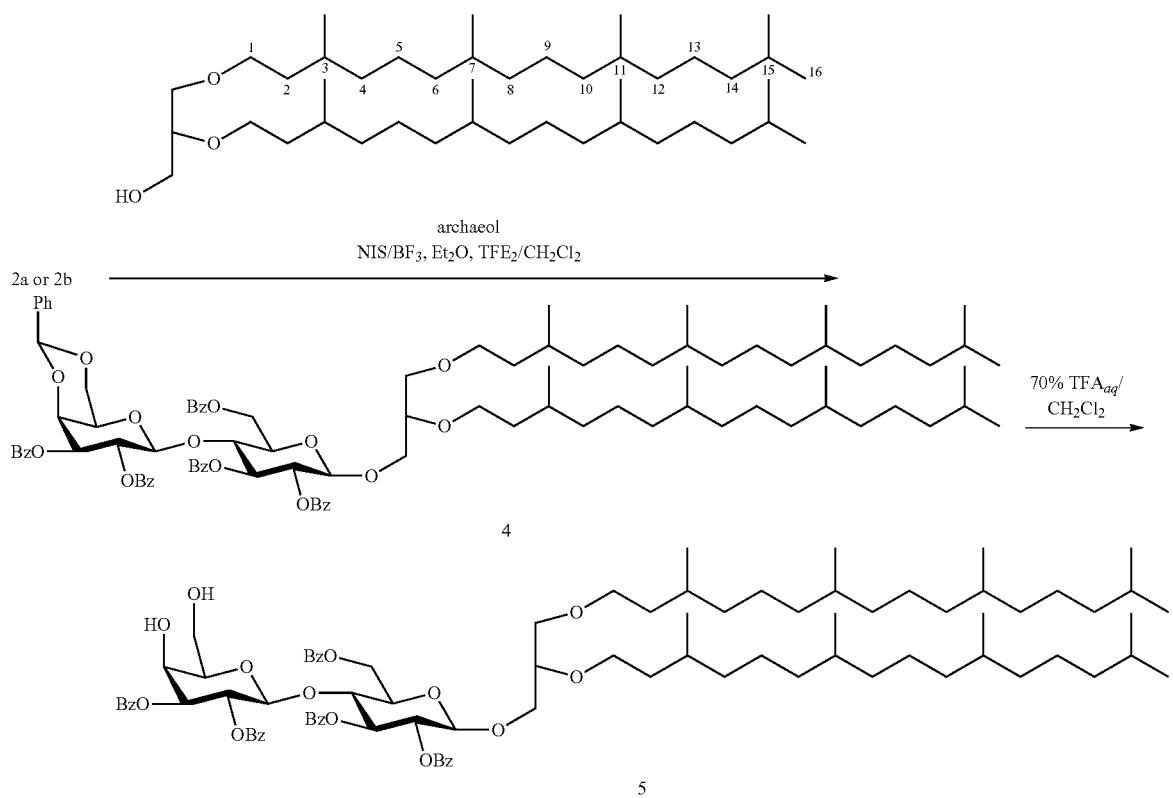

With these building blocks in hand, the lipid archaeol could be glycosylated using the recently developed NIS/BF$_3$.TFE$_2$ method (Whitfield, D. M., Yu, S. H., Dicaire, C. J., and Sprott, G. D. 2010. *Carbohydr. Res.* 345:214-229) in an acceptable 62% yield, see Scheme 2. The benzylidene was cleaved using the same two-phase method as used for 2a to 3 to give acceptor 5 in 85% yield. Acceptor 5 could be glycosylated with rhamnose thiodonor 6a (Auzanneau, F.-I. and Bundle, D. R. 1991. *Carbohydr. Res.* 212:13-24; Douglas, N. L., Ley, S. V., Lucking, U., and, Warriner, S. L. 1998. *J. Chem. Soc.* 1; 51-65; Ray, A. K., Maddali, U. B., Roy, A., and Roy, N. 1990. *Carbohydr. Res.* 197:93-100) to give trisaccharide glycolipid 8, see Scheme 3. Alternatively, 6a could be pre-activated and reacted with acceptor 3 to give trisaccharide donor 7, which could then be reacted with archaeol to give 8 in good yield (82%). The preactivation temperature was difficult to determine and the best yield for 7 was only 13%. At −40° C. the donor partially decomposed whereas at −60° C. the donor was only partially activated. In both cases the acceptor was also partially decomposed under the reaction conditions. Alternatively and giving the best yield was to convert the thioglycoside 6a to its known trichloroacetimidate analogue 6b (Ziegler, T., Bien, F., and Jurisch, C. 1998. *Tetrahedron*: Asymmetry 9: 765-780) and then prepare trisaccharide donor 7 by reacting 6b with acceptor 5.

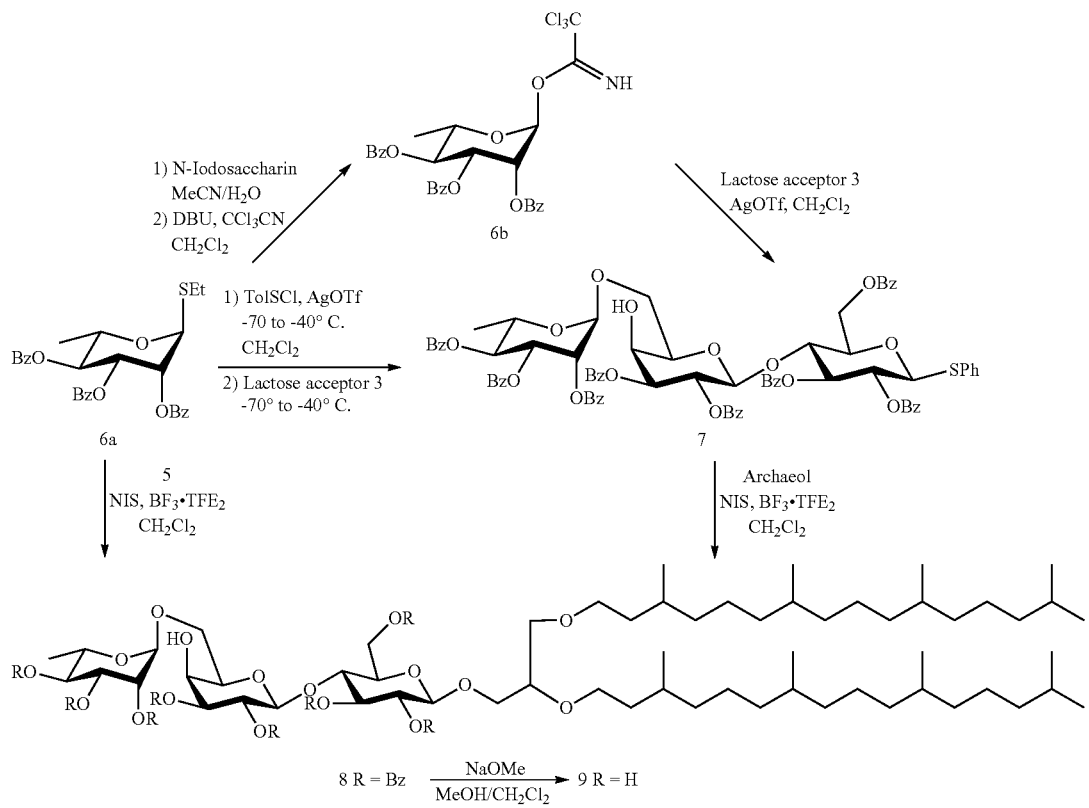

Acceptor 3 could be sulfated regioselectively on the primary hydroxyl to give the protected sulfated glycolipid 10. Zemplen debenzoylation of 10 led to 11 in 54% yield for 2 steps, see Scheme 4.

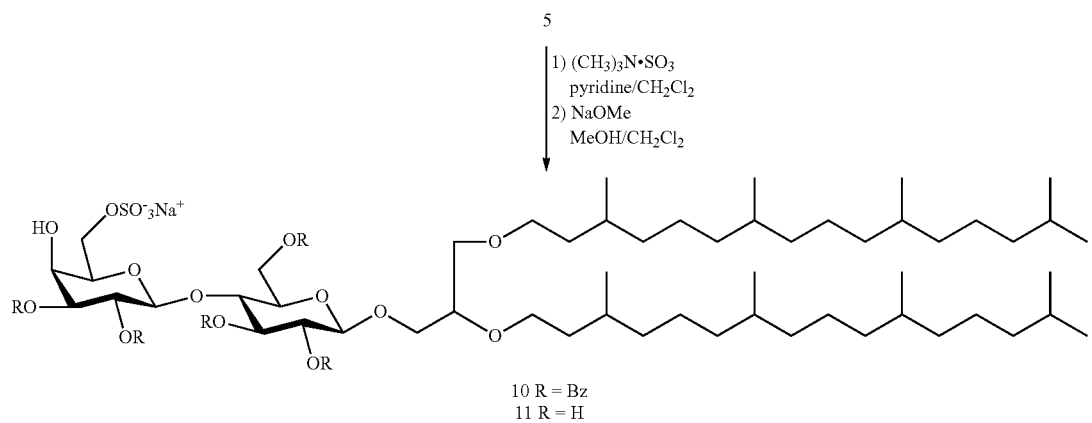

Synthetic Procedures

Phenyl-4-O-(2,3-di-O-benzoyl-4,6-O-benzylidene-β-D-galactopyranosyl)-2,3,6-tri-O-benzoyl-β-D-1-thio-glucopyranoside 2 (Gold, H., Boot, R. G., Aerts, J. M. F. G., Overkleeft, H. S., Codee, J. D. C., and van der Marel, G. A. 2011. *Eur. J. Org. Chem.* 2011:1652-1663).

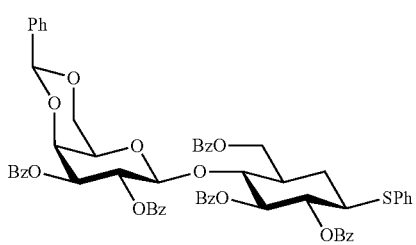

2a

To the known phenyl-4-O-(2,3,4,6-tetra-O-acetyl-β-D-galactopyranosyl)-2,3,6-tri-O-acetyl-β-D-1-thio-glucopyranoside (1b, 4.0 g, 5.5 mmol) with stirring under an atmosphere of argon was added dry methanol (80 mL) followed by 1M sodium methoxide in methanol (9 mL). After stirring for 4 h at room temperature, the mixture was neutralized to about pH 5 with Rexyn 101(H) resin which had been pre-washed with water then methanol. The mixture was filtered by vacuum filtration and evaporated to dryness. Stirring under an atmosphere of argon, dry acetonitrile (80 mL), benzaldehyde dimethylacetal (2.1 mL, 2.5 eq.) and camphor sulfonic acid (128 mg, 0.1 eq) were added sequentially to the residue. During the first hour, the mixture was periodically swirled over the sides of the flask to insure dissolution. At this time and approximately 1 h apart thereafter, the flask was attached to a low pressure vacuum pump (about 10 torr) for approximately 2 min to remove methanol. Stirring after 4 h at room temperature, TLC (30% methanol in ethyl acetate) indicated complete disappearance of starting material. Then triethylamine (0.5 mL) was added followed by solvent evaporation. The residue was redissolved in ethyl acetate (50 mL) and washed with saturated aqueous sodium bicarbonate (50 mL) and brine (50 mL). The aqueous layers were extracted with ethyl acetate (50 mL) and the combined organic layers were dried with sodium sulfate, filtered by vacuum filtration and evaporated to dryness. The residue was dissolved in anhydrous pyridine (36 mL) followed by addition of benzoyl chloride (3.8 mL, 6 eq.). Sealed under an atmosphere of argon, the mixture was stirred at room temperature overnight. Methanol (0.5 mL) was then added followed by solvent evaporation. Crystallization from dichloromethane/petroleum ether only isolated a water-soluble by-product. The mother liquor was concentrated and then purified by silica gel flash chromatography eluting with 4:6 hexanes/dichloromethane, 0.25:1.75:3 then 0.5:1.5:3 ethyl acetate/hexanes/dichloromethane to yield a waxy solid (2a, 3.2 g, 56% overall).

$[\alpha]_D$ 94.7° (c, 0.006, CHCl$_3$); $^1$H NMR CDCl$_3$: δ 7.98-7.87 (m, 10H, Bz$_o$), 7.60 (t, 1H, J=7.4, Bz$_p$), 7.52 (t, 1H, J=7.5, Bz$_p$), 7.50-7.28 (m, 18H, Bz$_p$, Bz$_m$, Benz$_o$, Benz$_m$, Benz$_p$, SPh$_m$), 7.18 (m, 3H, Bz$_m$, SPh$_p$), 7.05 (brt, 2H, J=7.6, SPh$_o$), 5.85 (brt, 1H, J$_{3,4}$=9.1, H-3$^I$), 5.78 (dd, J$_{2,3}$=10.3, H-2$^{II}$), 5.31 (brt, 1H, J$_{2,3}$=9.6, H-2$^I$), 5.28 (s, 1H, BenzCHO$_2$), 5.17 (dd, 1H, J$_{3,4}$=3.3, H-3$^{II}$), 4.92 (d, 1H, J$_{1,2}$=10.2, H-1$^I$), 4.84 (d, 1H, J$_{1,2}$=8.0, H-1$^{II}$), 4.67 (brd, 1H, J$_{66'}$=12.0, H-6$^I$), 4.40 (dd, 1H, J$_{56'}$=4.9, H-6$^{\prime I}$), 4.31 (brd, 1H, H-4$^{II}$), 4.14 (brt, 1H, J$_{4,5}$=9.5, H-4$^I$), 3.90 (m, 1H, H-5$^I$), 3.72 (brd, 1H, J$_{6,6'}$=12.3, H-6$^{II}$), 3.58 (brd, 1H, H-6$^{\prime II}$), 3.00 (brs, 1H, H-5$^{II}$); $^{13}$C NMR CDCl$_3$: δ 166.1, 165.6, 165.3, 165.0, 164.9 (5×BzC=O), 137.4 (Benz$_{ip}$), 133.3-133.1 (Bz$_p$), 131.6 (SPh$_{ip}$), 129.9-127.9 (Bz$_o$, Bz$_m$, Bz$_{ip}$, Benz$_m$, Benz$_p$, SPh$_o$, SPh$_m$, SPh$_p$), 126.4 (Benz$_o$), 101.5 (C-1$^{II}$), 100.6 (BenzCHO$_2$), 85.6 (C-1$^I$), 76.8 (C-4$^I$, C-5$^I$), 75.0 (C-3$^I$), 73.0 (C-4$^{II}$), 72.6 (C-3$^{II}$), 70.8 (C-2$^I$), 69.5 (C-2$^{II}$), 67.9 (C-6$^{II}$), 66.5 (C-5$^{II}$), 62.6 (C-6$^I$); HRMS Obs. 1060.3057, calcd. C$_{60}$H$_{54}$S$_1$O$_{15}$N$_1$ (M+NH$_4$)$^+$ 1060.3213.

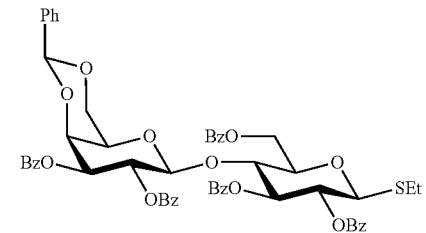

2b

Lactose octaacetate (10 g, 15 mmol) was dried under high vacuum overnight at room temperature, dissolved in anhydrous dichloromethane (30 mL), cooled to 0° C. followed by addition of ethanethiol (2.2 mL, 30 mmol) and boron trifluoride diethyl etherate (9.2 mL, 75 mmol). The stirring was continued at 0° C. under Ar for 2 h. The reaction was quenched by adding saturated aqueous sodium bicarbonate (50 mL) followed by addition of solid sodium bicarbonate in small portions over 1 h until no more extensive effervescence. Phase separation was done in a reparatory funnel and the bottom organic phase was washed with saturated aqueous sodium bicarbonate (2×50 mL) then water (4×50 mL) and was dried with sodium sulfate, filtered and concentrated. Silica gel flash chromatography (dry loading) started with 5:4:1 then 4:5:1 and finally 3:6:1 hexanes/ethyl acetate/dichloromethane yielded the thioglycoside (1b, 8.8 g, 88%), Then, thioglycoside (1b, 8.8 g, 13 mmol) was dissolved in anhydrous methanol (150 mL) followed by addition of 1 M methanolic sodium methoxide (20 mL), Stirring continued at room temperature under Ar for 4 h and the reaction was quenched by adding water-methanol washed Rexyn 101(H) resin until acidic pH (~5). The deacetylated thioglycoside was isolated by vacuum filtration, solvent removal and high vacuum drying overnight. With the help of sonication, the crude product from above (4.9 g) was suspended in anhydrous acetonitrile (170 mL) followed by addition of benzaldehyde dimethylacetal (4.8 mL, 2.5 eq.) and camphor sulfonic acid (296 mg, 0.1 eq). Stirring continued at room temperature under Ar and during the first hour, the mixture was periodically swirled over the sides of the flask. The mixture slowly became clearer but eventually a white precipitate appeared. At this time and approximately 1 h apart thereafter, the flask was attached to a low pressure vacuum pump (about 10 torr) for approximately 2 min to remove methanol. Stirring after 4 h in total, TLC (30% methanol in ethyl acetate) indicated complete disappearance of the starting material. Triethylamine (1.2 mL) was then added followed by solvent evaporation. The residue was transferred into a separatory funnel using water and ethyl acetate. Upon phase separation, the bottom aqueous phase was washed with ethyl acetate twice followed by concentration, toluene co-evaporation (×3) and high-vacuum drying over the weekend. The residue (5.1 g) was dissolved in anhydrous pyridine (80 mL) followed by addition of benzoyl chloride (7.5 mL, 6 eq.). Sealed under an atmosphere of argon, the mixture was stirred at room temperature overnight. Methanol (2 mL) was then added followed by solvent removal, toluene co-evaporation (×3) and high-vacuum drying for 2 h. The residue was then redissolved in dichloromethane (80 mL) followed by saturated aqueous sodium bicarbonate wash (3×30 mL) then water wash (3×30 mL) in a separatory funnel. The organic phase was dried with sodium sulfate, filtered and concentrated. Recrystallization was carried out by first dissolving the residue in minimum amount of dichloromethane followed by addition of hexanes until cloudiness disappeared only upon heating yielded the protected thioglycoside as a white solid (2b, 8.4 g, 78%, 69% overall).

$[\alpha]_D$ 111.0° (c, 0.0228, CH$_2$Cl$_2$), $^1$H NMR CD$_2$Cl$_2$: δ 8.02 (brd, 2H, J=8.5, Bz$_o$), 7.93 (brd, 2H, J=7.0, Bz$_o$), 7.92 (brd, 2H, J=7.1, Bz$_o$), 7.89 (brd, 2H, J=7.1, Bz$_o$), 7.85 (brd, 2H, J=8.5, Bz$_o$), 7.52 (t, 1H, J=7.5, Bz$_p$), 7.49-7.22 (m, 17H, Bz$_p$, Bz$_m$, Benz$_o$, Benz$_p$), 7.20 (brt, 2H, J=7.5, Benz$_m$), 5.84 (brt, 1H, J$_{3,4}$=9.1, H-3$^I$), 5.68 (dd, J$_{2,3}$=10.5, H-2$^{II}$), 5.35 (brt, 1H, J$_{2,3}$=9.6, H-2$^I$), 5.32 (s, 1H, BenzCHO$_2$), 5.21 (dd, 1H, J$_{3,4}$=3.6, H-3$^{II}$), 4.90 (d, 1H, J$_{1,2}$=8.0, H-1$^{II}$), 4.77 (d, 1H, J$_{1,2}$=10.0, H-1$^I$), 4.61 (dd, 1H, J$_{5,6}$=2.0, J$_{66'}$=12.0, H-6$^I$), 4.35 (brd, 1H, H-4$^{II}$), 4.34 (dd, 1H, J$_{56'}$=4.9, H-6$^{II}$), 4.26 (brt, 1H, J$_{4,5}$=9.5, H-4$^I$), 3.85 (ddd, 1H, H-5$^I$), 3.69 (dd, 1H, J5,6=1.1, J$_{6,6'}$=12.3, H-6$^{II}$), 3.60 (dd, 1H, J$_{5,6'}$=1.6, H-6$^{III}$), 3.05 (brs, 1H, H-5$^{II}$); 2.62 (m, 2H, CH$_2$S), 1.13 (t, 3H, J=7.4, (m, 2H, CH$_3$CH$_2$S); $^{13}$C NMR CD$_2$Cl$_2$: δ 166.3, 166.1, 165.8, 165.7, 165.5 (5×BzC=O), 138.2 (Benz$_{ip}$), 133.89, 133.85, 133.77, 133.75, 133.6 (5×Bz$_p$), 130.3, 130.18, 130.16, 130.11, 130.09 (5×Bz$_o$), 129.9, 129.7, 129.5, 129.4 (Bz$_{ip}$), 129.1, 128.96, 128.95, 128.9, 128.6 (Benz$_m$, Benz$_p$, Bz$_m$), 126.8 (Benz$_o$), 102.1 (C-1$^{II}$), 101.1 (BenzCHO$_2$), 84.1 (C-1$^I$), 77.6 (C-4$^I$), 77.3 (C-5$^I$), 75.7 (C-3$^I$), 73.8 (C-4$^{II}$), 73.1 (C-3$^{II}$), 71.7 (C-2$^I$), 70.1 (C-2$^{II}$), 68.5 (C-6$^{II}$), 67.1 (C-5$^{II}$), 63.1 (C-6$^I$); 25.0 (CH$_2$S), CH$_3$CH$_2$S); HRMS Obs. 1017.2804, calcd. C$_{56}$H$_{50}$S$_1$O$_{15}$Na$_1$ (M+Na)$^+$ 1017.2763.

Phenyl-4-O-(2,3-di-O-benzoyl-β-D-galactopyranosyl)-2,3,6-tri-O-benzoyl-β-D-1-thio-glucopyranoside
3

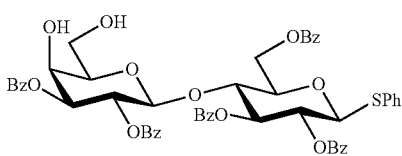

4,6-Benzylidene (2a, 2.4 g, 23 mmol) was dissolved in dichloromethane (90 mL) and cooled in an ice bath under an atmosphere of argon with stirring. To this was added precooled (0° C.) 70% aqueous trifluoroacetic acid (30 mL). The reaction was monitored by TLC (5% isopropanol/dichloromethane) until complete disappearance of starting materials, typically 2 to 4 h. The reaction was diluted with water (about 50 mL) and transferred to a separatory funnel with further rinsing with dichloromethane, water and dichloromethane sequentially. The layers were separated and the organic phase was washed with saturated aqueous sodium bicarbonate (3×100 mL). The organic layer was then dried with sodium sulfate, filtered by gravity and evaporated to dryness. The residue was purified by MPLC with loading in dichloromethane and elution with first 2% then 3% isopropanol/dichloromethane to yield a waxy solid (3, 1.3 g, 57%).

$[\alpha]_D$ 64.9° (c, 0.0033, CHCl$_3$); $^1$H NMR CDCl$_3$: δ 7.99 (brd, 2H, J=7.7, B$_o$), 7.92 (m, 8H, Bz$_o$), 7.62 (t, 1H, J=7.3, Bz$_p$), 7.56-7.29 (m, 14H, Bz$_p$, Bz$_m$, SPh$_m$), 7.20 (m, 3H, Bz$_m$, SPh$_p$), 7.07 (brt, 2H, J=73, SPh$_o$), 5.74 (m, H-3$^I$, H-2$^{II}$), 5.39 (brt, 1H, J$_{2,3}$=9.3, H-2$^I$), 5.09 (dd, 1H, J$_{2,3}$=10.2, J$_{3,4}$=3.3, H-3$^{II}$), 4.91 (d, 1H, J$_{1,2}$=10.0, H-1$^I$), 4.78 (d, 1H, J$_{1,2}$=7.6, H-1$^{II}$), 4.65 (brd, 1H, J$_{66'}$=11.9, H-6$^I$), 4.43 (dd, 1H, J$_{56}$=5.7, H-6$^{'I}$), 4.19 (brd, 1H, H-4$^{II}$), 4.11 (brt, 1H, J$_{4,5}$=9.4, H-4$^I$), 3.92 (m, 1H, H-5$^I$), 3.37 (m, 2H, H-6$^{II}$, H-5$^{II}$), 3.27 (m, 1H, H-6$^{'II}$), 1.19 (brs, 1H, OH); $^{13}$C NMR CDCl$_3$: δ 165.83, 165.76, 165.4, 165.2, 165.0 (5×BzC=O), 133.5, 133.34, 133.27, 133.2, 133.0 (5×Bz$_p$), 131.8 (SPh$_{ip}$), 129.9-128.4 (Bz$_o$, Bz$_m$, Bz$_{ip}$, SPh$_m$, SPh$_p$), 126.4 (SPh$_o$), 101.2 (C-1$^{II}$), 85.8 (C-1$^I$), 76.9 (C-5$^I$), 74.2 (C-4$^I$), 74.5 (C-3$^I$), 74.2 (C-5$^{II}$), 74.1 (C-3$^{II}$), 70.4 (C-2$^I$), 69.7 (C-2$^{II}$), 68.4 (C-4$^{II}$), 52.9 (C-6$^I$), 62.5 (C-6$^{II}$); HRMS Obs. 972.2900, calcd. C$_{53}$H$_{50}$S$_1$O$_{15}$N$_1$ (M+NH$_4$)$^+$ 972.2830.

Phenyl 6-O-(2,3,4-tri-O-benzoyl-α-L-rhamnopyranosyl)-4-O-(2,3-di-O-benzoyl-β-D-galactopyranosyl)-2,3,6-tri-O-benzoyl-β-D-1-thio-glucopyranoside
7

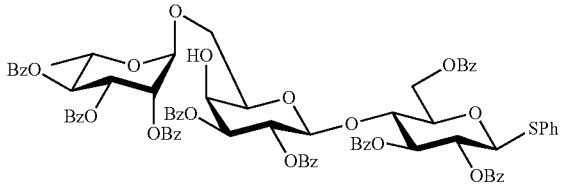

Known ethyl 2,3,4-tri-O-benzoyl-α-L-1-thio-rhamnopyranoside (6a, 174 mg, 0.33 mmol) was dissolved in dichloromethane (1.5 mL) in the presence of activated powdered 3 Å molecular sieves (about 200 mg). Stirring under an atmosphere of argon and cooled to −60° C., silver trifluoromethanesulfonate (92 mg, 0.35 mmol) was added followed by p-toluylsulfenyl chloride (Barrett, A. G. M., Dhanak, D., Graboski, G. G., and Tayler, S. J. 1993. Org. Syn. Coll. 8:550; Huang, X., Huang, L., Wang, H., and Ye, X. S. 2004. Angew. Chem. Int. Ed Engl. 43:5221-5224) (55 μL, 0.37 mmol). After stirring for 1 h at −60° C., acceptor (3, 212 mg, 0.22 mmol) dissolved in dichloromethane (1.5 mL) was added dropwise to the preactivated mixture, After further stirring for 1 h at −60° C., the reaction was quenched by the addition of saturated aqueous sodium bicarbonate (5 mL) followed by aqueous 10% sodium thiosulfate (5 mL) and dichloromethane (5 mL). The mixture was then transferred to a separatory funnel with rinsing with dichloromethane. The bottom organic layers were separated, dried with sodium sulfate, filtered by gravity and evaporated to dryness. The residue was purified by flash chromatography eluting with 8:1:1 hexanes/ethyl acetate/dichloromethane to yield a waxy solid (7, 40 mg, 13%).

$[\alpha]_D$ 85.6° (c, 0.0059, CH$_2$Cl$_2$); $^1$H NMR CDCl$_3$: δ 8.14 (d, 2H, J=8.0, Bz$_o$), 8.01 (d, 2H, J=7.0, Bz$_o$), 7.93 (m, 10H, Bz$_o$), 7.80 (d, 2H, J=7.3, Bz$_o$), 7.66-7.15 (m, 27H, Bz$_m$, Bz$_p$, SPh$_m$, SPh$_p$), 7.08 (t, 2H, J=7.6, SPh$_o$), 5.75 (brt, J$_{3,4}$=9.9, H-3$^I$), 5.70 (brt, 1H, J$_{2,3}$=9.9, H-2$^{II}$), 5.60 (m, 2H, H-3$^{III}$, H-4$^{III}$), 5.49 (m, 1H, H-2$^{III}$), 5.38 (brt, 1H, J$_{2,3}$=9.7, H-2$^I$), 5.29 (dd, J$_{3,4}$=2.9, H-3$^{II}$), 4.94 (d, 1H, J$_{1,2}$=10.0, H-1$^I$), 4.83 (d, 1H, J$_{1,2}$=7.9, H-1$^{II}$), 4.65 (brs, 1H, H-1$^{III}$), 4.62 (brd, H, J$_{66'}$=12.0, H-6$^I$), 4.44 (dd, 1H, J$_{5,6'}$=5.3, H-6$^{'I}$), 4.21 (brd, 1H, J$_{3,4}$=2.9, H-4$^{II}$), 4.14 (brt, 1H, J$_{4,5}$=9.4, H-4$^I$), 4.00 (m, 1H, H-5$^{III}$), 3.89 (ddd, 1H, J$_{5,6}$~1, H-5$^I$), 3.58 (m, 1H, H-5$^{II}$), 3.43 (brt, 1H, J$_{5,6}$=9.4, H-6$^{II}$), 2.92 (dd, 1H, J$_{6,6'}$=9.6, J$_{5,6'}$=6.0, H6$^{III}$), 1.24 (d, 3H, J$_{5,6}$=6.7, CH$_3$$^{III}$); $^{13}$C NMR CDCl$_3$: δ 165.8, 165.7, 165.47, 165.45, 165.4, 165.3, 165.2, 165.1 (8×BzC=O), 133.5-133.0 (Bz$_p$), 131.8 (SPh$_p$), 130.0-128.1 (Bz$_m$, Bz$_o$, Bz$_{ip}$, SPh$_m$, SPh$_o$, SPh$_{ip}$), 101.5 (C-1$^{II}$), 97.4 (C-1$^{III}$), 85.7 (C-1$^I$), 77.2 (C-5$^I$), 76.6 (C-4$^I$), 74.7 (C-3$^I$), 73.8 (C-3$^{II}$), 72.6 (C-5$^{II}$), 71.6 (C-4$^{III}$), 70.6 (C-2$^{III}$), 70.5 (C-2$^I$), 70.0 (C-2$^{II}$), 69.8 (C-3$^{III}$), 66.6 (C-4$^{II}$), 64.2 (C-6$^{II}$), 62.6 (C-6$^I$), 17.6 (C-6$^{III}$); HRMS Obs. 1435.3821, calcd. C$_{80}$H$_{68}$O$_{22}$S$_1$Na$_1$ (M+Na)$^+$ 1435.4073.

Alternative Synthesis of 7.

Thioglycoside (6a, 1 g 1.9 mmol) was dissolved in acetonitrile (4.5 mL) and water (0.5 mL). To this solution was added N-iodosaccharin (890 mg, 1.5 eq.) and the stirring continued until complete disappearance of the starting material in about 2 h (Mandal, P. K. and Misra, A. K. 2007. *SYNLETT.* 8:1207-1210). The reaction was evaporated to dryness at high vacuum and the residue was purified by chromatography eluting first with 8:1:1 followed by 7:2:1 hexanes/ethyl acetate/dichloromethane. The product (660 mg) dissolved in dichloromethane (5 mL) and trichloroacetonitrile (0.95 mL, 5 eq.) was added followed by DBU (28 μL, 0.1 eq). The reaction was cooled in an ice bath and was stirred under an atmosphere of argon until complete disappearance of starting materials by TLC (7:2:1 hexanes/ethyl acetate/dichloromethane), typically 2 h. The reaction was then evaporated to dryness and the residue purified by chromatography eluting first with 8:1:1 followed by 7:2:1 hexanes/ethyl acetate/dichloromethane to yield 6b (734 mg, 75% from 6a). Then under an atmosphere of argon, lactose diol (3, 564 mg, 0.59 mmol) and 6b (334 mg, 1.1 eq) were dissolved in dichloromethane (5 mL) with the reaction flask cooled in an ice bath. Silver trifluoromethanesulfonate (152 mg, 1.0 eq.) was added as a solid quickly. After 45 min TLC indicated complete disappearance of the starting materials. The reaction was quenched with an aqueous mixture of sodium bicarbonate and sodium thiosulfate. The contents of the flask were transferred to a separatory funnel with rinsing with water and dichloromethane. The bottom organic layer was separated, dried with sodium sulfate, filtered by gravity with rinsing with dichloromethane followed by evaporation. The residue was purified by flash chromatography eluting with 7:2:1 hexanes/ethyl acetate/dichloromethane to yield two fractions, one pure (7, 377 mg, 45%) and one slightly impure. The impure fraction was further purified by MPLC eluting with 8:1:1 hexanes/ethyl acetate/dichloromethane to yield more 7 (21%) as a white powder.

(2R)-2,3-Bis[(3R,7R,11R)-3,7,11,15-tetramethyl-hexadecyloxy]propan-1-yl 4-O-(2,3-di-O-benzoyl-4,6-O-benzylidene-β-D-galactopyranosyl)-2,3,6-tri-O-benzoyl-β-D-glucopyranoside 4

Donor (2, 271 mg, 0.26 mmol) and archaeol (113 mg, 0.17 mmol) were dried together for 16 h at high vacuum. Then activated powdered 3 Å molecular sieves (about 500 mg) followed by dry dichloromethane (4 mL) were added and the mixture was stirred under an atmosphere of argon at room temperature for 45 min. N-iodosuccinimide (97 mg, 2.5 eq.) followed by a 0.25 M (with respect to boron) dichloromethane solution of BF$_3$.Et$_2$O/trifluoroethanol (1:2) (690 μL, 1 eq) were added (Whitfield, D. M., Yu, S. H., Dicaire, C. J., and Sprott G. D. 2010. *Carbohydr. Res.* 345:214-229). After 1 h, saturated aqueous sodium bicarbonate (about 15 mL) followed by 10% aqueous sodium thiosulfate (about 15 mL) and dichloromethane (about 10 mL) were added. Stirring was continued until the red color completely disappeared and the mixture was transferred into a separatory funnel with rinsing with water and dichloromethane. The lower organic layer was separated, dried over sodium sulfate, filtered by gravity and evaporated to dryness. The residue was purified by flash chromatography eluting with first 8:1:1 followed by 7:2:1 hexanes/ethyl acetate/dichloromethane to yield a viscous oil (4, 168 mg; 62%).

[α]$_D$ 68.9° (c, 0.015, CHCl$_3$); $^1$H NMR CDCl$_3$: δ 8.00 (d, 2H, J=7.6, Bz$_o$), 7.94 (d, 2H, J=7.9, Bz$_o$), 7.90 (m, 6H, Bz$_o$), 7.57 (t, 1H, J=7.3, Bz$_p$), 7.46 (m, 5H, Bz$_p$, Benz$_p$), 7.32 (m, 12H, Bz$_m$, Benz$_o$, Benz$_m$), 7.17 (brt, 2H, J=7.6, Bz$_m$), 5.85 (brt, 1H, J$_{3,4}$=9.1, H-3$^I$), 5.80 (dd, J$_{2,3}$=10.5, H-2$^{II}$), 5.36 (brt, 1H, J$_{2,3}$=9.5, H-2$^I$), 5.29 (s, 1H, BenzCHO$_2$), 5.17 (dd, 1H, J$_{3,4}$=2.9, H-3$^{II}$), 4.85 (d, 1H, J$_{1,2}$=7.9, H-1$^{II}$), 4.77 (d, 1H, J$_{1,2}$=7.9, H-1$^I$), 4.63 (brd, 1H, J$_{66'}$=12.0, H-6$^I$), 4.38 (dd, 1H, J$_{56'}$=3.8, H-6$^{II}$), 4.31 (brd, 1H, H-4$^{II}$), 4.23 (brt, 1H, J$_{4,5}$=9.9, H- 4$^I$), 3.85 (m, 2H, CHH-arch-a, H-5$^I$), 3.78 (brd, 1H, J$_{6,6'}$=12.0, H-6$^{II}$), 3.58 (brd, 1H, H-6'$_{II}$), 3.51 (m, 2H CHH-arch-a, CH-arch-b), 3.35 (m, 2H, CH$_2$-arch-d), 3.27 (m, 4H, CH$_2$-arch-c, CH$_2$-arch-e), 2.98 (brs, 1H, H-5$^{II}$), 1.60-1.40 (m, 4H, arch-CH, CH$_2$), 1.40-1.06 (m, 44H, arch-CH, CH$_2$), 0.88-0.82 (m, 24H, arch-CH$_3$), 0.79 (d, 3H, J=6.6, arch-CH$_3$), 0.70 (d, 3H, J=6.6, arch-CH$_3$); $^{13}$C NMR CDCl$_3$: δ 166.1, 165.6, 165.2, 165.0, 164.8 (5×BzC=O), 137.4 (Benz$_{ip}$), 133.3, 133.06, 133.04, 133.0, 132.9 (5×Bz$_p$), 129.8-127.9 (Bz$_o$, Bz$_m$, Bz$_{ip}$, Benz$_m$, Benz$_p$), 126.3 (Benz$_o$), 101.4 (C-1$^{II}$), 101.0 (C-1$^I$), 100.6 (BenzCHO$_2$), 77.6 (CH-arch-b), 76.7 (C-4$^I$), 74.0 (C-3$^I$), 73.0 (C-4$^{II}$), 72.7 (C-5$^I$), 72.6 (C-3$^{II}$), 72.3 (C-2$^I$), 70.5 (CH$_2$, arch- c), 70.4 (CH$_2$, arch-a), 69.9 (C-2$^{II}$), 69.4 (CH$_2$, arch-d), 69.0 (CH$_2$, arch-e), 67.9 (C-6$^{II}$), 66.4 (C-5$^{II}$) 62.3 (C-6$^I$), 39.3, 37.48, 37.44, 37.42, 37.38, 37.34, 37.26, 36.9, 36.5 (CH$_2$-arch), 32.8, 29.8, 29.6, 27.9 (CH, arch), 24.8, 24.5, 24.29, 24.26 (CH$_2$, arch), 22.7, 22.6, 19.7, 19.6, 19.5 (CH$_3$, arch); HRMS Obs. 1607.9286, calcd. C$_{97}$H$_{132}$O$_{18}$Na$_1$ (M+Na)$^+$ 1607.9306.

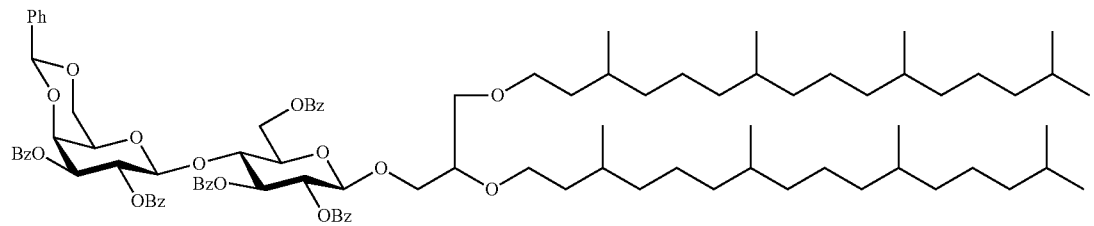

4

(2R)-2,3-Bis[(3R,7R,11R)-3,7,11,15-tetramethyl-hexadecyloxy]propan-1-yl 4-O-(2,3-di-O-benzoyl-β-D-galactopyranosyl)-2,3,6-tri-O-benzoyl-β-D-glucopyranoside 5

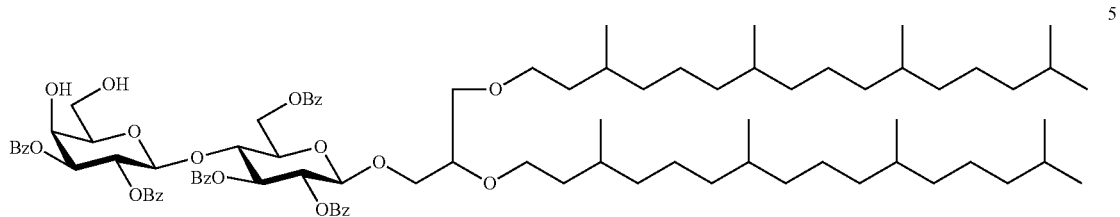

4,6-Benzylidene (4, 571 mg, 0.36 mmol) was dissolved in dichloromethane (20 mL) and cooled in an ice bath under an atmosphere of argon with stirring. To this was added pre-cooled (0° C.) 70% aqueous trifluoroacetic acid (15 mL). The reaction was monitored by TLC (6:3:1 hexanes/ethyl acetate/dichloromethane) until complete disappearance of starting materials, typically 3.5 h. The reaction was then diluted with water (about 50 mL) and transferred to a separatory funnel with further rinsing with dichloromethane, water and dichloromethane sequentially. The layers were separated and the organic phase was washed with saturated aqueous sodium bicarbonate (2×100 mL), Then the organic layer was dried with sodium sulfate, filtered by gravity and evaporated to dryness. The residue was purified by flash chromatography eluting with 7:2:1 hexanes/ethyl acetate/dichloromethane to yield a waxy solid (5, 457 mg, 85%). A small amount of the starting material (4, 83 mg, 14%) was also recovered.

$[\alpha]_D$ 41.9° (c, 0.0181, CHCl$_3$); $^1$H NMR CDCl$_3$: δ 8.07, 7.96, 7.94, 7.92, 7.90 (5×d, 10H, J=7.6, Bz$_o$), 7.58, 7.54 (brt, 2H, J=7.6, Bz$_p$), 7.49-7.30 (m, 11H, Bz$_p$, Bz$_m$), 7.23 (brt, 2H, J=7.6, Bz$_m$), 5.73 (brt, 2H, H-3$^I$, H-2$^{II}$), 5.43 (brt, 1H, J$_{2,3}$=8.8, H-2$^I$), 5.07 (dd, 1H, J$_{2,3}$=10.6, J$_{3,4}$=2.9, H-3$^{II}$), 4.77 (d, 1H, J$_{1,2}$=7.4, H-1$^{II}$), 4.76 (d, 1H, J$_{1,2}$=8.0, H-1$^I$), 4.59 (brd, 1H, J$_{66'}$=11.7, H-6$^I$), 4.42 (dd, 1H, J$_{56'}$=4.1, H-6$^{'I}$), 4.18 (m, 2H, H-4$^{II}$, H-4$^I$), 3.85 (m, 2H, CHH-arch- a, H-5$^I$), 3.49 (m, 2H CHH-arch-a, CH-arch-b), 3.35 (m, 4H, CH$_2$-arch-c, CH$_2$-arch-d), 3.26 (m, 5H, CH$_2$-arch-e, H-5$^{II}$, H-6$^{II}$, H6$^{'II}$), 1.52-1.36 (m, 6H, arch-CH, CH$_2$), 1.41-1.04 (m, 42H, arch-CH, CH$_2$), 0.90-0.70 (m, 30H, arch-CH$_3$); $^{13}$C NMR CDCl$_3$: δ 165.83, 165.76, 165.5, 165.2, 165.1 (5×BzC=O), 133.4, 133.3, 133.19, 133.17, 133.1 (5×Bz$_p$), 129.8-128.3 (Bz$_o$, Bz$_m$, Bz$_{ip}$), 101.3 (C-1$^{II}$), 101.0 (C-1$^I$), 77.6 (CH-arch-b), 76.5 (C-4$^I$), 74.3 (C-3$^{II}$), 74.2 (C-5$^{II}$), 73.6 (C-3$^I$), 72.8 (C-5$^I$), 71.8 (C-2$^I$), 70.5 (2×CH$_2$, arch-a, arch-d), 69.9 (CH$_2$, arch-e), 69.7 (C-2$^{II}$), 69.1 (CH$_2$, arch-c), 68.0 (C-4$^{II}$), 62.6 (C-6$^I$), 62.3 (C-6$^{II}$), 39.3, 37.48, 37.39, 37.35, 37.27, 36.9, 36.5 (CH$_2$-arch), 32.8, 29.9, 29.6 (CH, arch), 24.8, 24.5, 24.30, 24.26 (CH$_2$, arch), 22.7, 22.6, 19.7, 19.6, 19.5 (CH$_3$, arch); HRMS Obs. 1515.0216, calcd. C$_{90}$H$_{132}$O$_{18}$N$_1$ (M+NH$_4$)$^+$ 1514.9443.

(2R)-2,3-Bis[(3R,7R,11R)-3,7,11,15-tetramethyl-hexadecyloxy]propan-1-yl 4-O-(2,3-di-O-benzoyl-6-O-sulfo-β-D-galactopyranosyl)-2,3,6-tri-O-benzoyl-β-D-glucopyranoside 10

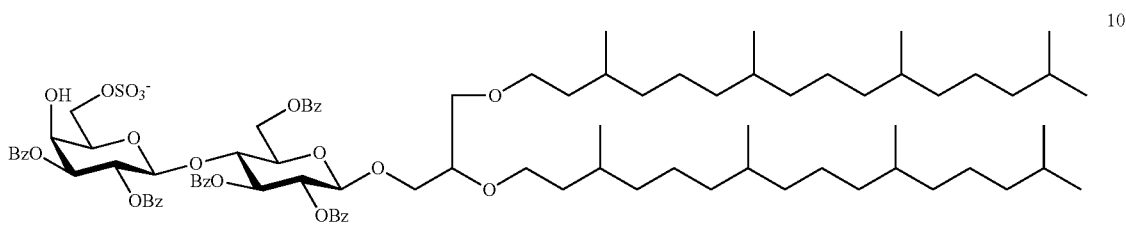

Diol (5, 92 mg, 0.061 mmol) was dissolved in anhydrous dichloromethane (2 mL) and pyridine (1 mL) with stirring under an atmosphere of argon at room temperature. To this was added trimethylamine sulfur trioxide complex (68 mg) and the stirring continued with the flask stoppered until the starting material disappeared by TLC (6:3:1 hexanes/ethyl acetate/dichloromethane). Then the solvent was evaporated at high vacuum and the residue was purified on a short flash column eluting with 10:90:0.2 methanol/dichloromethane/pyridine to yield a waxy solid (10, 61 mg, 64%).

$[\alpha]_D$ 40.0° (c, 0.0078, 1:1 $CH_2Cl_2/CH_3OH$); $^1H$ NMR 4:1 $CD_2Cl_2/CD_3OD$: δ 7.98 (brd, 2H, J=7.0, $Bz_o$), 7.91 (m, 6H, $Bz_o$), 7.86 (brd, 2H, J=7.3, $Bz_o$), 7.58 (brt, 1H, J=7.3, $Bz_p$), 7.56-7.29 (m, 12H, $Bz_p$, $Bz_m$), 7.21 (brt, 2H, J=7.3, $Bz_m$), 5.69 (brt, 1H, $J_{3,4}$=9.4, $H-3^{II}$), 5.59 (brt, 1H, $J_{2,3}$=10.4, $H-2^{II}$), 5.30 (brt, 1H, $J_{2,3}$=9.2, $H-2^{I}$), 5.12 (dd, 1H, $J_{3,4}$=3.5, $H-3^{II}$), 4.81 (d, 1H, $J_{1,2}$=7.9, $H-1^{II}$), 4.73 (d, 1H, $J_{1,2}$=7.9, $H-1^{I}$), 4.57 (brd, 1H, $J_{6,6'}$=11.8, $H-6^{I}$), 4.40 (dd, 1H, $J_{5,6'}$=4,4, $H-6^{I}$), 4.20 (brt, 1H, $J_{4,5}$=9.6, $H-4^{I}$), 4.13 (brd, 1H, $H-4^{II}$), 3.81 (m, 2H, CHH-arch-a, $H-5^{I}$), 3.57 (m, 3H, $H-5^{II}$, $H-6^{II}$, $H6^{III}$), 3.45 (m, 2H CHH-arch-a, CH-arch-b), 3.32 (m, 2H, $CH_2$-arch-d), 3.19 (m, 4H, $CH_2$-arch-c, $CH_2$-arch-e), 1.49 (m, 4H, arch-CH, $CH_2$), 1.43-0.84 (m, 44H, arch-CH, $CH_2$), 0.85 (m, 24H, arch-$CH_3$), 0.74 and 0.69 (2×d, J=6.4, arch-$CH_3$); $^{13}C$ NMR 4:1 $CD_2Cl_2/CD_3OD$: δ 166.71, 166.66, 166.5, 166.1, 166.0 (5×BzC=O), 134.2 (1×$Bz_p$) 133.9 (m, 4×$Bz_p$), 130.3-128.9 ($Bz_o$, $Bz_m$, $Bz_{ip}$), 102.0 ($C-1^{II}$), 101.7 ($C-1^{I}$), 78.2 (CH-arch-b), 77.2 ($C-4^{I}$), 74.6 ($C-3^{II}$), 74.1 ($C-3^{I}$), 73.6 ($C-5^{I}$), 73.3 ($C-5^{II}$), 72.8 ($C-2^{I}$), 71.0 (2×$CH_2$, arch-a, arch-d), 70.7 ($C-2^{II}$), 70.5 ($CH_2$, arch-e), 69.5 ($CH_2$, arch-c), 66.1 ($C-4^{II}$), 64.3 ($C-6^{II}$), 63.2 ($C-6^{I}$), 40.0, 38.04, 38.03, 37.98, 37.95, 37.88, 37.5, 37.1 ($CH_2$-arch), 33.4, 30.5, 30.2, 28.6 (CH, arch), 25.4, 25.0, 24.92, 24.89 ($CH_2$, arch), 20.07, 20.05, 19.9, 19.8 ($CH_3$, arch); HRMS Obs. 1599.8755, calcd. $C_{90}H_{128}O_{21}S_1Na_1$ $(M+Na)^+$ 1599.8567.

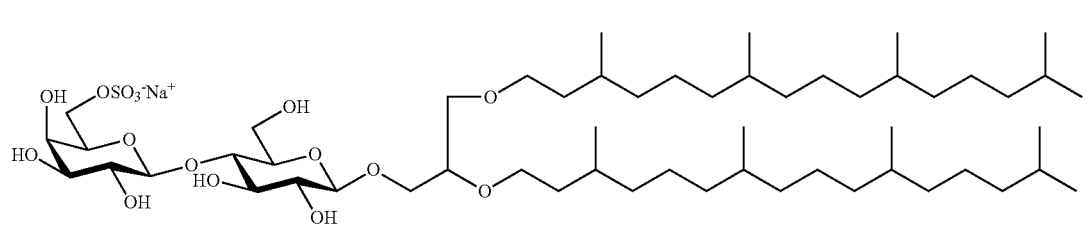

11

(2R)-2,3-Bis[(3R,7R,11R)-3,7,11,15-tetramethyl-hexadecyloxy]propan-1-yl 4-O-(6-O-sulfo-β-D-galactopyranosyl)-β-D-glucopyranoside 11

Protected sulfated glycolipid (10, 61 mg, 0.039 mmol) was dissolved in dry dichloromethane (2 mL) and dry methanol (1 mL) at room temperature with stirring under an atmosphere of argon. To this was added 1M methanolic sodium methoxide (0.31 mL) and the mixture was stirred for 5 h. Methanol (24 mL), chloroform (10.5 mL) and EDTA buffer (10 mL) were then added sequentially and the single-phase mixture was stirred for 16 h. [The EDTA buffer was made from water (100 mL), sodium acetate (820 nag), acetic acid (18 drops; pH~5 by pH paper) and ethylenediamine tetraacetic acid (29 mg).] The mixture was then transferred into a separatory funnel followed by the additions of chloroform (11 mL) and the same EDTA buffer (11 mL). The bottom organic layer was separated and the aqueous phase was washed with chloroform (2×11 mL). The combined organic layers were dried with sodium sulfate, filtered by gravity and concentrated by evaporation. The residue was dissolved in chloroform (25 mL) and transferred to a separatory funnel and further washed with saturated aqueous sodium bicarbonate (3×25 mL). The organic layer was dried with sodium sulfate, filtered by gravity and concentrated to dryness. After further drying at high vacuum, a waxy solid was isolated (11, 35 mg, 85%).

$[\alpha]_D$ 0.4° (c, 0.0057, 1:1 $CH_2Cl_2/CH_3OH$); $^1H$ NMR 1:1 $CD_2Cl_2/CD_3OD$: δ 4.27 (d, J=7.3, $H-1^{II}$), 4.26 (d, J=7.9, $H-1^{I}$), 4.21 (brt, 1H, $J_{5,6}$=8.9, $J_{6,6'}$=10.7, $H-6^{II}$), 4.05 (dd, 1H, $J_{5,6'}$=2.4, $H6^{III}$), 3.87 (brdd, 1H, J=9.8, J=3.1, CHH-arch-a), 3.79 (m, 4H, $H-4^{II}$, $H-5^{II}$, $H-6^{I}$, $H-6^{II}$), 3.58 (m, 4H, CHH-arch-a, CH-arch-b, $CH_2$-arch-c), 3.52-3.42 (m, 8H, $H-2^{II}$, $H-3^{II}$, $H-3^{I}$, $H-4^{I}$, $CH_2$-arch-d, $CH_2$-arch-e), 3.36 (m, 1H, $H-5^{I}$), 3.25 (m, 1H, $J_{2,3}$=9.2, $H-2^{I}$), 1.58-0.97 (m, 44H, arch-CH, $CH_2$), 0.84-0.78 (m, 30H, arch-$CH_3$); $^{13}C$ NMR 1:1 $CD_2Cl_2/CD_3OD$: δ 105.2 ($C-1^{II}$), 103.9 ($C-1^{I}$), 82.9 ($C-4^{I}$), 78.8 (CH-arch-b), 75.8 ($C-5^{I}$), 75.5 ($C-3^{I}$), 74.5 ($C-5^{II}$), 74.3 ($C-3^{II}$), 74.0 ($C-2^{I}$), 72.0 ($C-2^{II}$), 71.1 ($CH_2$, arch-d), 70.9 ($CH_2$, arch-e), 69.9 ($CH_2$, arch-a), 69.4 ($CH_2$, arch-c, C-4$^{II}$), 67.7 (C-6$^{II}$), 62.2 (C-6$^{I}$), 40.2, 38.3, 38.24, 38.21, 38.1, 37.8, 37.5, (CH$_2$-arch), 33.7, 30.8, 30.7, 30.6, 28.8 (CH, arch), 25.6, 25.28, 25.24, 23.1, 23.0 (CH$_2$, arch), 20.24, 20.21, 20.16 (CH$_3$, arch); HRMS Obs. 1079.7279, calcd. C$_{55}$H$_{108}$O$_{16}$S$_1$Na$_1$ (M+Na)$^+$1079.7256.

(2R)-2,3-Bis[(3R,7R,11R)-3,7,11,15-tetramethyl-hexadecyloxy]propan-1-yl 6-O-(3,4,6-tri-O-benzoyl-α-L-rhamnopyranosyl)-4-O-(2,3-di-O-benzoyl-β-D-galactopyranosyl)-2,3,6-tri-O-benzoyl-β-D-glucopyranoside 8

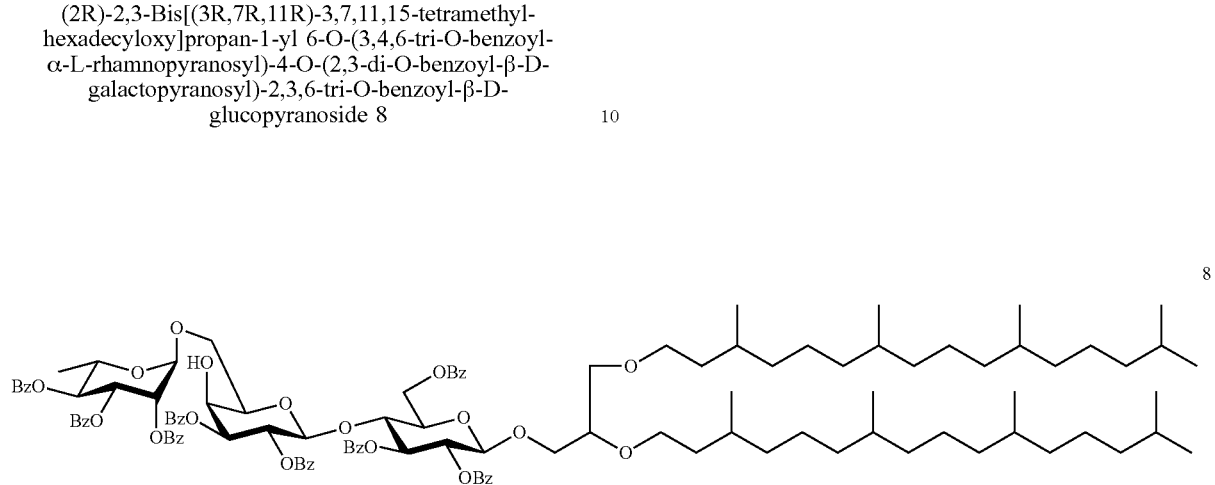

8

Trisaccharide donor (7, 100 mg, 0.071 mmol), archaeol (31 mg, 0.047 mmol) and 3 Å molecular sieves (about 100 mg) were dispersed with stirring in dry dichloromethane (1.5 mL) under an atmosphere of argon and cooled in an ice bath. After 20 min of stirring, N-iodosuccinimide (26 mg, 2.5 eq.) was added followed by the dropwise addition of a 0.25 M (with respect to boron) dichloromethane solution of BF$_3$.Et$_2$O/trifluoroethanol (1:2) (190 µL, 1 eq.) (Whitfield, D. M., Yu, S. H., Dicaire, C. J., and Sprott, G. D. 2010. *Carbohydr. Res.* 345:214-229). After 1 h, the reaction was quenched by sequential addition of saturated aqueous sodium bicarbonate (10 mL), 10% aqueous sodium thiosulfate (10 mL) and dichloromethane (5 mL). After complete disappearance of the red color, the mixture was transferred to a separatory funnel with rinsing with dichloromethane and water. The bottom organic layer was separated, dried with sodium sulfate, filtered by gravity and evaporated to dryness. The residue was purified by flash chromatography eluting first with 8:1:1 followed by 7:2:1 hexanes/ethyl acetate/dichloromethane to yield a waxy solid (8, 86 mg, 86%).

[α]$_D$ 64.1° (c, 0.0182, CH$_2$Cl$_2$); $^1$H NMR CDCl$_3$: δ 8.13 (brd, 2H, J=8.2, Bz$_o$), 8.03 (brd, 2H, J=8.2, Bz$_o$), 7.95 (m, 10H, Bz$_o$), 7.79 (brd, 2H, J=8.2, Bz$_m$), 7.64 (brt, 1H, J=7.5, Bz$_p$), 7.58-7.30 (m, 14H, Bz$_p$, Bz$_m$), 7.23 (brt, J=7.3, Bz$_m$), 5.75 (brt, 1h, J$_{3,4}$=9.5, H-3$^I$), 5.67 (brt, 1H, J$_{2,3}$=10.3, H-2$^{II}$), 5.61 (m, 2H, H-3$^{III}$, H-4$^{III}$) 5.48 (brs, 1H, H-2$^{III}$), 5.42 (brt, 1H, J$_{2,3}$=9.1, H-2$^I$), 5.28 (dd, 1H, J$_{3,4}$=2.6, H-3$^{II}$), 4.84 (d, 1H, J$_{1,2}$=7.9, H-1$^{II}$), 4.77 (d, 1H, J$_{1,2}$=7.6, H-1$^I$), 4.61 (m, 2H, H-1$^{III}$, H-6$^I$), 4.41 (dd, 1H, J$_{6,6}$=12.0, J$_{5,6'}$=4.1, H-6$^I$), 4.22 (m, 2H, H-4$^I$, H-4$^{II}$), 4.00 (m, 1H, H-5$^{III}$), 3.88 (m 1H, CHH-arch-a), 3.82 (m, 1H, H-5$^I$), 3.47 (m, 4H, H-5$^{II}$, H-6$^{II}$, CHH-arch-a, CH-arch-b), 3.36 (m, 2H, CH$_2$-arch-d), 3.27 (m, 4H, CH$_2$-arch-c, CH$_2$-arch-e), 2.96 (dd, 1H, J$_{6,6'}$=9.7, J$_{5,6'}$=5.0, H6$^{III}$), 1.52 (m, 4H, arch-CH, CH$_2$), 1.32-0.95 (m, 47H arch-CH, CH$_2$, CH$_3$$^{III}$), 0.86 (m, 24H, arch-CH$_3$), 0.69 (d, 3H, J=6.4, arch-CH$_3$), 0.62 (d, 3H, J=6.2, arch-CH$_3$); $^{13}$C NMR CDCl$_3$; δ 165.8, 165.7, 165.44, 165.42, 165.3, 165.2, 165.12, 165.10 (8×BzC═O), 133.5-133.1 (Bz$_p$), 130.0-128.2 (Bz$_o$, Bz$_{ip}$), 101.3 (C-1$^{II}$), 101.1 (C-1$^I$), 97.5 (C-1$^{III}$), 77.6 (CH, arch-b), 76.5 (C-4$^I$), 73.8 (C-3$^{II}$), 73.6 (C-3$^I$), 72.9 (C-5$^I$), 72.5 (C-5$^{II}$), 71.9 (C-2$^I$), 71.6 (C-3$^{III}$), 70.6 (CH$_2$, arch-c), 70.5 (C- 2$^{III}$), 70.1 (C-2$^{II}$), 69.9 (C-4$^{III}$), 69.9 (CH$_2$, arch-a), 69.8 (CH$_2$, arch-d), 69.1 (CH$_2$, arch-e), 66.7 (C-5$^{III}$), 66.4 (C-4$^{II}$), 64.1 (C-6$^{II}$), 62.4 (C-6$^I$), 39.4, 37.5, 37.44, 37.40, 37.3, 36.9, 36.4 (CH$_2$-arch), 32.8, 29.9, 29.6, 28.0 (CH, arch), 24.8, 24.5, 24.31, 24.26, 22.7, 22.6 (CH$_2$, arch), 19.7, 19.6, 19.5 (CH$_3$, arch), 17.6 (C-6$^{III}$); HRMS Obs. 1978.0309, calcd. C$_{117}$H$_{150}$O$_{25}$Na$_1$ (M=Na)$^+$1978.0358.

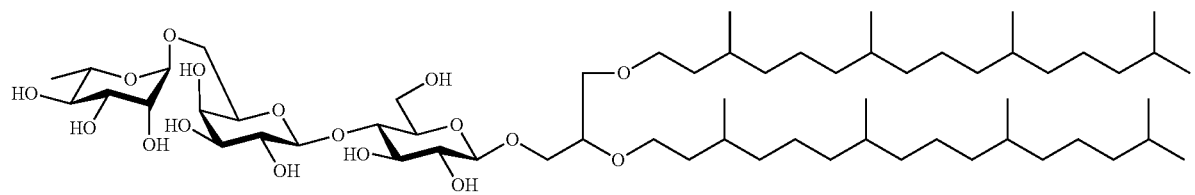

9

(2R)-2,3-Bis[(3R,7R,11R)-3,7,11,15-tetramethyl-hexadecyloxy]propan-1-yl 6-O-(α-L-rhamnopyranosyl)-4-O-(β-D-galactopyranosyl)-β-D-glucopyranoside 9

Benzoylated trisaccharide glycolipid (8, 69 mg, 0.035 mmol) was dissolved at room temperature under an atmosphere of argon with stirring in dry dichloromethane (2 mL) and dry methanol (2 mL). To this solution was added 1M methanolic sodium methoxide (440 μL) and the stirring continued for 22 h. The mixture was neutralized to about pH 5 with Rexyn 101(H) resin which had been pre-washed with water then methanol. The mixture was filtered by vacuum filtration and evaporated to dryness. The desired trisaccharide glycolipid (9, 30 mg, 76%) was isolated from a short flash chromatography column eluting with 80:22.5:10:4 chloroform/methanol/acetic acid/water.

$[\alpha]_D$ –11.2° (c, 0.0075, 1:1 $CH_2Cl_2/CH_3OH$); $^1H$ NMR 1:1 $CDCl_3/CD_3OD$: δ 4.69 (brs, 1H, H-1$^{III}$), 4.31 (d, 1H, $J_{1,2}$=7.4, H-1$^{II}$), 4.29 (d, 1H, $J_{1,2}$=8.0, H-1$^I$), 3.92 (m, 2H, H-2$^{III}$, (CHH- arch-a), 3.86 (m, 2H, H-6$^I$, H-6$^{I\prime}$), 3.78 (brs, 1H, H-4$^{II}$), 3.72-3.46 (m, 17H, H-2$^{II}$, H-3$^{I,II,III}$, H-4$^{I,III}$, H-5$^{III}$, H-6$^{II}$, H6$^{II\prime}$, CHH-arch-a, $CH_2$-arch-c, CH-arch-b, $CH_2$-arch-d, $CH_2$-arch-e), 3.37 (m, 2H, H-5$^{I,II}$), 3.29 (brt, 1H, H-2$^I$), 1.26 (d, 3H, $CH_3^{III}$), 1.59-1.30 (m, 6H, arch-CH, $CH_2$), 1.27-1.01 (m, 42H, arch-CH, $CH_2$), 0.88-0.82 (m, 30H, arch-$CH_3$); $^{13}C$ NMR 1:1 $CDCl_3/CD_3OD$: δ 105.0 (C-1$^{II}$), 103.9 (C-1$^{III}$), 102.1 (C-1$^I$), 82.3 (C-4$^I$), 78.5 (CH, arch-b), 75.7 (C-3$^{II}$), 75.6 (C-5$^{II}$), 75.0 (C-4$^{III}$), 74.3 (C-2$^{II}$), 74.0 (C-2$^I$), 73.4 (C-5$^I$), 71.8 (C-5$^{III}$), 71.7 (C-3$^{III}$), 71.1 ($CH_2$, arch-c), 69.9 ($CH_2$, arch-a), 71.0 (C-2$^{III}$), 70.8 ($CH_2$, arch-d), 69.5 ($CH_2$, arch-e), 69.4 (C-4$^{II}$), 69.3 (C-3$^I$), 68.0 (C-6$^{II}$), 62.0 (C-6$^I$), 40.1, 38.13, 38.09, 38.0, 37.7, 37.3 ($CH_2$-arch), 33.5, 30.6, 30.5, 28.7 (CH, arch), 25.5, 25.14, 25.09 ($CH_2$, arch), 23.1, 23.0, 20.25, 20.22, 20.17 ($CH_3$, arch), 17.9 (C-6$^{III}$); HRMS Obs. 1123.8550, calcd. $C_{61}H_{119}O_{17}$ $(M+H)^+$ 1123.8447.

Example 2: Archaeosome Vaccine Formulation and Analysis

Methods:

In one method, archaeosomes were formed by hydrating 20-30 mg dried lipid at 40° C. in 2 ml PBS buffer (10 mM sodium phosphate, 160 mM NaCl, pH 7.1) with the protein antigen OVA dissolved at 10 mg/ml. Vesicle size was reduced to about 100-150 nm diameter by brief sonication in a sonic bath (Fisher Scientific), and the portion of OVA antigen not entrapped was removed by centrifugation from 7 ml PBS followed by 2 washes (200,000×g max for 30 min). Vesicle pellets were resuspended in 2-2.5 ml PBS and filter sterilized through 0.45 μm Millipore filters. Sterile conditions and pyrogen-free water was used throughout.

In another method, lipids dissolved in t-butanol/water received antigen dissolved in an equal volume of water. The sample was then lyophilized to a powder and rehydrated in PBS buffer. Size was reduced, antigen not entrapped was removed, and filtration conducted as above.

When synthetic monophosphoryl lipid A (PHAD™, Avanti Polar Lipids, Alabama, USA) was used as a coadjuvant, it was included in the hydration mixture as S-lactosylarchaeol/PHAD (95/5 mol %).

Quantification of antigen loading was conducted by separating protein(s) from lipids using SDS polyacrylamide gel electrophoresis as described (Sprott, G. D., Patel, G. B., and Krishnan, L. 2003. *Methods Enzymol,* 373:155-172). Loading of synthetic archaeosomes with antigens was also determined using SDS Lowry with standard curves prepared for the respective antigen. Loading was based on μg protein/mg salt corrected dry weight of lipid. Average diameters based on Intensity and Zeta potentials were measured using a Malvern Nano Zetasizer with a He/Ne laser (Spectra Research Corp., Ontario, Canada).

Results:

To explore the feasibility of using single lipid adjuvants consisting of S-glycolipid, and of replacing phospholipid with S-glycolipid to introduce stability in archaeosomes, 6'-S-lactosylarchaeol and lactosylarchaeol were synthesized as described in Example 1.

Archaeosome vesicles did not form using 100 mol % lactosylarchaeol or in other examples of neutrally charged glycolipids such as triglucosylarchaeol (not shown). However, introduction of a sulfate moiety to the glyco group resulted in archaeosomes comprised of a single lipid with excellent hydrating ability. Further, the S-lactosylarchaeol served as a source of charge to allow stable archaeosomes to be made from combination with uncharged lactosylarchaeol. The combinations that hydrated best contained at least 30 mol % (or more) S-glycolipid. However, attempts to prepare archaeosomes with a mixture as high as 90 mol % uncharged to 10 mol % S-glycolipid resulted in archaeosomes that still entrapped antigen (Table 1).

However, unlike other preparations that contained higher amounts of SLA, those with only 10% increased dramatically in size upon storage indicating loss of stability.

TABLE 1

Archaeosome vaccine characteristics and stability.

| Archaeosome | Loading (μg antigen/mg archaeosome) | Zeta potential (mV) At first injection | Zeta potential (mV) 20 weeks | Average Diameter (nm) At first injection | Average Diameter (nm) 20 weeks |
|---|---|---|---|---|---|
| SLA | 22.0 | −47.1 | −50.5 | 168 | 168 |
| SLA/AS | 38.0 | −44.8 | −49.8 | 202 | 200 |
| LA/SLA | 24.2 | −32.4 | −34.5 | 250 | 208 |
| Rha-LA/SLA | 22.3 | −30.4 | −32.6 | 205 | 204 |
| Glc$_3$A/SLA | 13.6 | −28.2 | −32.6 | 155 | 146 |
| SLA/PHAD (95/5) | 14.6 | −72.0 | −42.5 | 66 | 133 |

| Archaeosome | Loading (μg antigen/mg archaeosome) | Zeta potential (mV) At first injection | Zeta potential (mV) 20 weeks | Average Diameter (nm) At first injection | Average Diameter (nm) 12 weeks |
|---|---|---|---|---|---|

TABLE 1-continued

Archaeosome vaccine characteristics and stability.

| | | | | | |
|---|---|---|---|---|---|
| SLA | 35.0 | −48.1 | −52.7 | 172 | 176 |
| SLA/LA (90/10) | 41.8 | −47.3 | −49.4 | 197 | 190 |
| SLA/LA (70/30) | 12.0 | −43.6 | −45.0 | 202 | 186 |
| SLA/LA (50/50) | 25.3 | −37.0 | −39.7 | 165 | 169 |
| SLA/LA (30/70) | 44.1 | −26.9 | −29.6 | 167 | 172 |
| SLA/LA (10/90) | 25.9 | −18.8 | −14.7 | 196 | 1035 |
| *M. smithii* TPL | 40.1 | −40.7 | −38.2 | 168 | 169 |

Example 3: Adjuvant Optimization and Biological Analysis

Methods:

Animal Trials

C57BL6 female mice (6.8 weeks old) were immunized subcutaneously with 0.1 ml vaccines containing the equivalent of 20 µg OVA, often entrapped in archaeosomes of various compositions, A booster consisting of the same vaccine and route was given most often on week 3. In experiments addressing ability of archaeosomes to evoke immune response to a cancer self-antigen, TRP or Gp100 antigen in archaeosomes was administered at a dose of 15 µg antigen per injection and booster given on week 3.5 and week 8.5. In some experiments an additional third injection was given (~95 days after first dose). All protocols and SOPs were approved by the NRC Animal Care Committee and conducted within the guidelines of the Canadian Council on Animal Care.

Statistics

A comparison of means for animal data was conducted using student's t test to determine significance at 95% confidence, and two tailed P values calculated.

Immune Responses

As a measure of $CD4^+$ T cell response, antibody raised to the antigen in the vaccine and present in the sera of mice (5-6 mice/group), was quantified by Elisa according to a previous description (Krishnan, L., Dicaire, C. J., Patel, G. B., and Sprott, G. D. 2000. *Infect, Immun.* 68:54-63). The $CD8^+$ T cell response was quantified by sacrificing 2 mice/group and pooling their splenic cells. These were assayed in triplicate for antigen-specific responses by Elispot and CTL methods (Krishnan, L., Sad, S., Patel, G. B., and Sprott, G. D. 2003. *Cancer Res.* 63:2526-2534).

Results:

Adjuvant Activity of S-Glycolipids

In a first example, adjuvant activity of the natural sulfated glycolipid purified from *Haloferax volcanii* (6'-$HSO_3$-D-$Man_p$-α-1,2-D-$Glc_p$-α-1,1-archaeol) was compared to a synthetic 6'-S-lactosylarchaeol, not found in nature. Archaeosomes carrying OVA as antigen were prepared using both S-glycolipids. Mice were immunized subcutaneously at 0 and 3 weeks with the OVA-loaded archaeosome adjuvants (FIG. 2). $CD8^+$ T cell responses measured by Elispot splenic cell assays. The antigen with no adjuvant (OVA) and non-immunized mice (naive) were included as negative controls. Spleens from duplicate mice were collected 6 weeks post first injection to determine the frequency (number of spots) of interferon-gamma (IFN-γ)-secreting splenic cells by enzyme-linked immunospot assay (Elispot). Omission of the major CD8 epitope of OVA (SIINFEKL) from the assay (no peptide) was used to test for antigen-nonspecific responses.

The 6'-S-lactosylarchaeol archaeosome adjuvant produced the highest response in mice, which was much better than the natural SGL-1 archaeosome. Negative controls, including non-immunized mice (naive) and an equivalent amount of antigen without adjuvant, produced little responses. Comparison of means was significant ($P<0.05$) for SLA versus SGL-1 ($P=0.0021$). Means were not significantly different for SGL-1 versus OVA ($P=0.5467$). All responses using adjuvant were antigen-specific as seen from the controls where SIINFEKL peptide was deleted from the Elispot assays.

Figure 3:
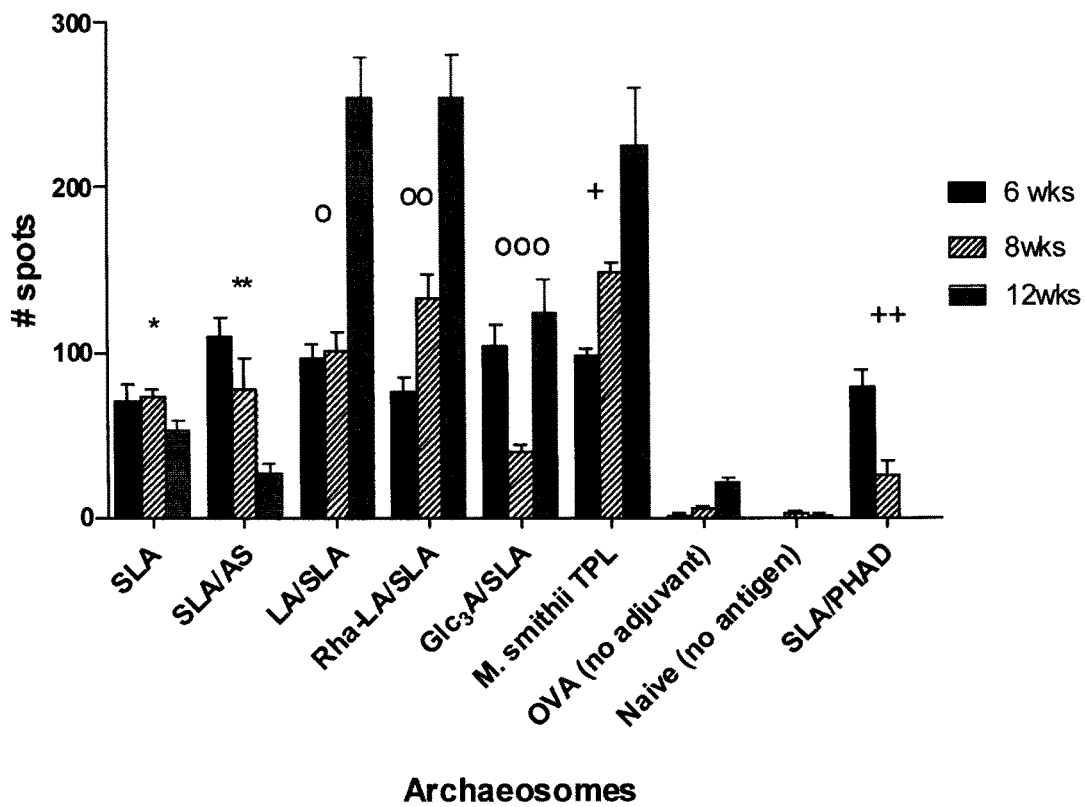
FIG. 3 shows a graph illustrating the assessment of SLA as either a single lipid archaeosome adjuvant or as a replacement for phospholipid in combinations with other synthetic neutrally-charged archaeols.

In a second example shown in FIG. 3, mice were immunized with OVA-archaeosomes where the lipid was either 6'-S-lactosylarchaeol, or 6'-S-lactosylarchaeol in combination with other synthetic archaeols in 50/50 mol ratio. Results were compared to a positive control group of animals immunized with archaeosomes-OVA prepared from TPL of *M. smithii* (Krishnan, L., Sad, S, Patel, G. B., and Sprott, G. D. 2000. *J. Immunol.* 165: 5177-5185). $CD8^+$ T cell assays were conducted in triplicate using splenic cells pooled from duplicate mice at 6, 8 and 12 weeks post first injection. In all cases omission of SIINFEKL resulted in very low background showing the measured responses were antigen specific. In the short term (6 weeks after first injection), all archaeosome adjuvants produced similar Elispot responses including 6'-S-lactosylarchaeol in novel combination with the well-known adjuvant PHAD. Antigen with no adjuvant and non-immunized naive mice gave essentially no responses, indicating the importance of using an adjuvant. In the longer term, i.e. 12 weeks from first injection, where 6'-S-lactosylarchaeol was combined with the neutral synthetic lipids LA or Rha-LA, antigen-specific responses were enhanced and at least equivalent to the positive control (*M. smithii* TPL archaeosomes). Means significantly different at 12 weeks were * versus ** ($P=0.0030$), * versus o $P=0.0002$), * versus oo ($P=0.0002$), * versus ooo ($P=0.0043$), and * versus+($P=0.0010$) (see FIG. 3 for symbol designations).

As a co-adjuvant with SLA archaeosomes, PHAD was counter-productive for the $CD8^+$ T cell response. Although the initial immune response was little affected by PHAD, in the longer term PHAD had the effect of decreasing the $CD8^+$ T cell response.

Figure 4A:
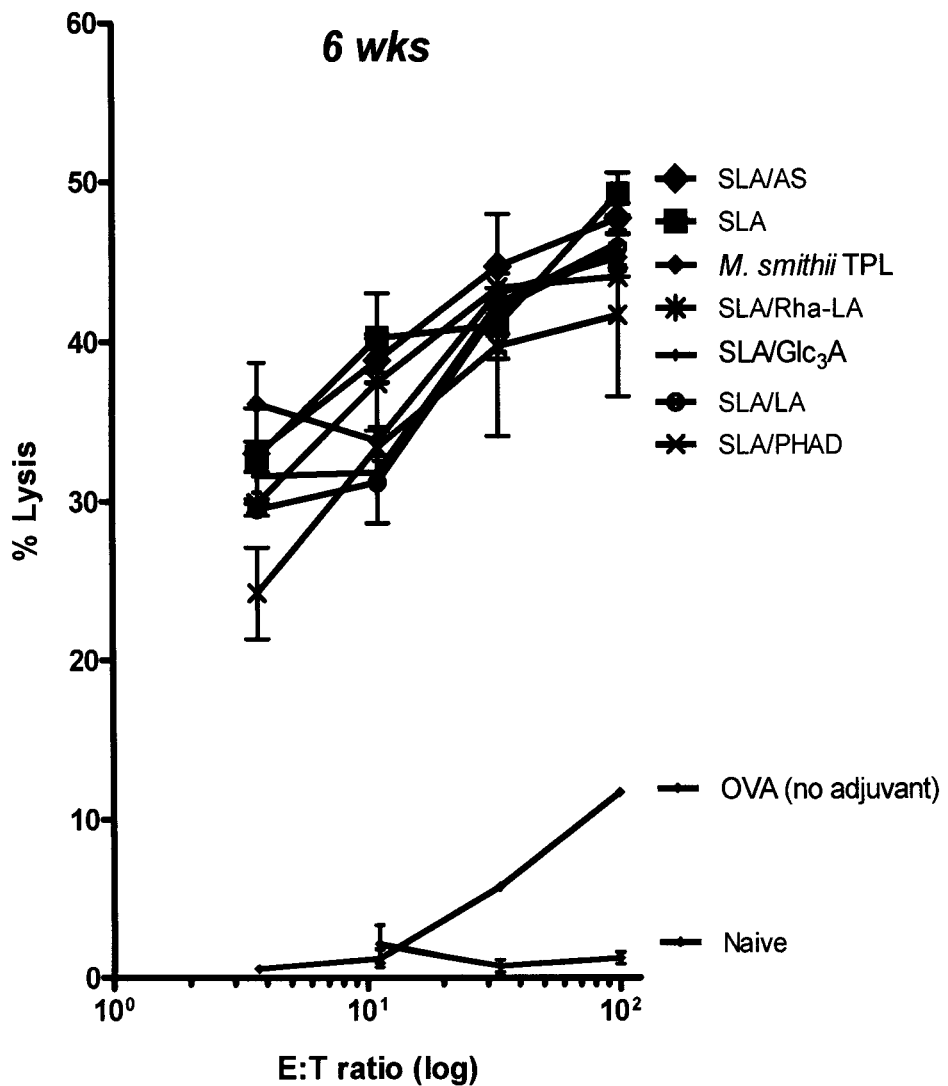
FIG. 4 shows graphs illustrating the results of a cytotoxic T lymphocyte (CTL) lysis assay used to assess the same populations of splenic cells as in FIG. 3. The standard $^{51}$Cr assay was conducted using specific and non-specific target cells (EG.7 and EL-4, respectively). The ratios of effector splenic cells to target cells are shown as the E:T ratio in the graph. A, B and C show time points of 6, 8 and 12 weeks post first immunization using EG.7 targets.
Figure 4B:
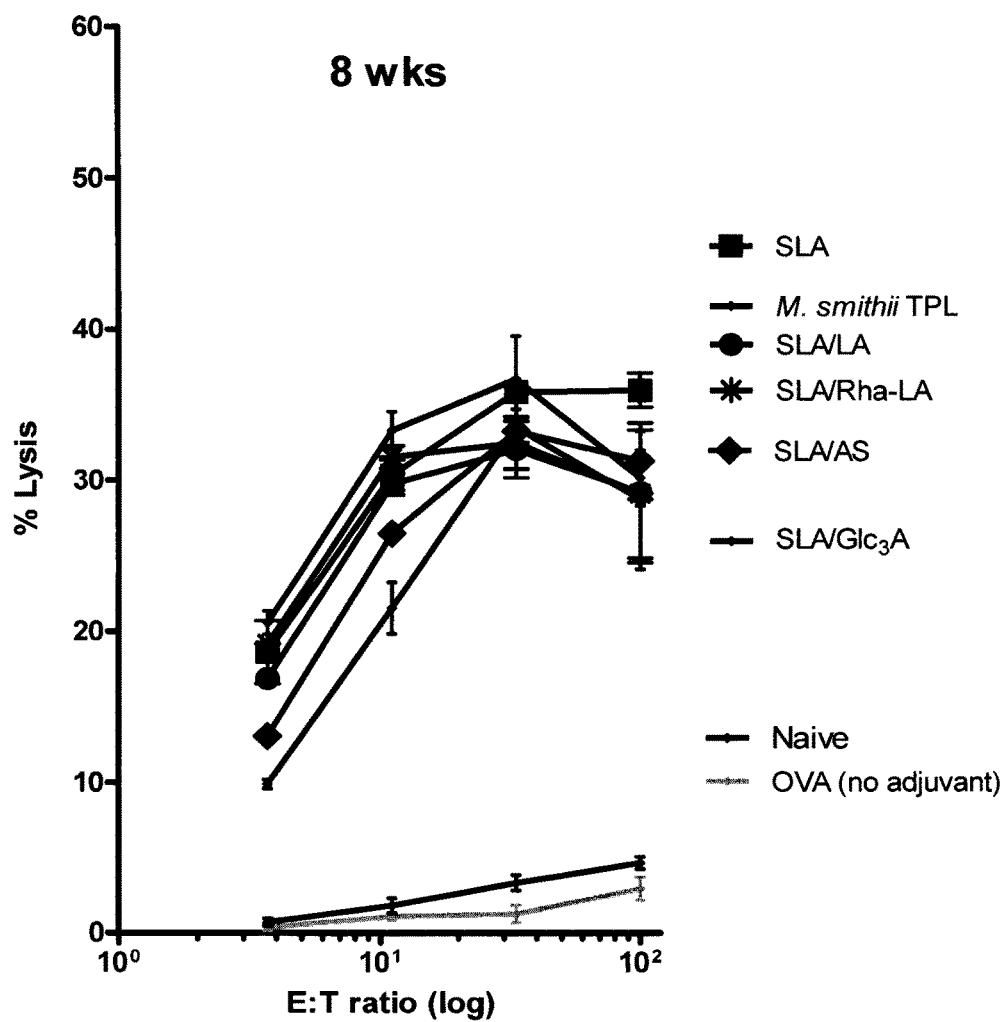
Figure 4C:
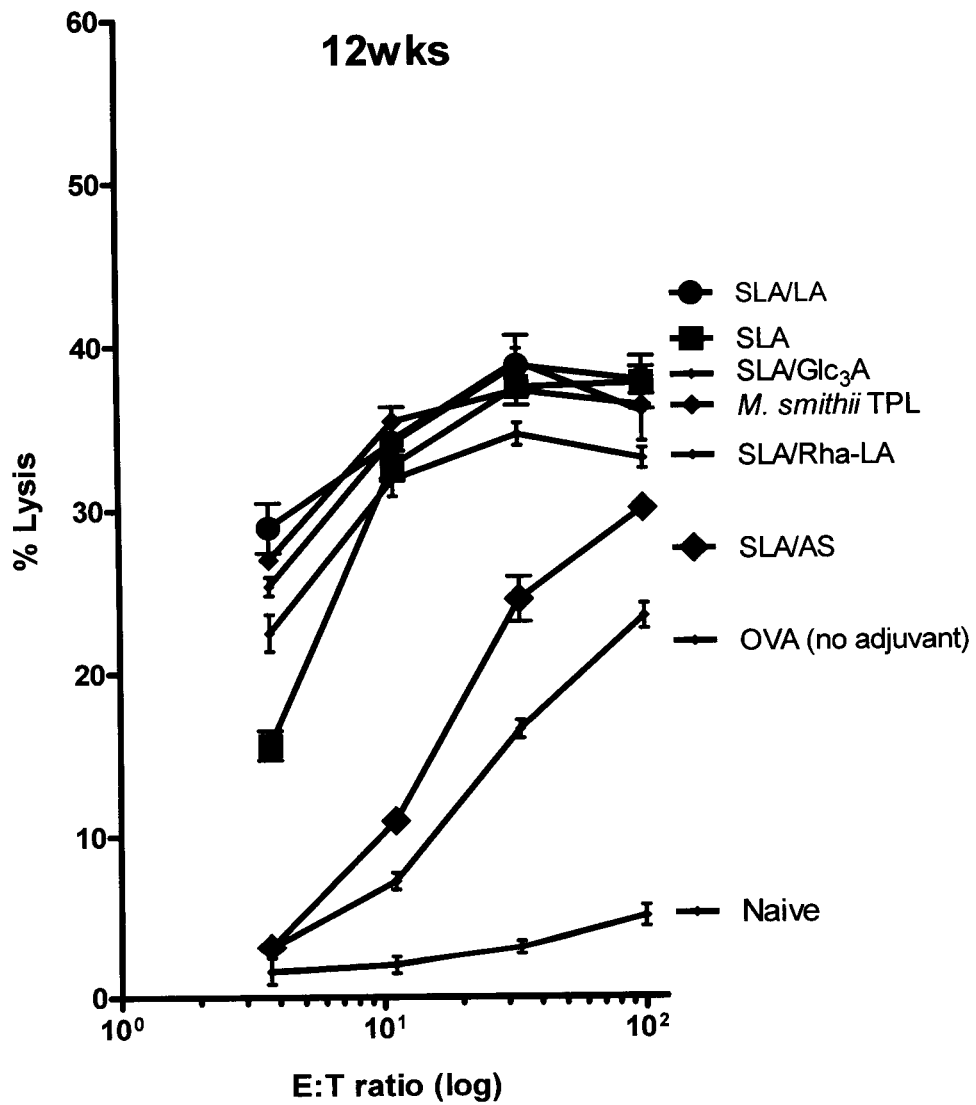
Figure 5A:
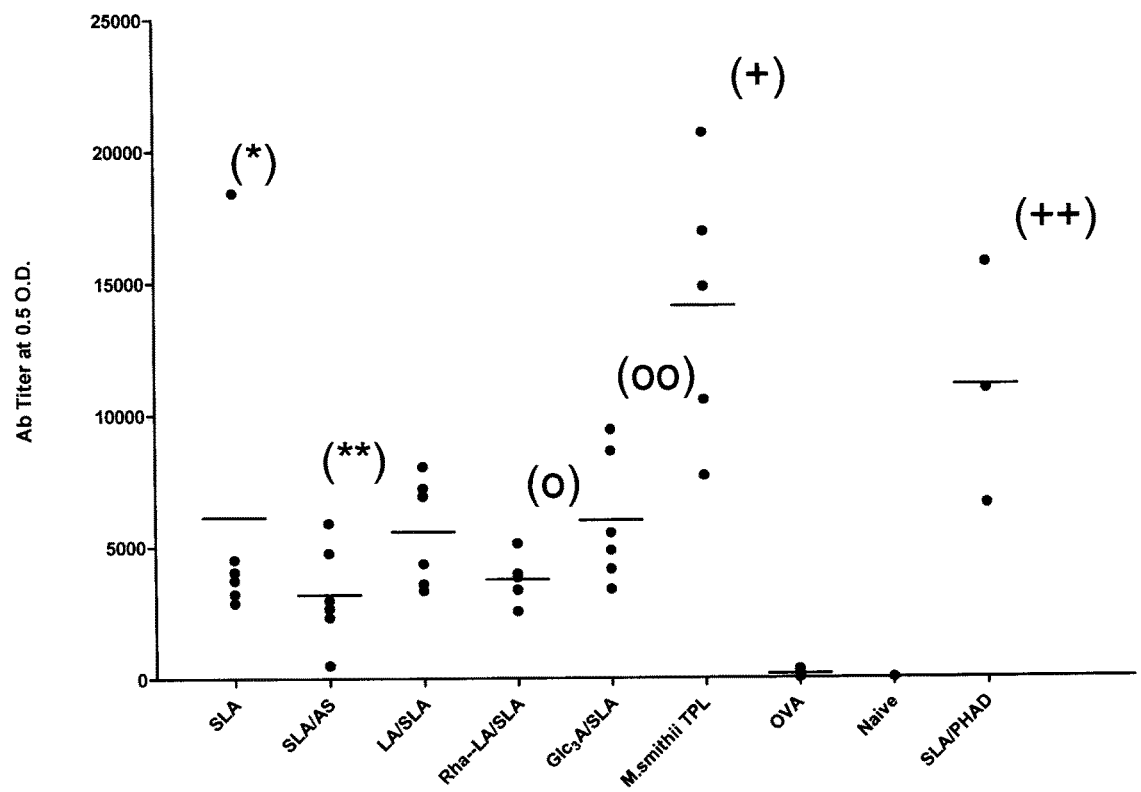
FIG. 5 shows graphs illustrating the results of testing antibody titres in sera of mice immunized with various archaeosome adjuvants and in combination with PHAD (synthetic lipid A), The titre of anti OVA antibody (IgG) for each mouse is shown as a separate data point. A, 6 weeks and B, 8 weeks post first injection.
Figure 5B:
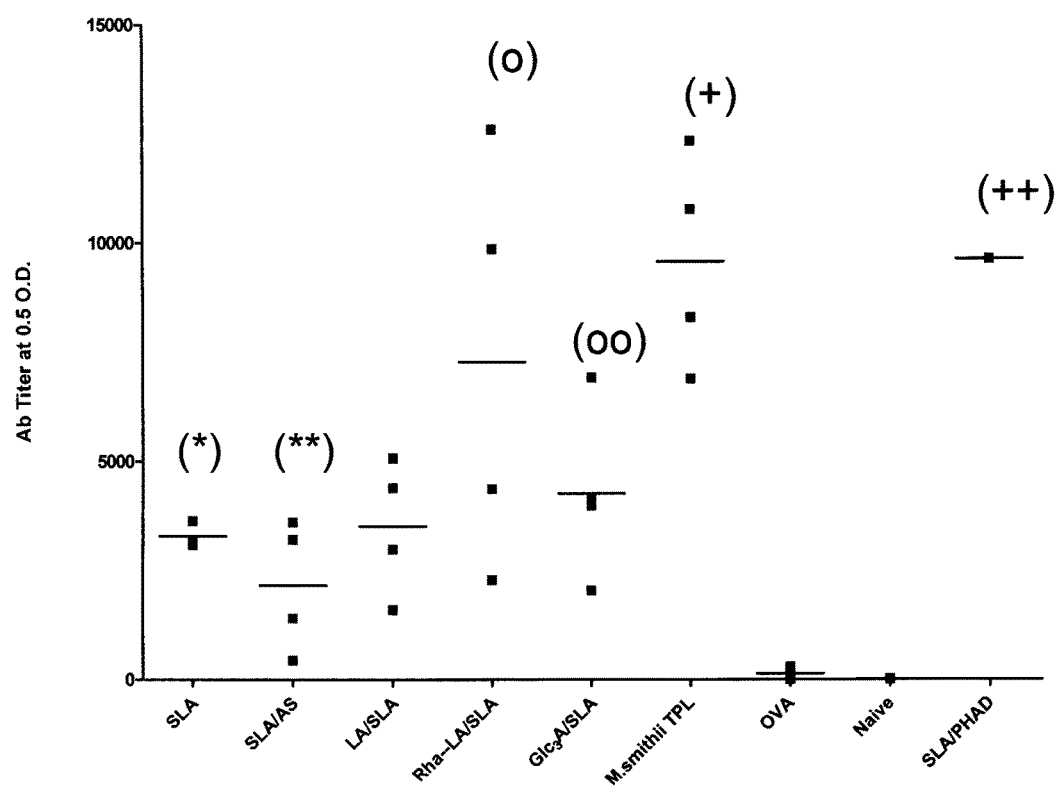

A second CTL method of assaying $CD8^+$ T cell immunity was used to confirm Elispot activities. CTL responses were measured in the same splenic cell suspensions used for the Elispot assays (FIG. 4, A-C) with similar results except for higher activity with 6'-S-lactosylarchaeol/triglucosylarchaeol. Best adjuvant activity seen in the long term (FIG. 4C, 12 weeks), and especially obvious at low Effector:Target ratios, in order from high to low activity were: 6'-S-lactosylarchaeol/lactosylarchaeol>6'-S-lactosylarchaeol/triglucosylarchaeol>6'-S-lactosylarchaeol/rhamnosyl-lactosylarchaeol>6'-S-lactosylarchaeol>6'-S-lactosylarchaeol/archaetidylserine>OVA no adjuvant>naive mice. EL-4 non-specific targets produced only low responses, not shown.

Anti-OVA antibody titres measured in the sera of mice bled at 6 and 8 weeks from first injection are shown in FIGS.

5, A and B. Significant titres of anti OVA antibody were found in all sera, except for the naive (not immunized) and 'OVA no adjuvant' groups. The PHAD co-adjuvant, and inclusion of Rha-LA, had a positive effect on the SLA archaeosome adjuvant in terms of antibody responses. At the 6 week point SLA means were not significantly different than SLA/PHAD (P=0.2556), but became strikingly significant at the 8 week point. Means not significantly different at 8 weeks included o versus+(P=0.4238) (see figure for symbol details).

Optimum Ratio of SLA/LA

Figure 6:
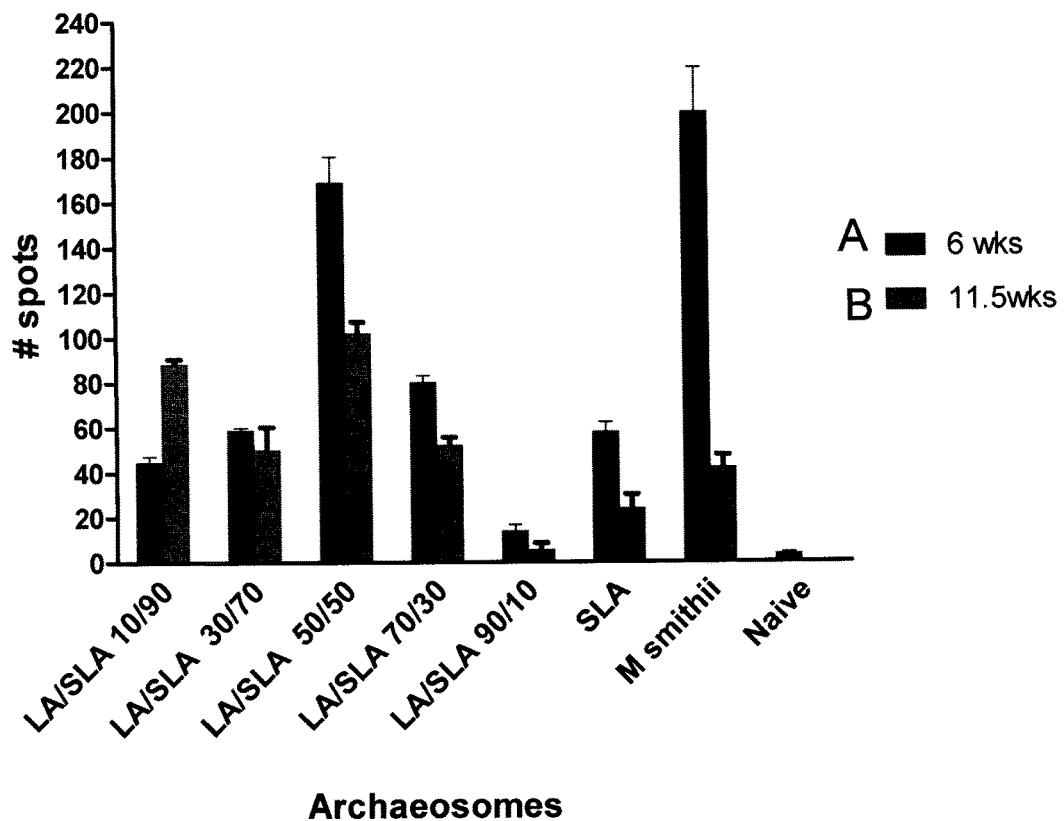
FIG. 6 shows a graph illustrating the results of testing adjuvant activity of SLA archaeosomes, and how this is influenced by the amount of neutral LA included in the formulation. Archaeosome preparations, details of which are shown in Table 1, were used to immunize mice. Elispot assays were performed on splenic cells at weeks 6 (A) and 11.5 (B) from first injection.
Figure 7:
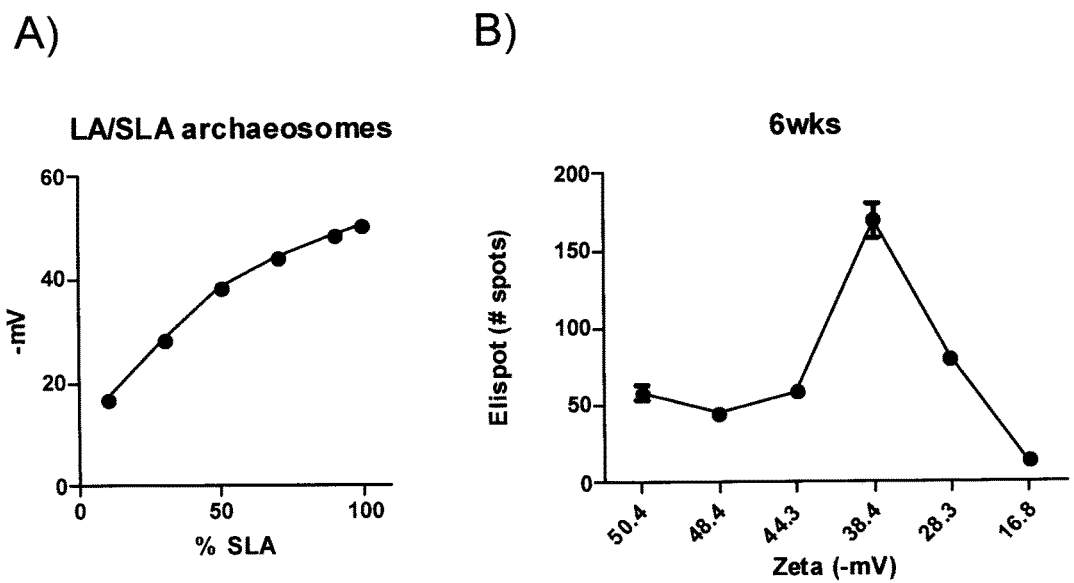
FIG. 7 shows a graph illustrating the results of manipulating surface charge of SLA archaeosome adjuvants by varying SLA/LA ratio and effect on immune response. In panel A, the Zeta potentials are shown in mV for OVA-archaeosomes prepared from various mol % of neutral glycoarchaeol included in a synthetic SLA archaeosome vaccine. Panel B shows a graph illustrating the results of a cytotoxic T lymphocyte (CTL) lysis assay used to assess the same populations of splenic cells as in FIGS. 3 and 4. The standard $^{51}$Cr assay was conducted using specific and non-specific target cells (EG.7 and EL-4, respectively). The ratios of effector splenic cells to target cells are shown as the E:T ratio in the graph. The graph shows time points of 7 weeks post first immunization using EG.7 targets.

Adjuvants comprised of SLA/LA combinations were investigated in animal trials to explore whether a preferred combination could be identified. Vaccines were formulated by entrapping antigen in SLA archaeosomes wherein the amount of LA varied from 0 to 90 mol % (FIG. 6). Archaeosomes did not hydrate well at 100% LA, so a pure LA archaeosome adjuvant could not be tested. Mice were immunized and immune Elispot assays performed on splenic cells at 6 and 11.5 weeks post first immunization. A 1:1 ratio of SLA/LA was clearly optimal at both time points. The observation that SLA/LA combinations using at least 30% SLA gave higher immune responses than the positive control indicates that a strong memory response can be achieved with a synthetic SLA/LA archaeosome vaccine. In FIG. 7, data are shown that the surface charge cleanly varies with the SLA to LA ratio providing strong evidence that the lipids mix in the archaeosome formulations evenly and not in monolipid aggregates.

Protective Response Against Cancer Raised by the Vaccine

Figure 8A:
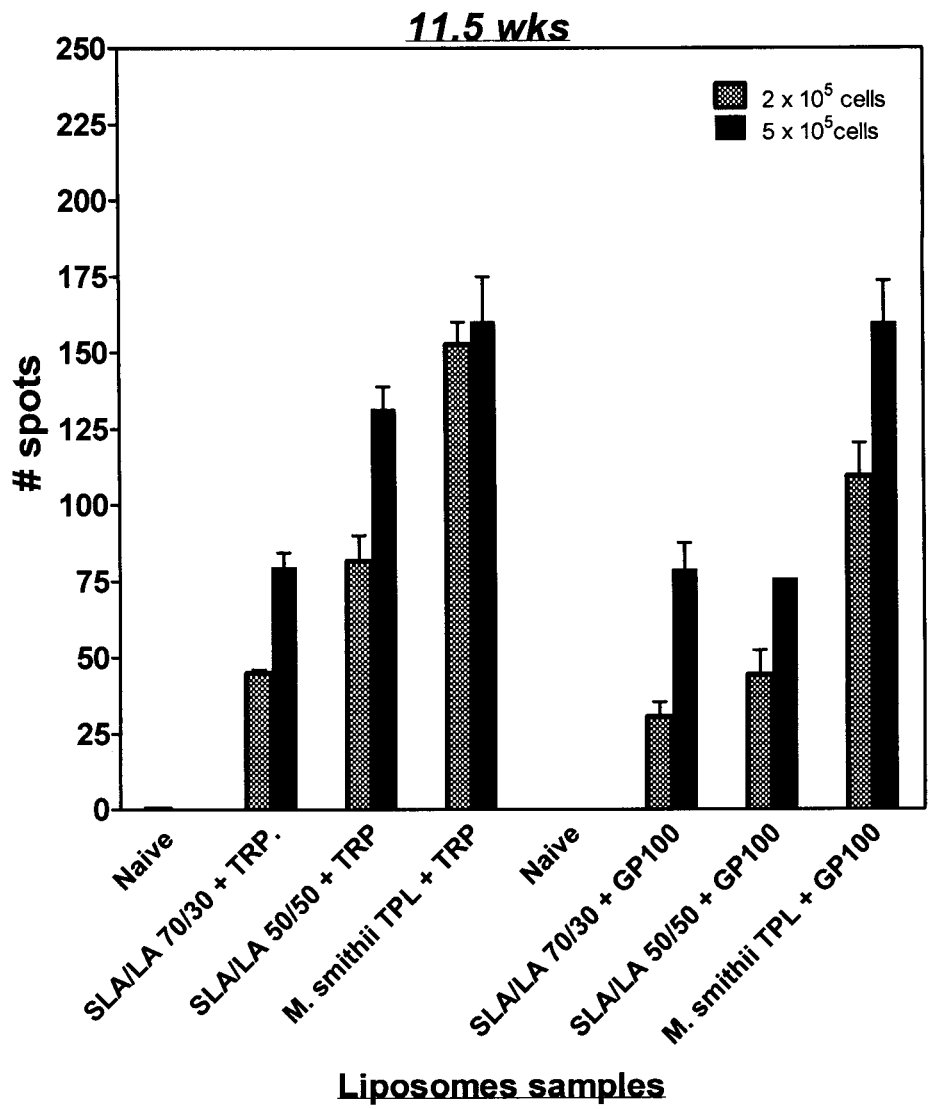
FIG. 8 shows graphs illustrating the results of testing the induction of CD8+ T cells against a cancer self-antigen delivered in various liposomes. The two cancer antigens evaluated were Tyrosinase-related protein (TRP) and Gp100. ELISPOT assays (8a) were performed on splenic cells at 11.5 weeks after vaccination (3 dose regimen). Cytotoxic T lymphocyte (CTL) response was carried out at 11.5 weeks using spleen cells effector and non-specific EL-4 target (8b) or specific EL-4+TRP target cells (8c).
Figure 8B:
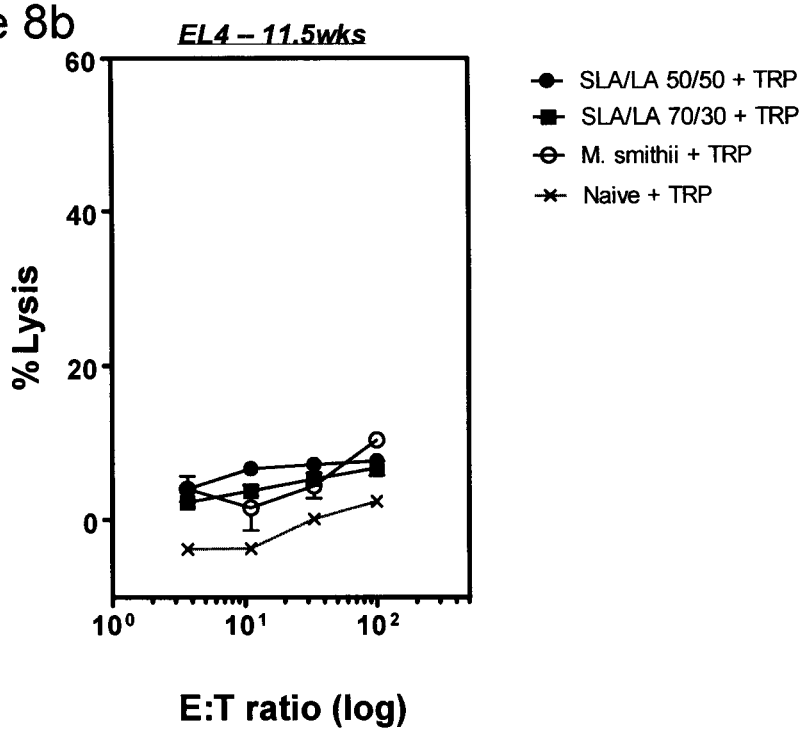
Figure 8C:
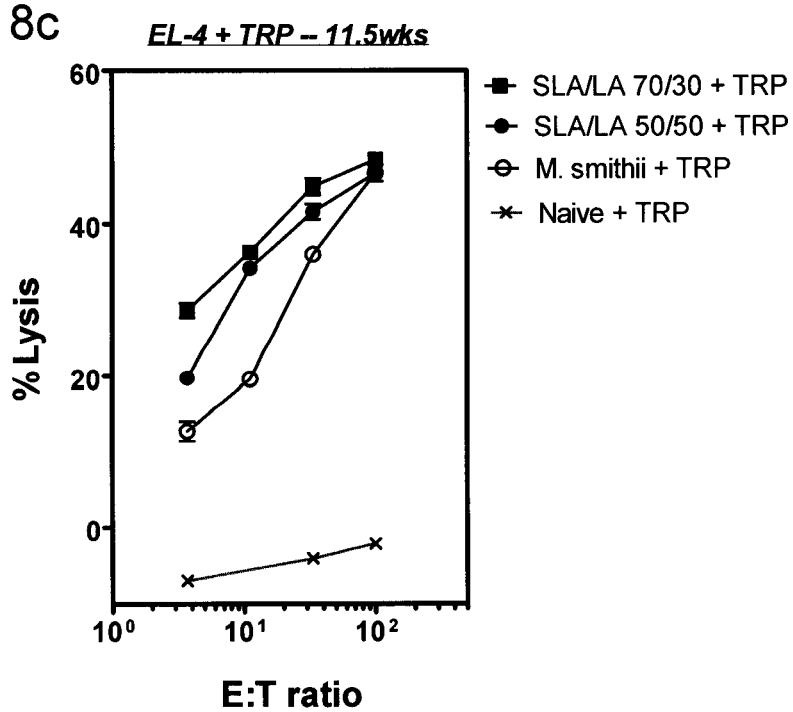
Figure 9:
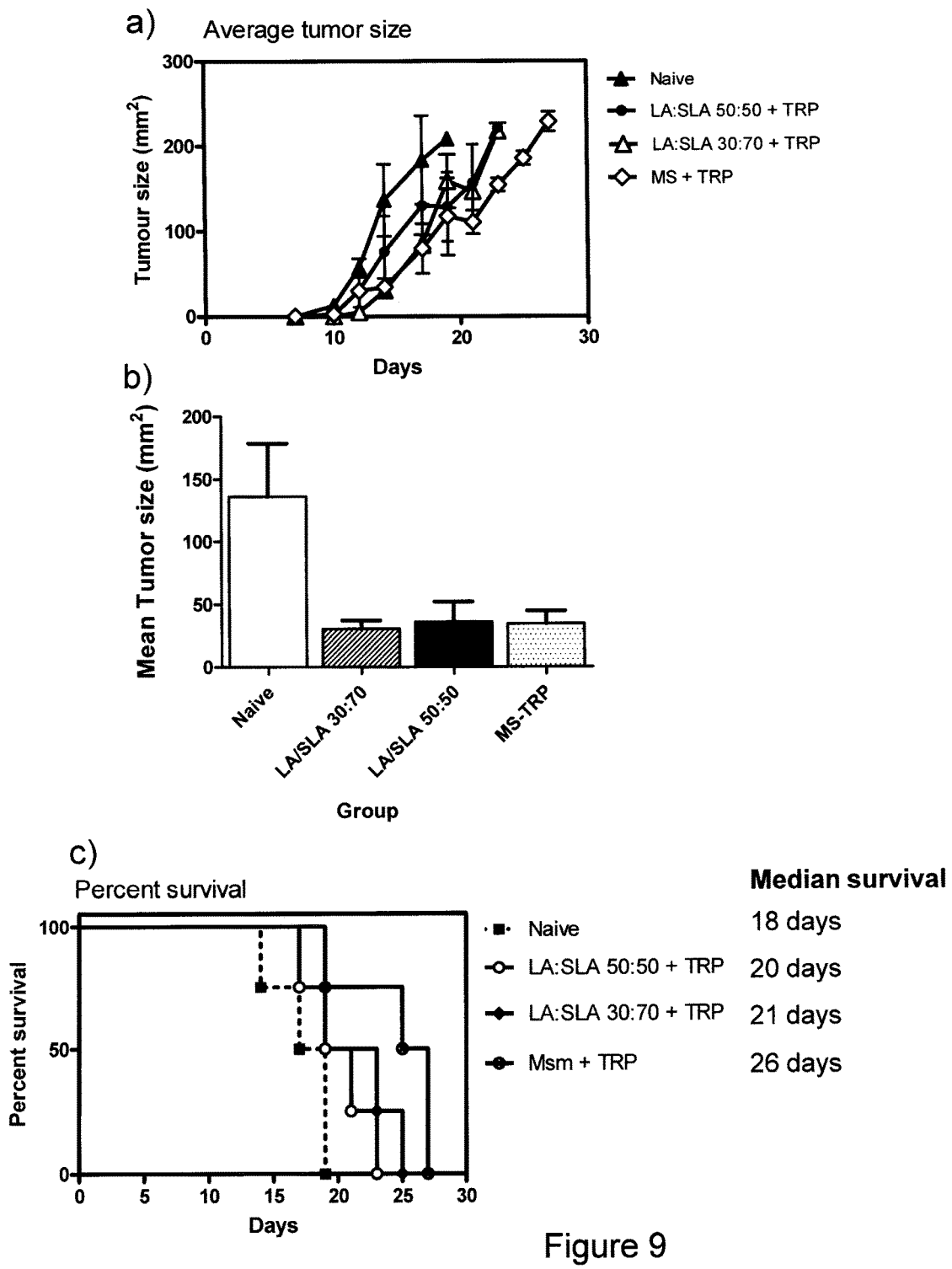
FIG. 9 shows graphs illustrating the results of a tumor challenge study in vaccinated mice. Animals were vaccinated with indicated liposomes containing the TRP antigen. At 11.5 weeks post-vaccination (3 dose vaccine regimen, 15 µg of TRP per mouse per injection, subcutaneous), animals were injected with B16 melanoma tumor cells in the mid-back. Archaeosomes prepared from the total polar lipids of M. Smithii containing TRP were used as controls. The average tumor size progression over time in naïve (non-vaccinated) and various vaccinated groups is indicated in FIG. 9a. The average tumor size in various groups is shown on day 14 after tumor challenge (9b). The mean survival of mice following tumor challenge is also illustrated (FIG. 9c)

Adjuvants comprised of SLA/LA and total polar lipid mixture derived from the archaea *Metheanobrevibacter smithii* was investigated in animal trials to explore if vaccination could protect against subsequent tumor challenge (FIG. 8, 9, 11). Firstly, delivery of cancer self-antigen in SLA/LA archaeosomes evoked a $CD8^+$ T cell response (FIG. 8). Secondly, challenge with a B16 cancer cell line expressing the antigen indicated reduced tumor size and increased survival in vaccinated mice (FIG. 9), The protective response to tumor was evident after vaccination at SLA:LA at 50:50 and 30:70 ratio of lipid.

B-16 Melanoma Assay

Peptides HLA.A2/H-2K$^b$ TRP-$2_{180-188}$ (SVYDFFVWL), CTL epitope from tyrosinase related protein-2 and Gp100$_{25-35}$ (KVPRNQDWL) from human melanoma antigen Gp100 were synthesized. GP100$_{25-33}$ or TRP-$2_{181-189}$ was entrapped separately using methodology for antigen entrapment as described above for ovalbumin. Peptide amounts were assayed by RP-HPLC using a Zorbax C-18 reverse-phase column (150×4.6 mm) with a guard cartridge installed in a DX-300 Dionex dual piston HPLC system (Sunnyvale, Calif.). The peptides were eluted at a flow rate of 1 ml/min using a gradient aqueous mobile phase from 2% acetonitrile in 0.1% TEA to 70% acetonitrile in 0.085% TFA over 60 min, and revealed by UV absorbance at a 216 nm wavelength. Integration was done by a Dionex 4290 integrator. Quantification was done using a calibration curve based on known amounts of each of the respective peptides.

C57BL/6 mice were immunized subcutaneously with 15 µg of TRP or Gp100 antigen in liposomes on day 0, 3.5 weeks and 8.5 weeks. B-16 melanoma tumor cells were grown in the laboratory as per previously published methods (Krishnan et al., Cancer Research, 63:2526, 2003). Mice were injected with $10^6$ B16 tumor cells (in PBS plus 0.5% normal mouse serum) in the shaved lower dorsal region, 11.5 weeks post first vaccination, From day 5 onwards, palpable solid tumors were measured using digital calipers. Tumor size, expressed in $mm^2$, was obtained by multiplication of diametrically perpendicular measurements. Mice were euthanized when the tumor sizes reached a maximum of 300 $mm^2$.

Figure 10:
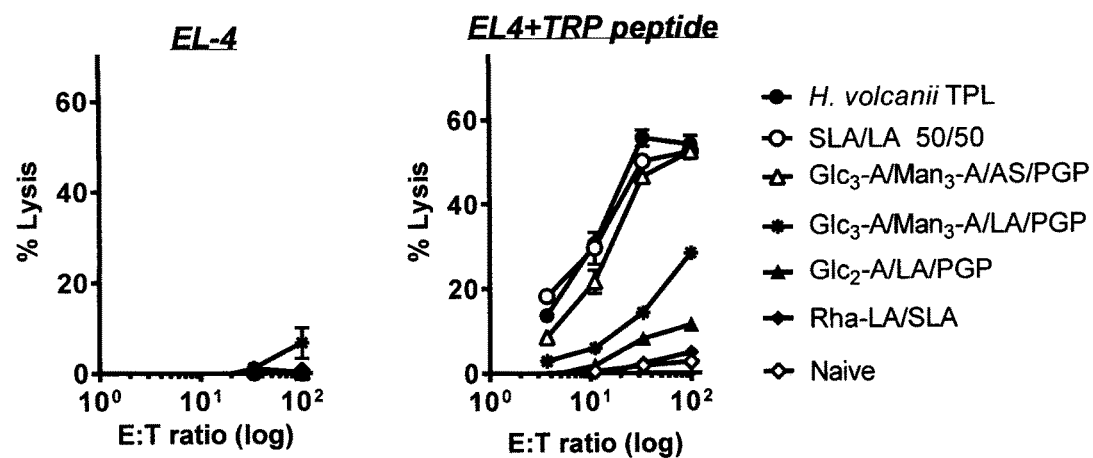
FIG. 10 shows graphs illustrating the results of a T cell immune response against a cancer self-antigen TRP-2 peptide delivered in liposome formulation comprised of 50:50 ratio of SLA:LA in comparison to other semi-synthetic liposome formulations. Mice were vaccinated twice (15 µg of TRP-2 peptide per mouse per injection, subcutaneous) on day 0 and 21 and the immune response was ascertained in spleens after euthanasia of the immunized mice. Cytotoxic T lymphocyte response was assessed at 5.5 weeks post first immunization (FIG. 10a) using splenic effector on non-specific EL-4 targets and antigen (TRP-2) pulsed specific targets (EL4+TRP) by standard chromium release killing assay. The ability of splenic effectors to produce IFN-gamma in response to antigenic stimulation was assessed by ELISPOT (FIG. 10b).
Figure 10:
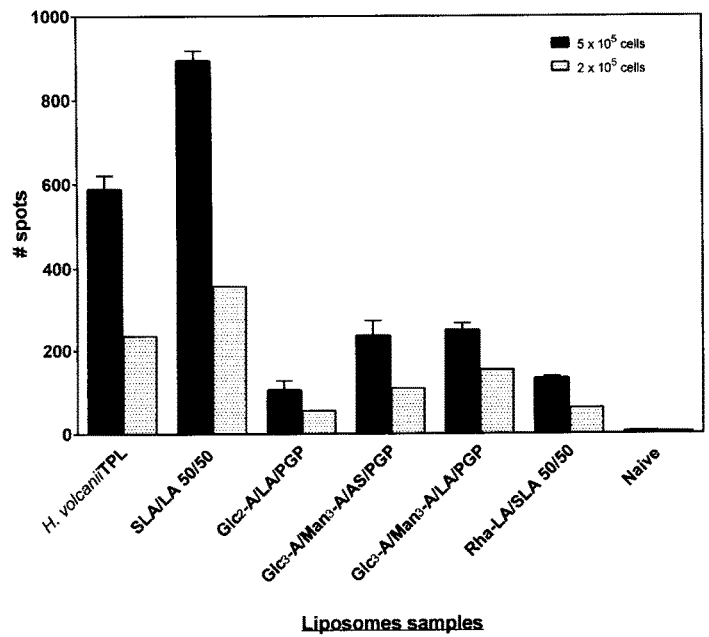
Figure 11:
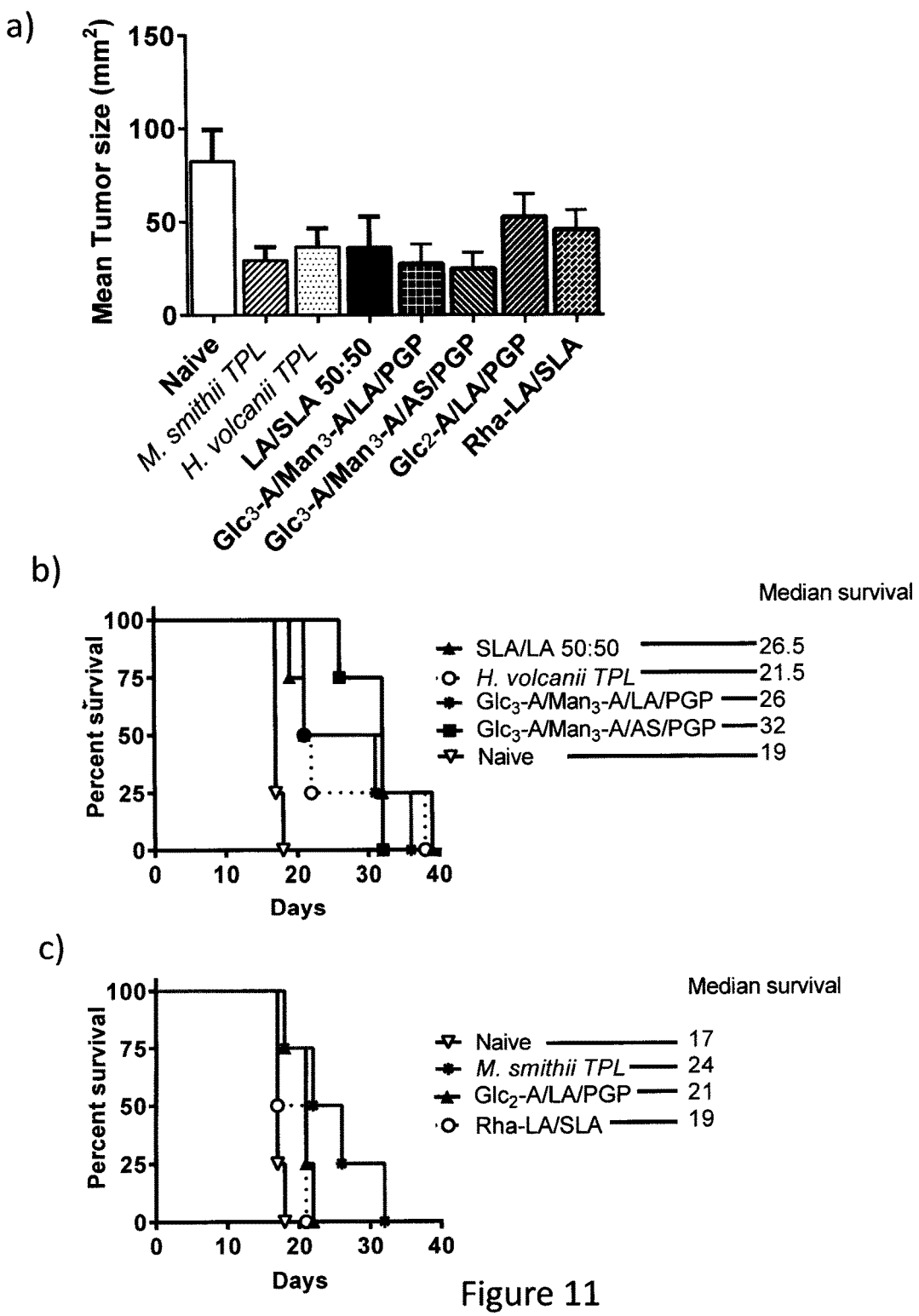
FIG. 11 shows graphs illustrating the results of a tumor challenge study in vaccinated mice using additional liposomal formulations. Animals were vaccinated with indicated liposomes containing the TRP-2 peptide antigen (15 µg of TRP per mouse per injection, subcutaneous) twice on day 0 and 21. At 6 weeks post-vaccination, animals were injected with B16 melanoma tumor cells in the mid-back. Archaeosomes prepared from the total polar lipids of M. Smithii containing TRP were used as controls. The average tumor size in various groups is shown on day 14 after tumor challenge (11a). The mean survival of mice following tumor challenge is also illustrated (FIGS. 11b and 11c).
Figure 12:
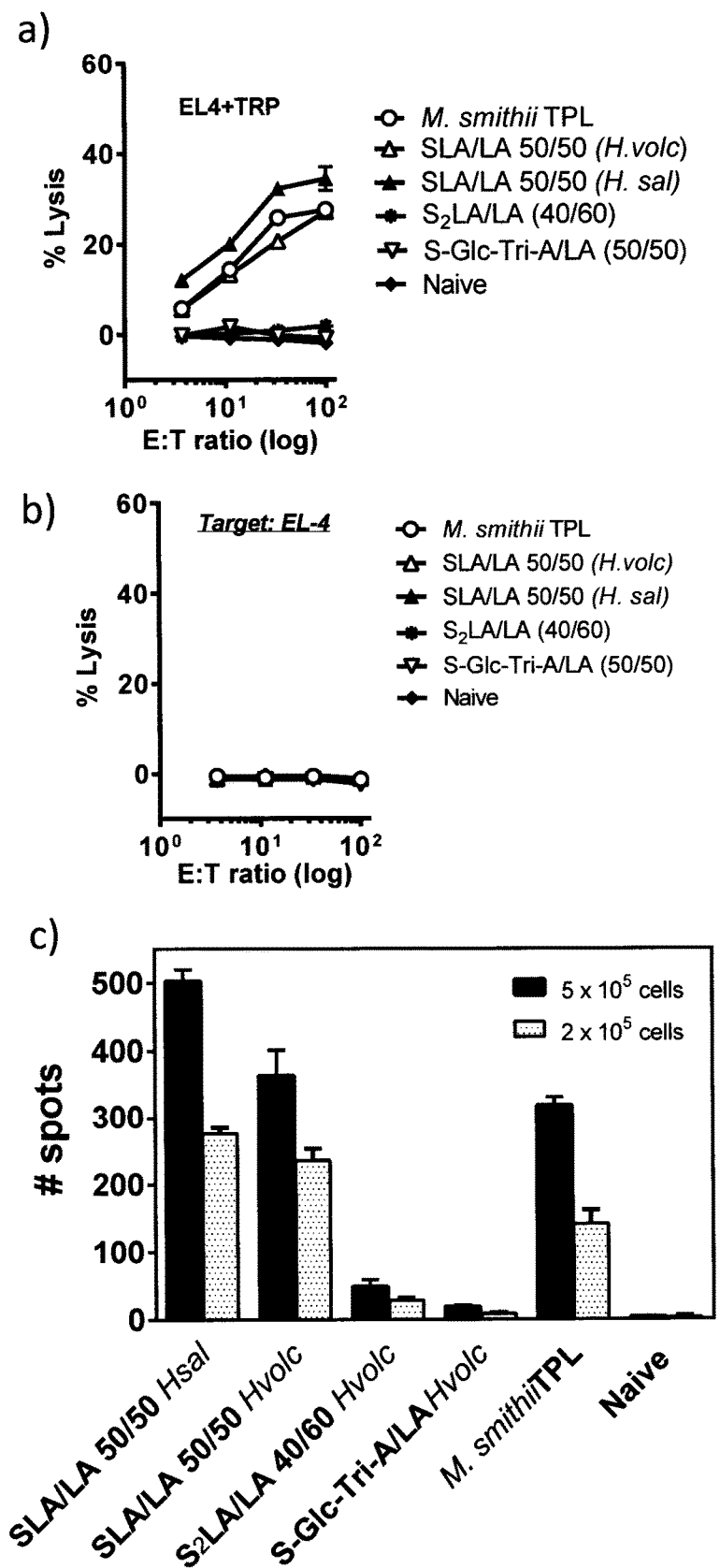
FIG. 12 illustrates the immune response induced in mice vaccinated with di-sulfated lactosyl archaeol and sulfated-trisaccharide archaeol in comparison to the sulfated lacotsyl archaeol (SLA). Mice were vaccinated thrice on day 0, 21 and 95 days with TRP (15 µg)-liposome formulations as indicated. The CTL response of splenic effectors was ascertained at 15.5 weeks post-first injection, against non-specific EL-4 and TRP-pulsed EL-4 (specific) targets (FIGS. 12a & b) by standard chromium release killing assay. The frequency of antigen-specific IFN-gamma producing splenic effectors was also determined at 15.5 weeks by an ELISPOT assay (FIG. 12c).

In another example, formulations comprising of TRP-SLA/LA were observed to induce often superior CD8+ CTL response and IFN-gamma ELISPOT response in vaccinated mice in comparison to several other synthetic archaeosome formulations (FIG. 10) which also embodied adjuvant activity as previously disclosed. This correlated to a protective efficacy to tumor challenge with B16 melanoma cells in vaccinated mice (FIG. 11). Additionally, in another example, SLA that was synthesized by chemical linkage to archaeol purified from two different archaeal species, *H. salinarum* and *H. volcanii* both were equally effective at inducing a strong adjuvant activity and CD8+ T cell response in vaccinated mice (FIG. 12).

Figure 13:
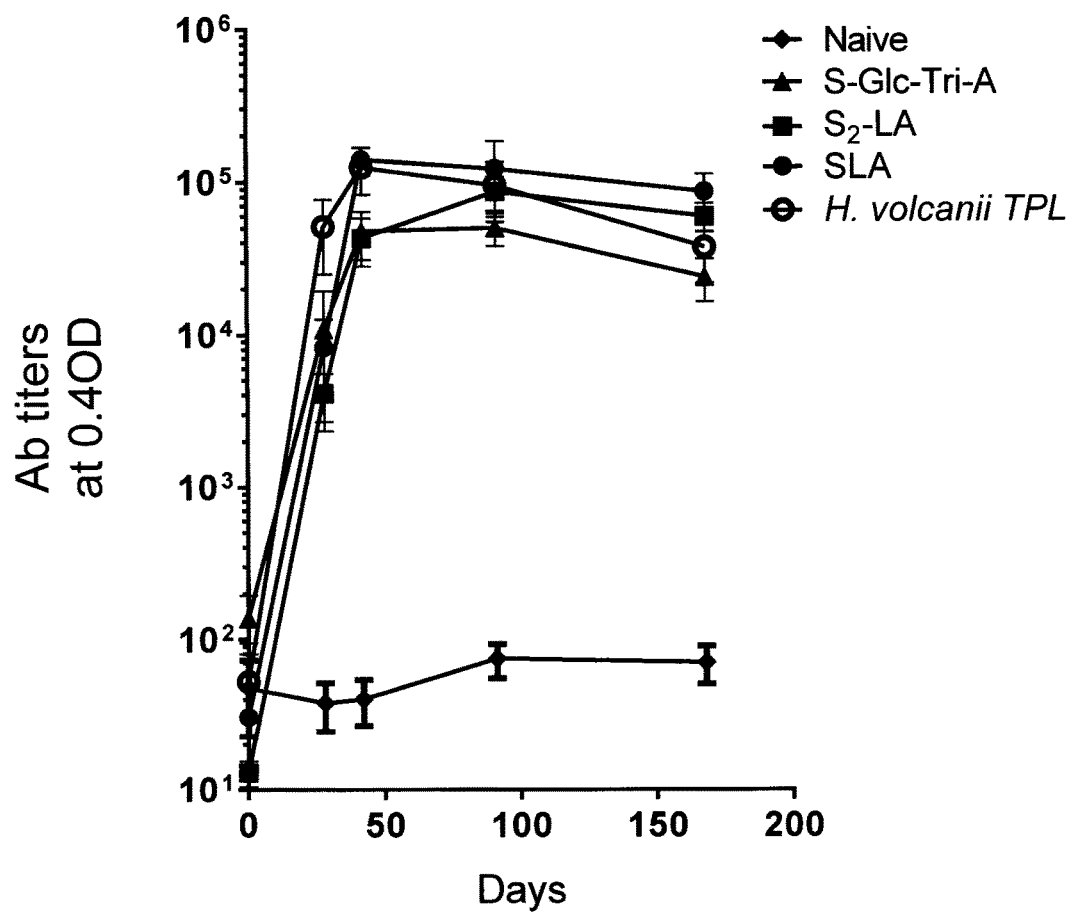
FIG. 13 shows a graph demonstrating the antibody response to antigen (ovalbumin-OVA) in serum of mice vaccinated with OVA-archaeosomes comprised of SLA (sulfated lactosyl archaeol), di-sulfated LA, sulfated-trisaccharide archaeol or TPL archaeosomes from *H. volcanii*. Mice were immunized on day 0 and 21. Antibody titres are represented as reciprocal dilution and OD. 0.4. Data show that all sulfated archaeosome types evoke strong antibody response.

In a further example, the antibody response to antigen (ovalbumin-OVA) in serum was determined in mice vaccinated with OVA-archaeosomes comprised of SLA (sulfated lactosyl archaeol), di-sulfated LA, sulfated-trisaccharide archaeol and TPL archaeosomes from *H. volcanii*. Mice were immunized on day 0 and 21. As shown in FIG. 13, all sulfated archaeosome types evoke strong antibody response.

One or more currently preferred embodiments have been described by way of example. It will be apparent to persons skilled in the art that a number of variations and modifications can be made without departing from the scope of the invention as defined in the claims.

What is claimed is:

1. A synthetic charged isoprenoid glycolipid comprising a sulfated saccharide group covalently linked to the free sn-1 hydroxyl group of the glycerol backbone of an archaeal core lipid via a beta linkage, or a pharmaceutically acceptable salt thereof, wherein the synthetic charged glycolipid is a compound of the formula:

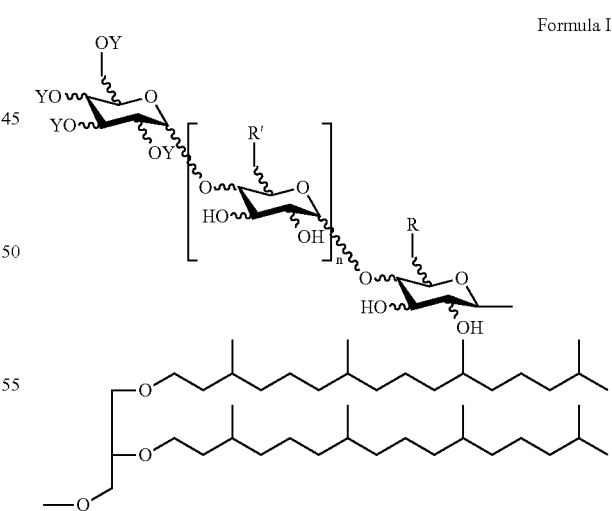

Formula I wherein
n is 0 or 1;
R and R' are independently hydrogen or hydroxyl; and
Y is hydrogen or a sulfate group, and at least one Y is a sulfate group;
or a pharmaceutically acceptable salt thereof.

2. The synthetic charged glycolipid according to claim 1, wherein one Y is a sulfate group.

3. The synthetic charged glycolipid according to claim 1, wherein the sulfated saccharide group comprises monosaccharide moieties selected from the group consisting of mannose (Man), glucose (Glc), rhamnose (Rha) and galactose (Gal) moieties.

4. The synthetic charged glycolipid according to claim 3, wherein the compound comprises a sulfate group at the 6' position of the terminal monosaccharide moiety.

5. The synthetic charged glycolipid according to claim 1, wherein n is 0 and R is OH.

6. The synthetic charged glycolipid according to claim 1, wherein the compound is 6"-sulfate-α-D-$Man_p$-(1,6)-β-D-$Gal_p$-(1,4)-β-D-$Glc_p$-(1,1)-archaeol, or 6"-sulfate-β-D-$Glc_p$-(1,6)-β-D-$Gal_p$-(1,4)-β-D-$Glc_p$-(1,1)-archaeol, or 6"-sulfate-β-D-$Gal_p$-(1,4)-β-D-$Glc_p$-(1,6)-β-D-$Glc_p$-(1,1)-archaeol.

7. The synthetic charged glycolipid according to claim 1, wherein the sulfated disaccharide group is a sulfated lactosyl group.

8. The synthetic charged glycolipid according to claim 7, wherein the sulfated lactosyl group is a 6'-S-lactosyl group.

9. The synthetic charged glycolipid according to claim 8, wherein the 6'-S-lactosyl group is 6'-sulfate-β-D-$Gal_p$-(1,4)-β-D-$Glc_p$.

10. The synthetic charged glycolipid according to claim 1, wherein the synthetic charged glycolipid is: (2R)-2,3-Bis[(3R,7R,11R)-3,7,11,15-tetramethylhexadecyloxy]propan-1-yl 4-O-(6-O-sulfo-β-D-galactopyranosyl)-β-D-glucopyranoside.

11. The synthetic charged glycolipid according to claim 1, of the structure:

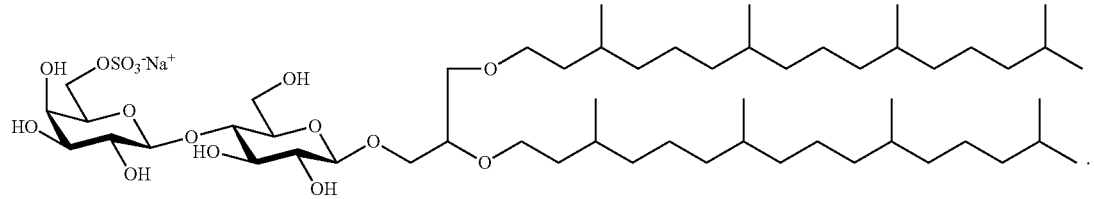

12. The synthetic charged glycolipid according to claim 1, wherein said pharmaceutically acceptable salt is a sodium, calcium or magnesium salt.

13. An archaeosome comprising at least one synthetic charged glycolipid comprising a sulfated saccharide group covalently linked to the free sn-1 hydroxyl group of the glycerol backbone of an archaeal core lipid via a beta linkage, or a pharmaceutically acceptable salt thereof.

14. The archaeosome according to claim 13, further comprising at least one additional lipid.

15. The archaeosome according to claim 14, wherein the at least one additional lipid is a neutral, or uncharged glycolipid.

16. The archaeosome according to claim 15, wherein the at least one additional lipid is selected from the group consisting of lactosylarchaeol, rhamnosyl-lactosylarchaeol, triglucosylarchaeol, monophosphoryl Lipid A, and combinations of any two or more thereof.

17. The archaeosome according to claim 15, wherein the mol % ratio of the synthetic charged glycolipid to the neutral or uncharged lipid is from 100:0 to 30:70.

18. The archaeosome according to claim 15, wherein the mol % ratio of the synthetic charged glycolipid to the neutral or uncharged lipid is about 50:50.

19. The archaeosome according to claim 13, comprising 6'-sulfate-lactosylarchaeol and uncharged lactosylarchaeol in a mol % ratio of from 100:0 to 30:70.

20. The archaeosome according to claim 19, wherein the mol % ratio of 6'-sulfate-lactosylarchaeol to uncharged lactosylarchaeol is about 50:50.

21. The archaeosome according to claim 13, having an average diameter of between 50 nm and 350 nm.

22. A vaccine or composition comprising an adjuvant and an antigen, the adjuvant comprising an archaeosome according to claim 13.

23. The vaccine or composition according to claim 22, wherein the antigen comprises a peptide or protein.

24. The archaeosome according to claim 13, wherein the synthetic charged glycolipid is a compound of the formula:

Formula I

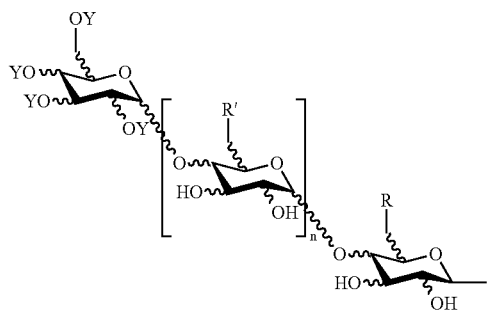

-continued

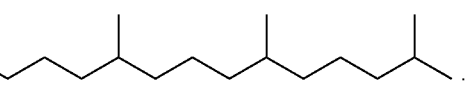

wherein
n is 0 or 1;
R and R' are independently hydrogen or hydroxyl; and
Y is hydrogen or a sulfate group, and at least one Y is a sulfate group;
or a pharmaceutically acceptable salt thereof.

25. The archaeosome according to claim 24, further comprising at least one additional lipid, wherein the at least one additional lipid is a neutral or uncharged lipid.

26. The archaeosome according to claim 25, wherein the at least one additional lipid is selected from the group consisting of lactosylarchaeol, rhamnosyl-lactosylarchaeol, triglucosylarchaeol, monophosphoryl Lipid A, and combinations of any two or more thereof.

27. The archaeosome according to claim 25, wherein the mol % ratio of the synthetic charged glycolipid to the neutral or uncharged lipid is from 100:0 to 30:70.

28. The archaeosome according to claim 25, wherein the mol % ratio of the synthetic charged glycolipid to the neutral or uncharged lipid is about 50:50.

29. The archaeosome according to claim 24, having an average diameter of between 50 nm and 350 nm.

30. A vaccine or composition comprising an adjuvant and an antigen, the adjuvant comprising an archaeosome according to claim 24.

31. A method of promoting an immune response in a subject, said method comprising administering a vaccine or composition according to claim 22 in an amount effective to produce an immune response in said subject.

32. The method of claim 31, wherein the subject is a mammal.

33. The method of claim 32, wherein the mammal is a human.

* * * * *